(12) United States Patent
Lothstein et al.

(10) Patent No.: US 7,541,342 B2
(45) Date of Patent: Jun. 2, 2009

(54) USE OF PKC-ACTIVATING COMPOUNDS AS CARDIOPROTECTANTS AND AS APOPTOSIS-INDUCING ANTI-TUMOR AGENTS

(75) Inventors: Leonard Lothstein, Eads, TN (US);
Mervyn Israel, Germantown, TN (US);
Trevor Sweatman, Memphis, TN (US);
Polly A. Hofmann, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 100 days.

(21) Appl. No.: 11/369,225

(22) Filed: Mar. 6, 2006

(65) Prior Publication Data

US 2006/0199775 A1    Sep. 7, 2006

Related U.S. Application Data

(60) Provisional application No. 60/658,988, filed on Mar. 4, 2005.

(51) Int. Cl.
*A01N 43/04* (2006.01)
*A61K 31/70* (2006.01)

(52) U.S. Cl. .................. 514/34; 514/25; 514/33; 514/35

(58) Field of Classification Search .................. None
See application file for complete search history.

(56) References Cited

U.S. PATENT DOCUMENTS

4,610,977 A    9/1986    Israel et al.
6,677,309 B1    1/2004    Taatjes et al.

OTHER PUBLICATIONS

Barrett et al. Molecular Cancer Therapeutics (2002), vol. 1, pp. 469-481.*
Overmoyer Journal of Clinical Oncology (2003), vol. 21, pp. 580-582.*
Campos et al. Blood (1993), vol. 81, pp. 3091-3096.*
Kantarjian et al. The New England Journal of Medicine (2002), vol. 346, pp. 645-652.*
Notification Concerning Transmittal Of International Preliminary Report on Patentability (Chapter I of the Patent Cooperation Treaty) corresponding to PCT Application No. PCT/US2006/007853 dated.
International Search Report and Written Opinion of the International Searching Authority corresponding to PCT application No. PCT/US06/07853 dated Jun. 29, 2006.
Bachur et al., "Anthracycline Antibiotic Blockade of SV40 T Antigen Helicase Action", *Biochemical Pharmacology*, 55: 1025-1034, 1998.
Esteva et al., "Chemotherapy of Metastic Breast Cancer: What to Expect in 2001 and Beyond," The Oncologist, vol. 6, pp. 133-146 (2001).
Grazette et al., "Inhibition of ErbB2 Causes Mitochondrial Dysfunction in Cardiomyocytes," Journal of the American College of Cardiology, vol. 44, No. 11 (2004).
He et al., "N-Benzyladriamycin-14-Valerate (AD 198) Induces Apoptosis through Protein Kinase C-δ-Induced Phosphorylation of Phospholipid Scramblase 3," Cancer Res., vol. 65, No. 21, pp. 10016-10023 (Nov. 1, 2005).
Liu et al., "Protein Kinase C-δ and Its Downstream Effectors as Potential Targets for Cancer Therapy," Cancer Therapy, vol. 1, pp. 275-281 (2003).
Roaten et al., "Interaction of the Novel Anthracycline Antitumor Agent N-Benzyladriamycin-14-valerate with the C1-Regulatory Domain of Protein Kinase C: Structural Requirements, Isoform Specificity, and Correlation with Drug Cytotoxicity," Molecular Cancer Therapeutics, vol. 1, pp. 483-492 (May 2002).
Roaten et al., "Molecular Models of N-Benzyladriamycin-14-valerate (AD 198) in Complex with the Phorbol Ester-Binding C1b Domain of Protein Kinase C-δ," J. Med. Chem., vol. 44, pp. 1028-1034 (2001).
Slamon et al., "Use of Chemotherapy Plus a Monoclonal Antibody Against HER2 for Metastatic Breast Cancer that Overexpresses HER2," The New England Journal of Medicine, vol. 344, No. 11, pp. 783-792 (Mar. 15, 2001).
Barrett et al., "Novel Extranuclear-targeted Anthracyclines Override the Antiapoptotic Functions of Bcl-2 and Target Protein Kinase C Pathways to Induce Apoptosis", Molecular Cancer Therapeutics, vol. 1, pp. 469-481 (May 2002).
Lothstein et al., "Cytotoxicity and Intracellular Biotransformation of N-Benzyladriamycin-14-Valerate (AD 198) Are Modulated by Changes in 14-O-acyl Chain Length", Anti-Cancer Drugs, vol. 9, pp. 58-66 (1998).

* cited by examiner

*Primary Examiner*—Patrick T Lewis
(74) *Attorney, Agent, or Firm*—Jenkins, Wilson, Taylor & Hunt, P.A.

(57) ABSTRACT

Compounds for the inducing apoptosis in cancer cells are described. The described compounds induce the translocation of protein kinase C-δ to the mitochondria and the phosphorylation of mitochondrial phospholipid scramblase 3. The compounds also provide cardioprotection through the translocation and activation of protein kinase C-ε in cardiomyocytes, thereby inhibiting apoptosis in carciomyocytes.

20 Claims, 53 Drawing Sheets

USE OF PKC-ACTIVATING COMPOUNDS AS CARDIOPROTECTANTS AND AS APOPTOSIS-INDUCING ANTI-TUMOR AGENTS

CROSS REFERENCE TO RELATED APPLICATIONS

This application is based on and claims priority to U.S. Provisional Patent Application Ser. No. 60/658,988, filed Mar. 4, 2005, which is incorporated herein by reference in its entirety.

GOVERNMENT INTEREST

This invention was made with U.S. Government support from the U.S. National Institutes of Health/National Cancer Institute (NIH/NCI) grant nos. CA100093 and CA44890. The U.S. Government has certain rights in the invention.

TECHNICAL FIELD

The currently disclosed subject matter relates to methods of inducing apoptosis in tumor cells and for cardioprotection in a subject undergoing treatment for a cancer by administering a therapeutic amount of an 14-O-acyl anthracycline derivative, e.g., N-benzyladriamycin-14-valerate (AD 198) or N-benzyladriamycin-14-pivalate (AD 445), to a subject in need of treatment thereof.

Abbreviations

° C.=degrees Celsius
$\Delta\psi_m$=mitochondrial membrane potential
ATP=adenosine triphosphate
BAPTA-AM=1,2-bis(o-aminophenoxy)ethane-N,N,N', N'-tetraacetic acid tetra(acetoxymethyl) ester
Ca=calcium
CM-$H_2$DCFDA=5-(and-6)-chloromethyl-2',7'-dichlorodihydro-fluoresceindiacetate, acetyl ester
CML=chronic myelogenous leukemia
CsA=cyclosporine A
DAG=diacylglycerol
DMSO=dimethylsulfoxide
DNA=deoxyribonucleic acid
DNR=daunorubicin
DOX=doxorubicin
EDP=end diastolic pressure
EGTA=ethyleneglycol-bis-($\beta$-aminoethyl)-N,N,N',N'-tetraacetic acid
HER2=human epidermal growth factor receptor 2
$H_2O_2$=hydrogen peroxide
hr=hour(s)
HRP=horseradish peroxidase
IPC=ischemic preconditioning
i.v.=intravenous
$LD_{50}$=lethal dose, 50 percent
LVDP=left ventricular developed pressure
$\mu M$=micromolar
min=minute(s)
MRP-1=multi-drug resistance protein
MTT=3-(4,5-dimethylthiazol-2-yl)-2,5-diphenyltetrazolium bromide
Ni=nickel
nM=nanomolar
NRVM=neonatal rat ventricular myocytes
PBS=phosphate buffered saline
PI=propidium iodide
PKC=protein kinase C
PLS3=phospholipid scramblase 3
PT=phosphothreonine
PTPC=permeability transition pore complex
ROS=reactive oxygen species
SD=standard deviation
SDS-PAGE=sodium dodecylsulfate-polyacrylamide gel electrophoresis
siRNA=small interfering ribonucleic acid
topo II=DNA topoisomerase II

BACKGROUND

Doxorubicin (DOX), also known as adriamycin, is an anthracycline antibiotic that has been used extensively over the past four decades to treat a wide variety of solid and hematopoietic tumors. The anthracyclines are a family of chemically-related anthraquinone-glycoside compounds of natural and synthetic origin. Many of the anthracyclines, including DOX and daunorubicin (DNR), another widely used anthracycline anti-cancer drug, target the cell nucleus and function principally as topoisomerase II poisons, locking the DNA/topoisomerase II cleavable complex through DNA intercalation of the anthracyclines' relatively planar anthraquinone structure. The poisoning of topoisomerase II promotes the accumulation of double-stranded DNA breaks, which, in turn, triggers apoptosis. See Froelich-Ammon, S. J. and Osheroff, N., J. Biol. Chem. 270, 21429-21432 (1995).

As a clinical agent, the efficacy of DOX is often limited by multiple mechanisms of cellular drug resistance, including the overexpression of transmembrane multidrug transporters, tumor suppressor protein dysfunction, and the expression of anti-apoptotic Bcl-2 protein family members. See Booser, D. J. and Hortobagyi, G. N., Drugs, 47, 223-258 (1994); Hill, M. E., et al., Blood, 88, 1046-1051 (1996); and Lowe, S. W., et al., Science, 266, 807-810 (1994). In addition, systemic toxicities often affecting rapidly dividing hematopoietic and epithelial cells limit the doses of drugs that are administered.

The therapeutic efficacy of DOX at cumulative doses in excess of 450 mg/m$^2$ is further limited by its association with well-defined, life-threatening cardiotoxicities. See Acton, E. M. in "Anthracycline Antibiotics. Novel Analogs, Methods of Delivery and Mechanisms of Action," Priebe, W., ed., Washington, D.C.: American Chemical Society, 1995, 1-13; and Frishman, W. H. et al., Curr. Probl. In Cardiol., 21, 225-288 (1996). This cardiotoxicity is possibly the result of the generation of reactive oxygen species (ROS) by the anthracycline's anthraquinone backbone. The ROS can disrupt sarcoplasmic reticulum function, induce cardiomyocyte apoptosis, and impede myocardial contractility. The most pronounced cardiotoxic effect is cardiomyopathy (weakness of the heart) due to chronic myocardial insult. Severe DOX-induced cardiomyopathies most often present clinically as congestive heart failure with a dose-dependent probability attaining 20% at cumulative doses as low as 600 mg/m$^2$, with subsequent 50% mortality after two years without transplantation. See Frishman, W. H., et al., Curr. Probl. In Cardiol., 21, 225-288 (1996); and Jensen, B. V., et al., Ann. Oncol., 13, 699-709 (2002). In addition to this chronic effect, DOX and other commonly used anthracyclines induce acute, but often reversible, eletrocardiographic changes. See Frishman, W. H. et al., Curr. Probl. In Cardiol., 21, 225-288 (1996).

Frequency and severity of cardiotoxicity also have been observed to increase with the use of combination drug therapies involving anthracyclines. Most notably, a dramatically higher frequency of heart failure has been observed in clinical trials for a breast cancer treatment that pairs DOX with the humanized anti-erbB-2 antibody trastuzumab (HERCEPTIN®; Genentech, Inc., South San Francisco, Calif., United States of America) and cyclophosphamide (26%), or with trastuzumab in combination with paclitaxel (13%). See Salmon. D. J., et al., *N. Engl. J. Med.*, 344, 783-792 (2001). Additionally, cardiovascular damage is seen in the use of the chemotherapeutic regimen CHOP (the combination of cyclophosphamide, DOX, vinblastine, and prednisone) for Non-Hodgkins lymphoma. See Limat, S., et al., *Ann. Oncol.*, 14, 277-281 (2003).

Thus, there exists a need in the art for improved anthracycline anti-cancer agents that circumvent cellular drug resistance mechanisms and have reduced cardiotoxicity. In particular, there is a need for anthracycline anti-cancer agents having reduced cardiotoxicity, but which also maintain good cytoxicity toward cancer cells.

SUMMARY

In some embodiments, the presently disclosed subject matter provides a method for inducing apoptosis in a cell, for treating cancer, and/or for providing cardioprotection, the method comprising administering to the cell an effective amount of an anthracycline compound that is active in the cytoplasm, wherein the administering of an effective amount of an anthracycline compound to the cell induces the translocation of protein kinase C-δ (PKC-δ) to the mitochondria of the cell to induce phosphorylation of a mitochondrial protein, thereby inducing apoptosis in the cell. In some embodiments, the mitochondrial protein is phospholipid scramblase 3 (PLS3).

In some embodiments the anthracycline compound is a compound of Formula (I):

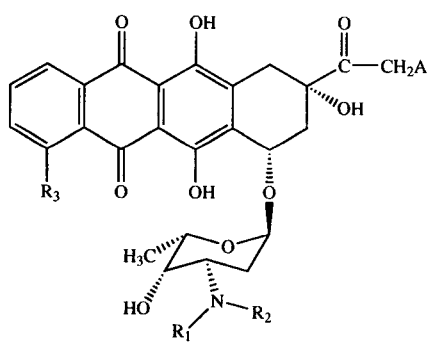

(I)

wherein:

A comprises a $C_4$-$C_8$ alkanoate moiety;

$R_1$ is H;

$R_2$ is benzyl; and $R_3$ is H or methoxy;

or a pharmaceutically acceptable salt thereof.

In some embodiments, $R_3$ is methoxy. In some embodiments, A is selected from the group consisting of:

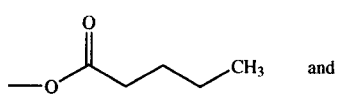

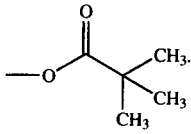

In some embodiments, the compound of Formula (I) is selected from the group consisting of:

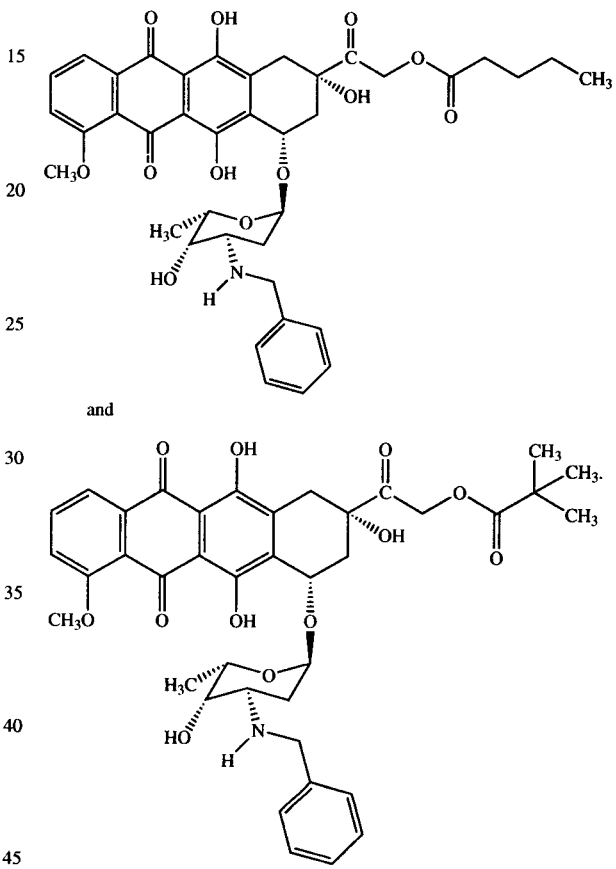

and

Also provided is a method for treating a cancer, comprising administering to a subject in need of treatment thereof an effective amount of a compound of Formula (I) as defined hereinabove. In some embodiments, the administering of an effective amount of a compound of Formula (I) can induce the translocation of PKC-δ to the mitochondria of a cancer cell to induce the phosphorylation of PLS3, thereby inducing apoptosis in the cancer cell. In some embodiments, administering an effective amount of a compound of Formula (I) provides cardioprotection to the subject in need of treatment thereof. The cardioprotection, likewise, can occur through the translocation and activation of protein kinase C-epsilon (PKC-ε), which, in turn, can activate a mechanism in cardiac myocytes that inhibits apoptosis through protection of mitochondria. In some embodiments, the method comprises administering a therapeutic amount of a compound of Formula (I) in combination with one or more additional therapeutic agents. In some embodiments, the one or more additional therapeutic agent is an anti-cancer agent. In some embodiments, the anti-cancer agent is selected from the group consisting of antimetabolites, antimicrotubule agents, alkylating agents, antibodies and combinations thereof. In some embodiments, the additional therapeutic agent comprises a monoclonal antibody. In some embodiments, the monoclonal antibody is trastuzumab (commercially available as HERCEPTIN® from Genentech, Inc., South San Francisco, Calif., United States of America). In some embodiments, the cancer comprises a human epidermal growth factor receptor 2 (HER2) positive breast cancer.

In some embodiments, the presently disclosed subject matter provides a method for treating a drug-resistant cancer, the method comprising administering to a subject in need of treatment thereof an effective amount of a compound of Formula (I) as defined herein above. In some embodiments, the administering of an effective amount of a compound of Formula (I) can induce the translocation of PKC-δ to the mitochondria of a drug-resistant cancer cell to induce the phosphorylation of PLS3, thereby inducing apoptosis in a drug resistant cancer cell. In some embodiments, the administering an effective amount of a compound of Formula (I) provides cardioprotection to the subject in need of treatment thereof. In some embodiments, the drug resistant cancer comprises an adult chronic myeloid leukemia (CML). In some embodiments, the drug-resistant leukemia is resistant to imatinib mesylate (commercially available as GLEEVEC® from Novartis Pharmaceuticals Corporation, East Hanover, N.J., United States of America).

In some embodiments, the presently disclosed subject matter provides a method for providing cardioprotection in a subject in need thereof, the method comprising administering to the subject an effective amount of a compound of Formula (I) as defined hereinabove. In some embodiments, the administering to the subject an effective amount of a compound of Formula (I) can induce the activation of PKC-ε in a cardiomyocyte, thereby inducing a cardioprotective effect.

Accordingly, it is an object of the presently disclosed subject matter to provide a method of inducing apoptosis in a cancer cell and/or providing cardioprotection.

An object of the presently disclosed subject matter having been stated herein above, which is addressed in whole or in part by the presently disclosed subject matter, other objects and aspects will become evident as the description proceeds when taken in connection with the accompanying Drawings and Examples as best described herein below.

DETAILED DESCRIPTION

Figure 1A:
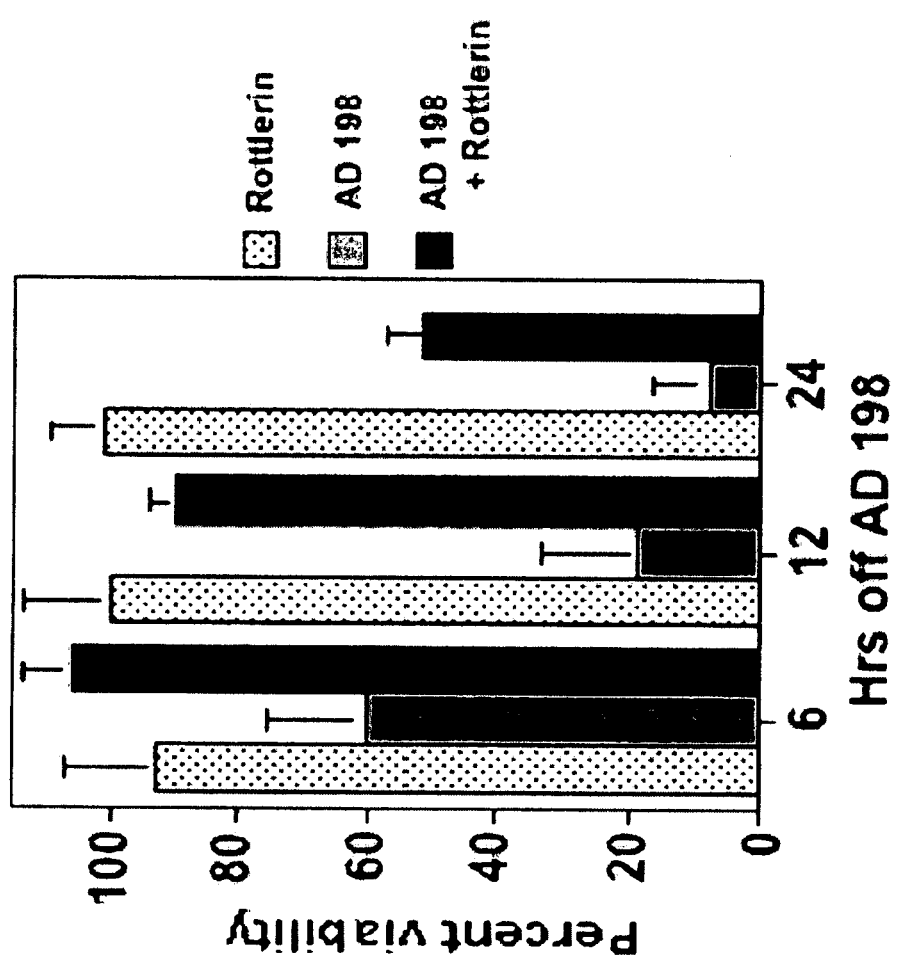
FIG. 1A is a bar graph comparing the percent viability of 32D.3 cells as determined by trypan blue staining. Rottlerin cells (stippled bars) were pretreated for 2 hr with 10 μM rottlerin. AD 198+Rottlerin cells (solid bars) were pretreated for 2 hr with 10 μM rottlerin and then treated for 1 hr with 5 μM AD 198. AD 198 cells (shaded bars) were treated for 1 hr with 5 μM AD 198. The timepoints represent cell viability 6 hr, 12 hr, and 24 hr after the end of any of the pretreatments listed above. Results represent the mean±standard error (s.e.) of three independent determinations.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

The present disclosure relates the biochemical and pharmacological properties of a family of compounds based on the structure of the C-14 alkanoate anthracycline anti-tumor agents, including N-benzyladriamycin-14-valerate (AD 198) and N-benzyladriamycin-14-pivalate (AD 445). The biochemical mechanism(s) of action and pharmacological effects of the presently disclosed compounds, in vitro and in vivo, differ significantly from those of other structurally-related anthracycline anti-tumor drugs, such as DNR and DOX, currently in wide clinical use. Without wishing to be bound to any one theory, it is believed that DNR and DOX concentrate in the nuclei of cells, where they bind strongly with DNA and interfere with the action of the enzyme DNA topoisomerase II (topo II), whereas the compounds of the presently disclosed subject matter are believed to not enter the nucleus, bind minimally to isolated DNA, and have no effect on topo II at cytotoxic doses. Furthermore, while DNR and DOX produce severe myelosuppression (suppression of white blood cell formation) and cardiac toxicity in animals and humans, the presently disclosed compounds exhibit a much wider therapeutic index (margin of safety) with regard to myelosuppression and do not damage the heart.

Thus, provided herein are methods for inducing rapid apoptosis in a cancer cell, for treating a drug-resistant cancer, and for providing cardioprotection in a subject in need thereof by administering a mechanistically-novel cytoplasmically-active anthracycline derivative to produce activation of protein kinase C holoenzymes to achieve the desired pharmacological effect(s).

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Branched alkyl" refers to an alkyl group substituted with another alkyl. Exemplary "branched alkyl" groups include isopropyl, sec-butyl, iso-butyl, tert-butyl, neo-pentyl and the like.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic alkyl" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The terms "hydroxy" and "hydroxyl" refer to the —OH group.

"Alkoxy" refers to an alkyl-O— group wherein alkyl is as previously described. The term "alkoxy" as used herein can refer to, for example, methoxy.

"Aryl-alkyl" refers to an aryl-alkyl- group, wherein aryl and alkyl are as previously described, and include substituted aryl and substituted alkyl. Exemplary aryl-alkyl groups include benzyl, phenylethyl, and naphthylmethyl. The terms "aryl-alkyl" and "aralkyl" can be used interchangably.

"Benzyl" refers to the aryl-alkyl group, $(C_6H_5)CH_2$—.

As used herein the term "alkanoate" refers to an —O—C(=O)-alkyl group. Alkanoates include, but are not limited to, pivalate, butyrate (i.e., n-butanoate), isobutanoate, valerate (i.e., n-pentanoate), isovalerate (i.e., 2-methylbutanoate), caprate (i.e., n-hexanoate), heptanoate, and caprylate (i.e., n-octanoate).

The term "oxo" refers to a double-bonded oxygen, (=O). Thus a carbon substituted with an oxo group is a carbonyl (—C(=O)—).

"Amino" refers to the —$NH_2$ group. "Alkylamino" refers to an NHR group, wherein R is an alkyl group. "Dialkylamino" refers to an amino group wherein both hydrogen atoms have been replaced by alkyl groups.

As used herein the term "apoptosis" refers to programmed cell death, a cellular process comprising the self-destruction of a cell in a multicellular organism.

The term "cancer" as used herein refers to diseases caused by uncontrolled cell division and the ability of cells to metastasize, or to establish new growth in additional sites. The terms "malignant", "malignancy", "neoplasm", "tumor" and variations thereof refer to cancerous cells or groups of cancerous cells.

Specific types of cancer include, but are not limited to, skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

The term "drug-resistant cancer" refers to a cancer which never responded to a chemotherapeutic drug or initially responded to an anti-cancer drug, but which has become resistant to the anti-cancer drug (i.e., the anti-cancer drug is no longer effective in treating the cancer). For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents. The term "refractory" also can be used to describe a cancer that has become resistant to a previously effective treatment.

The terms "cardioprotective" and "cardioprotection" refer to the ability to prevent damage to the heart, or in particular, to heart muscle cells (cardiac myocytes). The heart damage prevented can be acute damage or chronic damage. Thus, a cardioprotective compound can, in some embodiments, prevent congestive heart failure, cardiac ischemia, hypertension, hypotension, arrhythmias, and cardiomyopathy. Damage to the heart can be manifested through one or more parameters or indicia including changes to stroke volume, ejection fraction, end diastolic fraction, stroke work, arterial elastance, or by an increase in heart weight to body weight ratio. As used herein, cardioprotection also can be used to refer to the reduction or inhibition of apoptosis in cardiomyocytes.

The term "holoenzyme" as used herein refers to a complete enzyme, including all of its subunits.

As used herein, a compound that is "active in the cytoplasm" refers to a compound that does not accumulate to an appreciable extent in the nucleus of a cell and which does not target DNA.

II. General Considerations

II.A. Cardiotoxicity of Anti-Neoplastic Agents

Cardiovascular toxicities are associated with the clinical application of many cytotoxic cancer chemotherapeutic agents. See Yeh, E. T., et al., *Circulation*, 109, 3122-3131 (2004); and Morandi, P., et al., *Bone Marrow Transplant*, 35, 323-334 (2005). Such toxicity is due, at least in part to the particular sensitivity of cardiac myocytes to drug-induced oxidative damage. See Myers, C., *Semin. Oncol.*, 25, 10-14 (1998). The nature of cardiovascular damage and its significance as a dose-limiting adverse affect during therapy depends on many factors, including the mechanisms of drug action, schedule and mode of drug administration, combination with other agents, and the age and pre-existing cardiovascular status of the patient. See Yeh, E. T., et al., *Circulation*, 109, 3122-3131 (2004); and Morandi, P., et al., *Bone Marrow Transplant*, 35, 323-334 (2005). There is, nevertheless, a general correlation between types of cardiotoxicities and specific classes of drugs: ischemia and arrhythmias, observed following the use of antimetabolites or antimicrotubule agents, and congestive heart failure (CHF), observed principally with anthracycline antibiotics, alkylating agents and with certain biological agents (including antibodies such as trastuzumab, alemtuzumab, and bevacizumab). See Yeh, E. T. et al., *Circulation*, 109, 3122-3131 (2004).

Anthracyclines such as DOX and DNR exhibit the highest frequencies of serious cardiovascular abnormalities. In recent retrospective analyses of phase III clinical trials using anthracycline-based combination therapies, the frequency of CHF has been reported to escalate in a dose-dependent manner: 5% at 400 mg/m$^2$, 26% at 550 mg/m$^2$, and 48% at 700 mg/m$^2$. See Swain, S. M., et al., *Cancer*, 97, 2869-2879 (2003).

In addition to overt cardiotoxicity, the association of subclinical cardiac effects with chemotherapy remains a largely unquantified but certainly contributory factor to subsequent cardiovascular disease in surviving patients. See Schultz, P. N., et al., *Int J. Cancer*, 104, 488-495 (2003). Earlier studies have clearly shown that cardiac damage is inflicted with the initial dose of DOX, since even low doses of DOX decrease the cardiac functional reserve of the patient. See Speyer, J. and Wasserheit, C., *Semin. Oncol.*, 25, 525-537 (1998). This subclinical manifestation results in a decreased ability to compensate for superimposed cardiovascular stresses, such as acute or chronic coronary artery disease, that are either pre-existing or occurring subsequent to successful cancer chemotherapy. See Priebe, H. J., *Br. J. Anaesth.*, 85, 763-778 (2000). In an angiographic study of patients with soft tissue sarcoma in remission following treatment with DOX at 480 to 550 mg/m$^2$ body surface area, chronic left ventricular dysfunction was detected in over 50% of otherwise asymptomatic patients despite treatment with a dose range of DOX below that routinely associated with symptomatic cardiotoxicity. See Gottdiener, J. S., et al., *Ann. Intern. Med.*, 94, 430-435 (1981). Similar results in the frequency of subclinical cardiotoxicity were recently observed in surveys of children and adults who have undergone DOX therapy. See Kremer, L. C., et al., *Ann. Oncol.*, 13, 819-829 (2002); and Wassmuth, R., et al., *Am. Heart J.*, 141, 1007-1013 (2001).

Non-anthracycline agents also have been reported to produce subclinical myocardial dysfunctions. See Yeh, E. T. et al., *Circulation*, 109, 3122-3131 (2004); Slamon, D. J., et al., *N. Engl. J. Med.*, 344, 783-792 (2001); Barutca, S. et al., *Chemotherapy*, 50, 113-118 (2004); Jahanzeb, M., *Clin. Breast Cancer*, 4, 28-38 (2003); and Simbre, V. C. et al., *Paediatr. Drugs*, 7, 187-202 (2005). Aside from those patients, however, who had received high-dose anthracyclines or ionizing radiation alone or in combination with other agents (see Slamon, D. J. et al., *N. Engl. J. Med.*, 344, 783-792 (2001); and Bullock, F. A., *Primary Cardiol.*, 21, 5-11 (1995)), cardiotoxic morbidity and mortality in surviving cancer patients has been, historically, of less clinical concern than that of tumor eradication and subsequent cancer-free survival. As chemotherapeutic strategies continued to yield improvements in five year survival rates for adult (62%) and especially pediatric (75%) cancers (see Jemal, A., et al., *CA Cancer J. Clin.*, 55, 10-30 (2005); Aziz, N. M., *J. Nutr.*, 132, 3494S-3503S (2002)), the clinical concern for the prevention, detection, and treatment of both clinical and sub-clinical cardiotoxicity has, likewise, increased. See Yeh, E. T., et al., *Circulation*, 109, 3122-3131 (2004); Schultz, P. N., et al., *Int. J. Cancer*, 104, 488-495 (2003); and Simbre, V. C., *Paediatr. Drugs*, 7, 187-202 (2005). Cardiac insult by the array of currently used chemotherapeutic drugs and the continuing widespread clinical use of anthracyclines is now recognized as having serious impact on long-term quality of life for the cancer survivor, particularly for adult survivors of pediatric cancers. See Schultz, P. N., et al., *Int. J. Cancer*, 104, 488-495 (2003); Simbre, V. C., *Paediatr. Drugs*, 7, 187-202 (2005); and Krischer, J. P., et al., *J. Clin. Oncol.*, 15, 1544-1552 (1997).

Evidence suggests that DOX-related acute and chronic cardiotoxicities are the result of interference with myocardial $Ca^{2+}$ homeostasis through at least two principal pathways: DOX-mediated generation of reactive oxygen species (ROS) and DOX binding to cardiac ryanodine receptors. See Saeki, K., et al., *Life Sci.*, 70, 2377-2389 (2002). ROS are generated by one-electron redox cycling of the quinone ring structure through a non-enzymatic pathway involving coordination of a ferric ion with rings B and C of the DOX aglycone in a tight structural arrangement. See Myers, C., *Semin. Oncol.*, 25, 10-14 (1998). In the presence of water molecules, this complex initiates redox cycling to produce superoxide anions. See Olson, R. D., and Mushlin, P. S., *FASEB J.*, 4, 3076-3086 (1990). Given the absence of catalase activity in cardiomyocytes and the elimination of flutathione peroxidase activity by DOX treatment, cardiomyocytes are extraordinarily susceptible to oxidative damage. See Myers, C., *Semin. Oncol.*, 25, 10-14 (1998). The resulting ROS can produce lipid peroxidation and damage to nucleic acids and proteins, leading to apoptosis. DOX binding to ryanodine receptors on the sarcoplasmic reticulum facilitate channel opening and the release of sarcoplasmic $Ca^{2+}$ into the cytosol. See Gambliel, H. A., et al., *Biochem. Biophys. Res. Commun*, 291, 433-438 (2001). In combination with ROS oxidation of sulfhydryl groups on the $Ca^{2+}$ release channels of the sarcoplamic reticulum, DOX elevates cytosolic $Ca^{2+}$, which in turn, triggers myocardial apoptosis. See Abramson, J. J., and Salama, G., *Mol. Cell. Biochem.*, 82, 81-84 (1988). Recent findings also suggest that DOX causes myofibrillar damage in association with perturbed neuregulin-1beta (NRG-1β)/erbB-2 signaling. Sawyer, D. B., et al., *Circulation*, 105, 1551-1554 (2002). Normal erbB-2-activation is reported to promote myocyte growth and myofibrillar organization. See Zhao, Y. Y., et al., *J. Biol. Chem.*, 273, 10261-10269 (1998).

Chronic, irreversible cardiomyopathies are reported to be exacerbated by the conversion of DOX to its secondary C-13 alcoholic metabolite, doxorubicinol, as a result of cellular reductase activity. See Olson, R. D., and Mushlin, P. S., *FASEB J.*, 4, 3076-3086 (1990); and Minotti, G., et al., *Chem.*

*Res. Toxicol.*, 13, 1336-1341 (2000). Doxorubicinol is a potent inhibitor of ion-dependent pump proteins in the mitochondria, sarcoplasmic reticulum, and sarcolemma, as well as an inhibitor of $Na^+$—$K^+$ ATPase activity in the sarcolemma. See Olson, R. D., and Mushlin, P. S., *FASEB J.*, 4, 3076-3086 (1990); Olson, R. D., et al., *Proc. Natl. Acad. Sci. USA*, 85, 3585-3589 (1988); and Boucek, R. J., et al., *J. Biol. Chem.*, 262, 15851-15856 (1987). The persistence of DOX in cardiac tissue and its progressive conversion to doxorubicinol results in prolonged dose-dependent interference with calcium loading into the sarcoplasmic reticulum and consequent systolic and diastolic dysfunction.

In an effort to reduce both acute and chronic cardiotoxic effects of DOX, numerous therapeutic strategies have been applied. Reduction of DOX dosing has been utilized as an approach for achieving tumor cytotoxicity without exceeding a cumulative dose above which DOX-induced cardiomyopathies become manifest. Because cardiac damage is inflicted with the initial dose, however, lower doses of DOX still decrease the cardiac functional reserve of the patient (see Speyer, J., and Wasserheit, C., *Semin. Oncol.*, 25, 525-537 (1998)) and result in decreased ability to compensate for superimposed cardiovascular stresses, such as acute or chronic coronary artery disease, that are either pre-existing or occurring subsequent to successful cancer chemotherapy. See Priebe, H. J., *Br. J. Anaesth.*, 85, 763-778 (2000); Gottdiener, J. S., et al., *Ann. Intern. Med.*, 94, 430-435 (1981); Kremer, L. C., et al., *Ann. Oncol.*, 13, 819-829 (2002). The administration of reduced doses of DOX in combination with other chemotherapeutic agents maintains or improves antitumor efficacy, but either fails to reduce DOX-mediated cardiotoxicity (see Gianni, L., et al., *Ann. Oncol.*, 12, 1067-1073 (2002)) or, as with trastuzumab (HERCEPTIN®, Genentech, South San Francisco, Calif., United States of America), significantly increases the risk of cardiotoxicity (see Slamon, D., and Pegram, M., *Semin. Oncol.*, 28, 13-19 (2001)), with up to a 28% frequency of heart failure (see Feldman, A. M., et al., *Circulation*, 102, 272-274 (2000)) through a mechanism that reportedly involves trastuzumab-mediated interruption of erbB-2 signaling. See Sawyer, D. B., et al., *Circulation*, 105, 1551-1554 (2002).

II.B. Protein Kinase C (PKC) Enzymes

The PKC family comprises 10 members, categorized either as conventional (α, βI, βII, γ) requiring $Ca^{2+}$, DAG, and membrane phospholipid for activation, novel (δ, ε, η, and θ) which are $Ca^{2+}$ independent but DAG and phospholipid-dependent, and atypical, which are both $Ca^{2+}$ and DAG-independent. See Newton, A. C., *J. Biol. Chem.*, 270, 28495-28498 (1995). The PKC enzymes regulate a wide range of cellular functions. In particular, PKC-δ appears to play a significant role in apoptosis by regulating the expression and function of apoptosis-related proteins. See Brodie, C., and Blumberg, P. M., *Apoptosis*, 8, 19-27 (2003); and Liu, J., et al., *Cancer Therapy*, 1, 289-295 (2003). The pro-apoptotic effects of PKC-δ are reported to be both a consequence of caspase-3-mediated cleavage of the catalytic domain from the regulatory regions (see Denning, M. F., et al., *Cell Death Differ.*, 9, 40-52 (2002)), as well as the activation of PKC-δ holoenzyme. See Fujii, T. et al., *J. Biol. Chem.*, 275, 7574-7582 (2000). Under both circumstances, PKC-δ activity coincides with the translocation of PKC-δ to the mitochondrial membrane. See Denning, M. F., et al., *Cell Death Differ.*, 9, 40-52 (2002); Majumder, P. K., et al., *Cell Growth Differ.*, 129, 465-470 (2001); and Li, L., et al., *Mol. Cell Biol.*, 19, 8547-8558 (1999). PKC-δ-mediated induction of apoptosis through mitochondrial association is blocked by the expression of anti-apoptotic Bcl-2 proteins (see Fujii, T., et al., *J. Biol. Chem.*, 275, 7574-7582 (2000)) and renders those cells resistant to apoptosis triggered by various stimuli, including antitumor anthracyclines. See Jäättelä, M., *Exp. Cell Res.* 248, 30-43 (1999).

The target molecules of activated PKC-δ are not fully identified, but are reported to include:

1) c-Abl, resulting in a change in changes in mitochondiral membrane potential ($\Delta\psi_m$) and necrotic-like cell death, see Kumar, S., et al., *J. Biol. Chem.*, 276, 17281-17285 (2001);

2) p73β tumor suppressor protein, phosphorylated by the caspase-generated catalytic fragment, see Ren, J., et al., *J. Biol. Chem.*, 277, 33758-33765 (2002);

3) lamin, whose phosphorylation results in nuclear lamina disassembly during apoptosis, see Cross, T., et al., *Oncogene*, 19, 2331-2337 (2000);

4) DNA-dependent protein kinase (DNA-PK), see Bharti, A., et al., *Mol. Cell Biol.*, 18, 6719-6728 (1998); and 5) phospholipid scramblase 3 (PLS3), a mitochondiral associated enzyme which regulates mitochondrial structure, respiratory function, cardiolipin movement between the inner and outer mitochondrial membranes, and apoptotic response, see Liu, J., et al., *Mol. Cancer Res.*, 1, 892-902 (2003).

Within the context of the regulation of cardiac damage, PKC signaling appears to play a critical protective role. Ischemically-induced myocardial damage can be attenuated by short duration, transient ischemia (ischemic preconditioning (IPC)). See Murray, C. E., et al., *Circulation*, 74, 1124-1136 (1986). IPC is associated with receptor-mediated actions of a variety of ligands in combination with ROS generated via production of nitric oxide by $Ca^{2+}$-dependent nitric oxide reductase. See Cohen, M. V., et al., *Annu. Rev. Physiol.*, 62, 79-109 (2000). Sublethal levels of ROS are required for IPC by activating phospholipase, which, in turn, generates DAG. See Cohen, M. V., et al., *Annu. Rev. Physiol.*, 62, 79-109 (2000). The generation of DAG leads to the activation of PKC, which is an essential nexus of signaling for cell surface receptors involved in both the early and late phases of IPC. See Cohen, M. V., et al., *Annu. Rev. Physiol.*, 62, 79-109 (2000); and Bolli, R., *Circ. Res.* 87, 972-983 (2000). The use of isozyme-specific PKC inhibitors in isolated rabbit cardiomyocytes reveals that PKC-ε is responsible for cardioprotection following IPC. See Liu, G. S., et al., *J. Mol. Cell Cardiol.*, 31, 1937-1948 (1999). A role for PKC-δ activation in promoting preconditioning, however, also has been reported. See Kawamura, S., et al., *Am. J. Physiol.*, 275, H2266-H2271 (1998).

Multiple events downstream of PKC activation could feed back to enhance cell surface receptor-mediated signaling (see Oldenburg, O. et al., *Cardiovasc. Res.*, 55, 429-437 (2002)) or could signal further downstream events, such as the activation of p38-MAPKβ (see Yue, Y., et al., *Am. J. Physiol.*, 281, H590-H595 (2001)), p42/p44 ERK, or c-JUN N-terminal kinase. See Baines, C. P., et al., *J. Mol. Cell. Cardiol.*, 29, 207-216 (1997). Recent evidence suggests that PKC-ε forms a complex, or "signaling module" with these MAPKs following translocation of PKC-ε from cytosol to mitochondria and subsequent activation. See Baines, C. P., et al., *J. Mol. Cell. Cardiol.*, 29, 207-216 (1997). This PKC-ε/MAPK active complex results in the inhibition of mitochondrial-dependent apoptosis. See Baines, C. P., et al., *J. Mol. Cell. Cardiol.*, 29, 207-216 (1997). In addition, PKC-ε is reported to associate with no less than 36 structural, signaling, and stress-activated proteins in cardiomyocytes that ultimately function to maintain homeostasis. See Ping, P., et al., *Circ. Res.*, 88, 59-62 (2001). Following activation by PKC-ε, the MAPKs trigger downstream IPC effector events, such as phosphorylation and translocation of heat-shock protein HSP27, which is thought to then stabilize stress fibers to resist oxidative damage and myocardial swelling during ischemia. See Yue, Y., et al., *Am. J. Physiol.*, 281, H590-H595 (2001); Huot, J., et al., *Circ. Res.*, 80, 383-392 (1997); and Sanada, S., et al., *Circ. Res.*, 88, 175-180 (2001). Increased HSP70 expression also is reported to contribute to late phase IPC (see Gray, M. O. et al., *J. Biol. Chem.*, 272, 30945-30951 (1997) and Zhou, J. J., et al., *Am. J. Physiol. Heart Circ. Physiol.*, 281, H40-H47 (2001)), reportedly through improved contractile function leading to a reduction in the cardiac infarct area. See Marber, M. S., et al., *J. Clin. Invest*, 95, 1446-1456 (1995). PKC-mediated phosphorylation of myofilament proteins troponin T (cTnT) and troponin I reduces calcium-dependent actomycin $Mg^{2+}$-ATPase activity. See Pyle, W. G. et al., *Am. J. Physiol. Heart Circ. Physiol.*, 279, H1941-H1948 (2000); Pyle, W. G., et al., *Am. J. Physiol. Heart Circ. Physiol.*, 281, H669-H678 (2001); Noland, Jr., T. A., et al., *J. Mol. Cell Cardiol.*, 25, 53-65 (1993); Noland, Jr., T. A., et al., *J. Biol. Chem.*, 270, 25445-25454 (1995). The net effect of this cardioprotective signaling cascade is inhibition of myocardial apoptosis, reduced contractile activity, and reduced ATP consumption. See Ebus, J. P., and Stienen, G. J. M., *Pflugers Arch.*, 432, 921-929 (1996).

Late-phase IPC is thought to proceed down a phosphorylative pathway with PKC occupying an essential proximal position. Evidence suggests that the protein tyrosine kinases (PTK) Src and Lck are involved, with at least Lck identified as a direct substrate of PKC-ε. See Song, C., et al., *Circulation*, 102, A1021 (2000). PKC-η translocation has also been observed in association with late-phase IPC. See Bolli, R., *Circ. Res.*, 87, 972-983 (2000). Downstream targets of the PTKs could include inducible nitric oxide synthase (iNOS), whose activation is blocked by PTK inhibitors. See Bolli, R., *Circ. Res.*, 87, 972-983 (2000). In addition, PTKs, PKC-ε, and the MAPKs all appear to contribute to the activation of the transcriptional factor MF-κB, which, in turn, transactivates genes whose encoded proteins, such as iNOS, COX-2, aldose reductase, and heat shock proteins, appear to be required for late phase preconditioning events. See Bolli, R., *Circ. Res.*, 87, 972-983 (2000).

In summary, the early phase of IPC, triggered by ischemic or direct stimulation of cell surface receptors, induces both immediate effector events that conserve ATP consumption and suppress apoptotic signaling, and also triggers late phase preconditioning resulting in delayed, but similar, cardioprotective events. In both phases, PKC-ε activity appears to be essential in inducing phosphorylation cascades necessary for cardioprotective signaling.

II.C. C-14 Alkanoates of Adriamycin

A family of N-substituted, C-14 alkanoate anthracycline anti-tumor agents is described in U.S. Pat. No. 4,610,977 to Israel. M. and Seshadri, R., incorporated herein by reference in its entirety. This series of compounds includes N-benzyladriamycin-14-valerate (AD 198). See Scheme 1, below.

Scheme 1. Structures of Adriamycin-based compounds

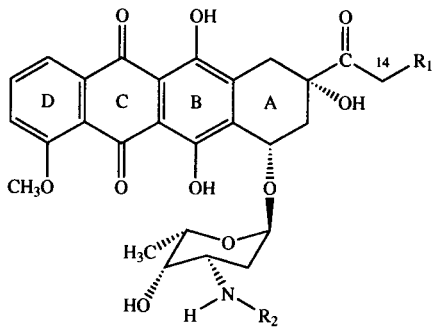

| Chemical Name | Code | $R_1$ | $R_2$ |
|---|---|---|---|
| Doxorubicin | DOX | OH | H |
| Daunorubicin | DNR | H | H |
| N-Benzyladriamycin | AD 288 | H | —$CH_2C_6H_5$ |
| N-Benzyladriamycin-14-valerate | AD 198 | ![valerate] | —$CH_2C_6H_5$ |
| N-Benzyladriamycin-14-pivalate | AD 445 | ![pivalate] | —$CH_2C_6H_5$ |

Although AD 198 is hydrolyzed in vivo to form N-benzyladriamycin (AD 288, Scheme 1), parental AD 198 does not act only as a prodrug of AD 288, which is a topoisomerase II catalytic inhibitor. See Lothstein, L., et al., *Anti-cancer Drugs*, 9, 58-66 (1998). AD 445 is less susceptible to hydrolysis, presumably as a result of steric protection of the ester bond by the bulky pivalate group. See Lothstein, L., et al., *Anti-cancer Drugs*, 9, 58-66 (1998). Thus, compared to AD 198, AD 445 persists longer in cells.

III. Active Compounds and Compositions

III.A. Compounds of Formula (I)

The presently disclosed subject matter provides anthracycline compounds that are active in the cytoplasm. In some embodiments, the presently disclosed subject matter provides compounds having structures of Formula (I):

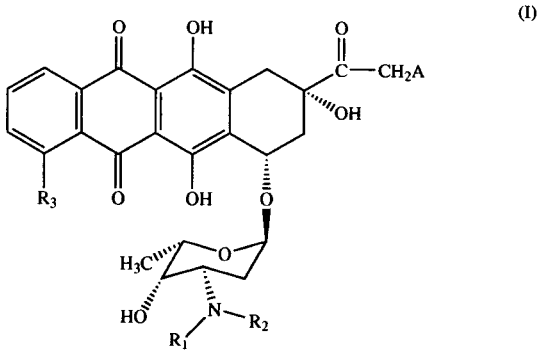

(I)

wherein:

A comprises a $C_4$-$C_8$ alkanoate moiety;

$R_1$ is H;

$R_2$ is benzyl; and $R_3$ is H or methoxy;

or a pharmaceutically acceptable salt thereof.

In some embodiments $R_3$ is methoxy. In some embodiments, A is selected from the group consisting of:

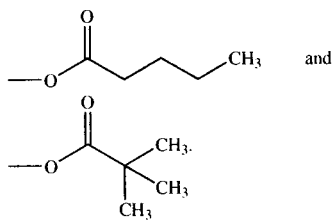

In some embodiments, the compound of Formula I is selected from the group consisting of N-benzyladriamycin-14-valerate (AD 198) and N-benzyladriamycin-14-pivalate (AD 445), represented by the structures:

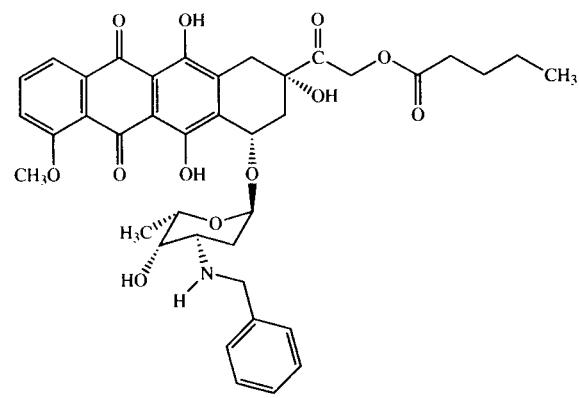

and

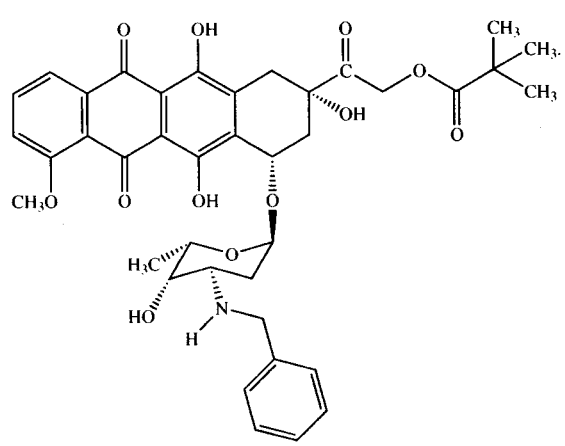

III.B. Pharmaceutically Acceptable Salts

The presently disclosed compounds (e.g. compounds of Formula (I)) can be administered as pharmaceutically acceptable salts. Such pharmaceutically acceptable salts include the gluconate, lactate, acetate, tartarate, citrate, phosphate, maleate, borate, nitrate, sulfate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, as described in more detail herein below, the hydrochloride salt of the presently disclosed amine-containing anthracycline compounds is made by passing hydrogen chloride gas into an anhydrous solution of the free base. Accordingly, in some embodiments, the pharmaceutically acceptable salt is a hydrochloride salt.

III.C. Pharmaceutical Formulations

Anthracycline compounds that are active in the cytoplasm, including the compounds of Formula (I) and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for systemic administration, such as by intravenous, intraarterial, or aerosol administration as discussed in greater detail below. Also, the presently disclosed subject matter provides such active compounds that have been lyophilized and that can be reconstituted to form pharmaceutically acceptable formulations for administration, for example, as by direct instillation into a body cavity, intravenous or intramuscular injection.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. Typically, a dosage from about 0.5 mg/kg to 5 mg/kg can be employed for intramuscular injection. Preferred dosages are 1 μmol/kg to 50 μmol/kg, and more preferably 22 μmol/kg and 33 μmol/kg of the compound for intravenous administration. The duration of the treatment is usually once per day for a period of two to three weeks or until the condition is essentially controlled.

In accordance with the presently disclosed methods, pharmaceutically active compounds as described herein can be administered systemically as a solution, suspension (such as but not limited to a microsuspension), or emulsion (such as but not limited a microemulsion). Alternatively, the compounds or salts also can be administered by direct instillation into a body cavity (such as but not limited to intraperitoneally, intrapleurally, intraventricularly as in the brain, and/or rectally as by suppository), inhalation, intravenously, or intramuscularly as a liposomal suspension. When administered through inhalation the active compound or salt should be in the form of a plurality of solid particles (such as but not limited to microparticles) or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formula (I) described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, polysorbate, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I) or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 1.0 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods of Use

The presently disclosed subject matter provides in some embodiments methods and compositions for inducing apoptosis in a cancer cell. In particular, the presently disclosed subject matter demonstrates that compounds of Formula (I) activate members of the protein kinase C (PKC) family of cellular signaling enzymes in a manner that induces rapid apoptosis through direct mitochondrial interaction, even in cells expressing anti-apoptosis factors. Further, the presently disclosed subject matter demonstrates that compounds of Formula (I) induce the translocation of PKC-δ to the mitochondria of a cell to induce the phosphorylation of mitochondrial proteins, including, but not limited to, PLS3, thereby inducing apoptosis. This mechanism is in contrast to other apoptotic agents, such as $H_2O_2$, UV-radiation, γ-radiation, or other chemotherapeutic agents, including daunorubicin and doxorubicin, which do not activate PKC-δ directly but, rather, inflict cellular damage leading to cell cycle arrest. The extranuclear localization of the anthracyclines described herein largely excludes the contribution of nuclear targets to apoptosis and emphasizes the role of mitochondria in apoptosis.

The structural and functional properties of the compounds of Formula (I) allow circumvention of several clinically relevant mechanisms of multidrug resistance. The structural properties of the compounds of Formula (I) including increased lipophilicity compared with anthracyclines such as daunorubicin and doxorubicin, result in the circumvention of the drug extrusion activity of plasma membrane-localized multidrug transport proteins such as P-glycoprotein (P-gp) and multidrug resistance protein 1 (MRP-1). Additionally, the mechanism of action of the compounds of Formula (I) (i.e. induction of apoptosis in dividing cells through the activation of PKC-δ) results in the circumvention of resistance mechanisms that impede cell cycle arrest and apoptosis, such as found in a variety of solid tumors and leukemias. These mechanisms of resistance include p53 protein dysfunction, Bcl-2 and Bcl-X$_L$ anti-apoptotic protein expression, and transcriptional factor NF-κB expression.

Thus, in some embodiments, the presently disclosed subject matter provides a method for treating a cancer, the method comprising administering to a subject in need of treatment thereof an effective amount of an active compound as described herein. These active compounds, as set forth above, include compounds of Formula (I) and their pharmaceutically acceptable salts. In some embodiments, the administering of an effective amount of a compound of Formula (I) induces the translocation of PKC-δ to the mitochondria of a cancer cell to induce the phosphorylation of a mitochondiral protein, thereby inducing apoptosis in the cancer cell. In some embodiments, the mitochondrial protein is PLS3.

The subject treated in the presently disclosed subject matter in its many embodiments is desirably a human subject, although it is to be understood the methods described herein are effective with respect to all vertebrate species, which are intended to be included in the term "subject." In some embodiments the subject is warm-blooded vertebrate.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos or as pets, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

The apoptosis inducing compounds described herein can provide therapy for a wide variety of tumors and cancers including skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

Thus, cancers that can be treated or prevented by the methods of the present invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Thus, leukemias can include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC--1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia.

An "effective amount" is defined herein in relation to the treatment of cancers is an amount that will decrease, reduce, inhibit, or otherwise abrogate the growth of a cancer cell or tumor. Thus, an "effective amount" is the quantity of compound in which a beneficial clinical outcome is achieved when the compound is administered to a subject with a cancer. A "beneficial clinical outcome" includes, for example, a reduction in tumor mass, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. The precise amount of compound administered also will depend on the degree, severity and type of cancer. The skilled artisan will be able to determine appropriate dosages depending on these and other factors.

The disclosed compounds are administered by any suitable route, including, for example, by parenteral administration. Parenteral administration can include, for example, systemic administration, such as by intramuscular, intravenous, intraarterial, subcutaneous, or intraperitoneal injection. The compounds can also be administered topically, by inhalation (e.g., intrabronchial, intranasal, or intranasal drops), or rectally, depending on the type of cancer to be treated. The compound of Formula (I) can be delivered regionally to a particular affected region or regions of the subject's body. Alternatively, systemic delivery of the compound of Formula (I) can be more appropriate in certain circumstances, for example, where extensive metastasis has occurred.

In addition, it will be appreciated that therapeutic benefits for the treatment of cancer can be realized by combining treatment of an apoptosis inducing compound of Formula (I) with one or more additional anti-cancer agents or treatments. The choice of such combinations will depend on various factors including, but not limited to, the type of disease, the age and general health of the subject, the aggressiveness of disease progression, and the ability of the subject to tolerate the agents that comprise the combination. For example, in cases where tumor progression has reached an advanced state, the apoptosis-inducing agent of Formula (I) can be combined with other agents and therapeutic regimens that are effective at reducing tumor size (e.g., radiation, surgery, chemotherapy, hormonal treatments, and or gene therapy). Additionally, in some embodiments, it can be desirable to combine the compound of Formula (I) with one or more agents that treat the side effects of a disease or the side effects of one of the therapeutic agents, e.g., providing the subject with an analgesic, or agents effective to stimulate the patient's own immune response (e.g., colony stimulating factor).

Thus, a variety of additional therapeutic agents, also described as "antineoplastic agents", "anti-cancer agents", or "chemotherapeutic agents" can be used in combination with one or more of the Formula (I) compounds of the presently described subject matter. Such compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and other telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine α-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine α-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, also can be combined with compounds of the present invention in pharmaceutical compositions. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the compound of Formula (I) of the presently disclosed subject matter to provide a suitable cancer treatment.

Antibodies have also been used as anti-cancer agents. Anti-cancer antibodies may be monoclonal antibodies. Anti-cancer antibodies may be humanized or chimeric antibodies. Antibodies can be conjugated to additional therapeutic agents, for example to a anti-cancer therapeutic. Anti-cancer antibodies include: trastuzumab (HERCEPTIN®, Genentech, Inc., South San Francisco, Calif., United States of America); alemtuzumab (CAMPATH®, Berlex, Inc., Montville, N.J., United States of America); bevacizumab (AVASTIN®, Genentech, Inc., South San Francisco, Calif., United States of America); gemtuzumab (MYLOTARG®, Wyeth-Ayerst, Philadelphia, Pa., United States of America); and cetuximab (ERBITUX®, Merck KGaA, Darmstadt, Germany).

Thus, current chemotherapeutic agents that can be used in a combination treatment with a Formula (I) compound of the presently disclosed subject matter include 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chlorambucil, bisulfan, nitrosurea, dactinomycin, duanorubicin, doxorubicin, bleomycin, plicomycin, tamoxifen, paclitaxel, transplatimun, vinblastin, and methotrexate, monoclonal antibodies, and the like.

Combination treatments involving a Formula (I) compound and one or more additional therapeutic agent, such as another chemotherapeutic agent can be achieved by contacting cells with the Formula (I) compound and the other agent at the same time. Such combination treatments can be achieved by contacting the cell with a single composition or pharmacological formulation that includes both agents, or by contacting the cell with two distinct compositions or formulations, at the same time, wherein one composition includes the Formula (I) compound and the other includes the other agent.

Alternatively, the Formula (I) compound can precede or follow treatment with the other agent by intervals ranging from minutes to weeks. In embodiments where the other agent and the compound of Formula (I) are provided separately to a cell or to a subject, one would generally ensure that a significant period of time did not expire between the time of each delivery, such that the other agent and Formula (I) compound would still be able to exert an advantageously combined effect on the cell. In such instances, it is provided that one would contact the cell with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either the compound of Formula (I) or of the other agent will be desired.

In some embodiments, the presently disclosed subject matter provides a method for treating a drug resistant cancer, the method comprising administering to a subject in need of treatment thereof an effective amount of a compound of Formula (I) as defined hereinabove. In some embodiments, the administering of an effective amount of a compound of Formula (I) induces the translocation of PKC-δ to the mitochondria of a drug resistant cancer cell to induce the phosphorylation of PLS3, thereby inducing apoptosis in a drug resistant cancer cell whose cellular mechanisms for triggering growth arrest and apoptosis are otherwise impaired. In some embodiments, the administering an effective amount of a compound of Formula (I) for treating a drug resistant cancer further provides cardioprotection to the subject in need of treatment thereof. In some embodiments, the drug resistant cancer comprises an adult chronic myeloid leukemia (CML). In some embodiments, the drug resistant leukemia is resistant to imatinib mesylate (commercially available as GLEEVEC® from Novartis Pharmaceuticals Corporation, East Hanover, N.J., United States of America).

In some embodiments, the presently disclosed subject matter provides a method for providing cardioprotection in a subject in need thereof, the method comprising administering to the subject an effective amount of a compound of Formula (I) as defined hereinabove. In some embodiments, the administering to the subject an effective amount of a compound of Formula (I) induces the activation of PKC-ε in a cardiomyocyte, thereby inducing a cardioprotective effect.

In some embodiments, the method comprises administering a therapeutic amount of a compound of Formula (I) in combination with a therapeutic amount of an additional therapeutic agent or combination of agents, wherein the additional therapeutic agent or agents are known to cause cardiac damage. In some embodiments the additional therapeutic agent or combination is used to treat a cancer in a subject in need of treatment thereof. In some embodiments, the additional therapeutic agent is an antimetabolite, an antimicrotubule agent, an alkylating agent, an antibody, or a combination thereof. In some embodiments, the additional therapeutic agent comprises a monoclonal antibody. In some embodiments, the monoclonal antibody comprises trastuzumab (commercially available as HERCEPTIN® from Genentech, Inc., South San Francisco, Calif., United States of America). In some embodiments, the monoclonal antibody is alemtuzumab (CAMPATH®, Genzyme, Cambridge, Mass., United States of America). In some embodiments, the monclonal antibody is bevacizumab (AVASTIN®, Genentech, South San Francisco, Calif., United States of America). In some embodiments, the monoclonal antibody is gemtuzumab (MYLOTARG®, Wyeth-Ayerst, Philadelphia, Pa., United States of America). In some embodiments, the cancer comprises a human epidermal growth factor receptor 2 (HER2) positive breast cancer. In some embodiments, the cancer is selected from a Non-Hodgkins lymphoma, a colorectal cancer, an ovarian cancer, a mesothelioma, an acute myeloid leukemia, and a B-cell chronic lymphocytic leukemia (B-CLL). In some embodiments, the additional therapeutic agent includes more than one anti-cancer agent. In some embodiments, the additional therapeutic agents comprise trastuzumab and cyclophosphamide, trastuzumab and paclitaxel, or bevacizumab and 5-FU. In some embodiments the additional therapeutic agent includes an anthracycline topoisomerase II inhibitor.

The methods and compositions of the presently disclosed subject matter also can be used for the treatment of other diseases or conditions caused by a apoptosis impairment in non-cardiac cells, such as, for example, other hyperproliferative or autoimmune disorders, such as psoriasis, rheumatoid arthritis, other inflammatory diseases and viral infections.

EXAMPLES

The following Examples have been included to illustrate modes of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

The presently disclosed subject matter discloses a class of anthracycline compounds that bind the C1b regulatory domain of PKC, triggering apoptosis in proliferating cells. The Examples describe the cardioprotective action of these compounds in comparison to other, commonly used antineoplastic anthracycline compounds, such as DOX.

Methods and Materials Employed in Examples

DOX was obtained from Sigma Chemicals (St. Louis, Mo., United States of America), while the N-benzyl O-acyl adriamycins are synthesized according to previously described procedures. See U.S. Pat. No. 4,610,977 to Israel. M. and Seshadri, R.; and Lothstein, L., et al., *Anti-cancer Drugs*, 9, 58-66 (1998). For in vitro and ex vivo use, the adriamycin-based compounds were dissolved in dimethylsulfoxide (DMSO) and diluted in the appropriate aqueous media. For in vivo use, DOX was formulated in sterile saline, while AD 198 was formulated in 20% NCI Diluent 12 (polyhydroxylated castor oil:ethyl alcohol, 1:1 by volume)/80% saline.

Example 1

PKC-δ Activation Studies

Cell Culture and Reagents: IL-3-dependent 32D.3 murine myeloid cell lines, transfected with either empty SFFV expression vector (See Boise, L. H., et al., *Cell*, 74, 597-608 (1993)) or SFFV-Bcl-2 (32D.3/Bcl-2), as described in 37, were maintained in RPMI 1640 medium with L-glutamine (Atlanta Biologicals, Norcross, Ga., United States of America) supplemented with 10% fetal bovine serum (Atlanta Biologicals) and 40 U/mL IL-3 (Sigma Chemicals, St. Louis, Mo., United States of America). See also Nip, J., et al., *Mol. Cell Biol.*, 17, 1049-1056 (1997). Rottlerin, benzyloxycarbonyl-Val-Ala-Asp(OMe)-fluoromethylketone (Z-VAD-FMK), cyclosporin A (CsA), betulinic acid, ionophore A23187, 1,2-bis(o-aminophenoxy)ethane-N,N,N',N'-tetraacetic acid tetra(acetoxymethyl) ester (BAPTA-AM) and ethyleneglycol-bis-(2-aminoethyl)-N, N,N',N'-tetraacetic acid (EGTA) were obtained from Calbiochem (La Jolla, Calif., United States of America). All drugs were initially dissolved in DMSO to aid dissolution in the aqueous buffers used. The final maximum DMSO concentration used in drug treatments (2% for 1 hr) is not cytotoxic.

Mitochondrial Membrane Depolarization: 32D.3 cells were treated continuously with either 10 μM rottlerin, or 200 μM Z-VAD-FMK for 5 hr or in combination with AD 198 for 3 hr following 2 hr incubation in inhibitors. Cells were then collected and washed twice in warm phosphate buffered saline (PBS) and prepared for staining with 5,5',6,6'-tetradhloro-1,1',3,3'-tetraethylbenzimidazolyl carbocyanin iodide (DEPSIPHER™; Trevigen, Inc., Gaithersburg, Md., United States of America) according to the manufacturer's instructions. Cellular red fluorescence emissions were observed microscopically (Olympus model BX60, Olympus America Inc., Melville, N.Y., United States of America) using a >620 nm filter.

Immunoblot Analysis of Cytochrome C Release from Mitrochondria: For cytochrome c release into cytosol, cells were treated with drug as described above. After incubation in AD 198, cells were washed in cold PBS, resuspended in mitochondrial isolation buffer (250 mM sucrose, 20 mM HEPES-KO$_4$ pH 7.4, 1.5 mM MgCl$_2$, 10 mM KCl, 1 mM EDTA, 1 mM PMSF, 20 µM leupeptin, 50 µg/mL pepstatin A, 50 µg/mL aprotonin, and 2 mM DTT) and incubated on ice for 20 min. Cells were lysed with a Dounce homogenizer, and the lysate was subjected to centrifugation at 14,200×g for 15 min at 4° C. The resulting supernatant containing the cytosolic fraction was lyophilized, then suspended in RIPA buffer (50 mM Tris-HCl, pH 8.0, 150 mM NaCl, 0.1% SDS, 1% Nonidet P40, 0.5% sodium deoxycholate). Following protein determination of the samples, 100 µg of protein were resolved by SDS-PAGE in 15% polyacrylamide. Immunoblot analysis was performed using anti-cytochrome c antibody (BD Biosciences, San Diego, Calif., United States of America) as previously described. See Barrett, C. M., et al., *Molec. Cancer Therapeutics*, 1, 469-481 (2002).

Cell Viability Determination: 32D.3 cells, at a density of 5×10$^5$/mL, were exposed to the IC$_{90}$ concentration (drug concentration required to kill 90% of 32D.3 cells 72 hr after 1 hr drug treatment; 5 µM) of AD 288 and AD 198 in complete medium for 1 hr at 37° C. in a 5% CO$_2$ humidified environment. Control cells were treated with 1% DMSO for 1 hr. Following drug treatment, cells were washed twice with PBS and incubated further in drug-free media. At the times indicated, 75 µL aliquots of cell suspension were combined with 25 µL trypan blue (Life Technologies, Rockville, Md., United States of America) and assayed microscopically for cellular dye exclusion.

Transcominant-Negative PKC-δ Vector Transfection and Kinase Activity Assay: 32D.3 cells were stably transfected by electroporation with either non-recombinant pCEV expression vector or PKC-δ K376R trans-doninant negative PKC-δ (a gift from Dr. Weiqun Li, Georgetown University, Washington, D.C., United States of America). See Li, W., et al., *J. Biol. Chem.*, 270, 8311-8318 (1995). Transfected clones were selected by limited dilution cloning, in which cells are diluted to one cell per 5 mm cell culture well, and assessed for changes in PKC-δ activity by measuring kinase activity of calcium-independent PKC towards the PKC pseudo-substrate peptide (Upstate Biotechnology, Lake Placid, N.Y., United States of America). See Roaten, J. B., et al., *Molec. Cancer Therapeutics*, 1, 483-492 (2002); and Roaten, J. B., et al., *J. Med. Chem.*, 44, 1028-1034 (2001). Kinase-specific activity was calculated by subtracting basal activity from total catalytic activity and expressed as fmol phosphate/min/mg. See Roaten, J. B., et al., *J. Med. Chem.*, 44, 1028-1034 (2001).

Example 2

Results of PKC-δ Activation Studies

AD 198 induces rapid apoptosis in 32D.3 murine myeloid cells, with less than 20% of the initial cell population remaining viable within 12 hr after 1 hr exposure to 5 µM AD 198. See FIG. 1A. The PKC inhibitor, rottlerin, at a concentration that selectively inhibits PKC-δ activity (10 µM; see Gschwendt, M., et al., *Biochem., Biophys. Res. Commun.*, 199, 93-98 (1994)) decreases cell sensitivity to AD 198, increasing cell viability to approximately 80% 12 hr after drug exposure and from 8% to 50% 24 hr after drug exposure.

Figure 1B:
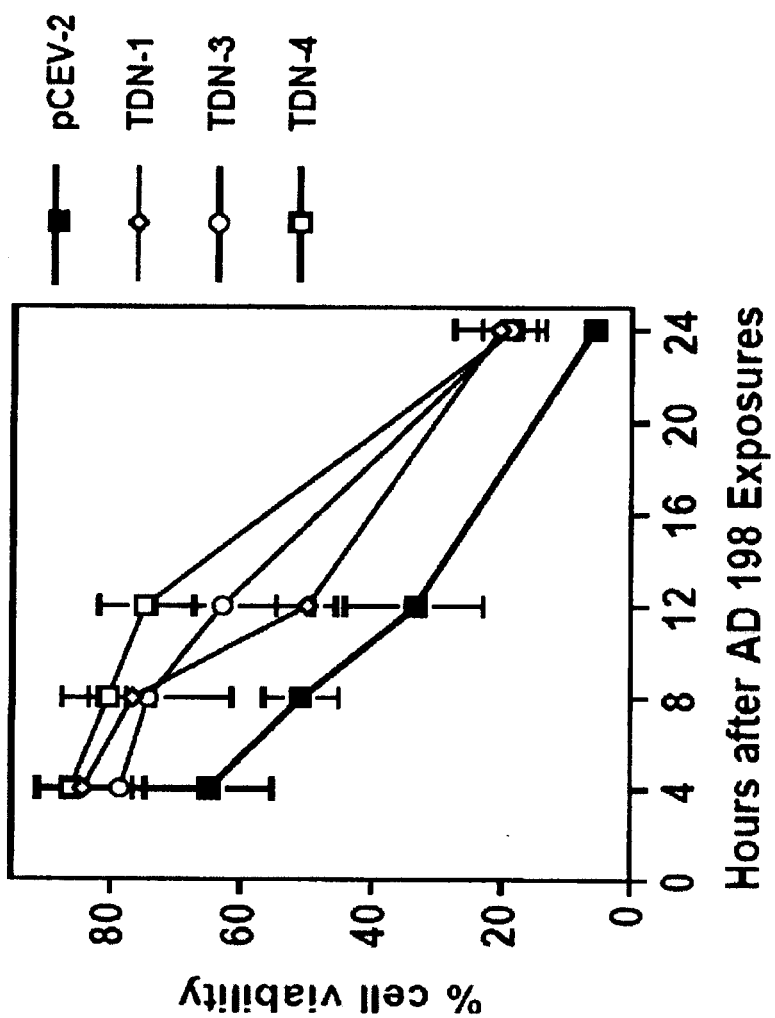
FIG. 1B is a graph showing the percent viability of transfected 32D.3 cells as measured by trypan blue staining at 4 hr, 8 hr, 12 hr, and 24 hr after 1 hr treatment with 5 μM AD 198. The cells were transfected with either pCEV empty expression vector (solid squares) or a pCEV/TDN-PKCδ vector expressing the trans-dominant negative PKC-δ isoform (open diamonds for TDN-1 vector, open circles for TDN-3 vector, and open squares for TDN-4 vector). Each data point represents the mean of at least three independent determinations, each consisting of 300-500 cells per count.

Previous reports have suggested that rottlerin can have mitochondrial effects that occur independently of PKC-δ. See Soltoff, S. P., *J. Biol. Chem.*, 276, 37986-37992 (2001). Thus, in order to confirm that specific inhibition of PKC-δ activity decreases 32D.3 sensitivity to AD 198, 32D.3 cells were transfected with the PKC-δ K376R transdominant negative PKC-δ expression vector. As shown in Table 1 below, a representative clone, TDN-4, exhibits Ca$^+$-independent PKC activity that is reduced by 42% relative to control cells transfected with non-recombinant vector (pCEV-2). Reduced PKC activity corresponds to a delay in 50% cell kill from 8 hr to 18 hr after AD 198 treatment. See FIG. 1B. In contrast, reduced PKC activity had no apparent effect on AD 288 cytotoxicity. Together with the previous studies using an array of PKC inhibitors, these results indicate that PKC-δ activity is required for AD 198-mediated cell kill. (See Lothstein, L., et al., *Anti-Cancer Drugs.*, In Press (2006); He, Y., et al., *Cancer Res.*, 65, 10016-10023 (2005)).

TABLE 1

PKC-δ Activity in Transfected Cells.

| | Activity (fmol phosphate/min/mg) | % Control |
|---|---|---|
| PCEV-2 | 17.83 | 100.0 |
| TDN-4 | 10.40 | 58.3 |

Figure 2:
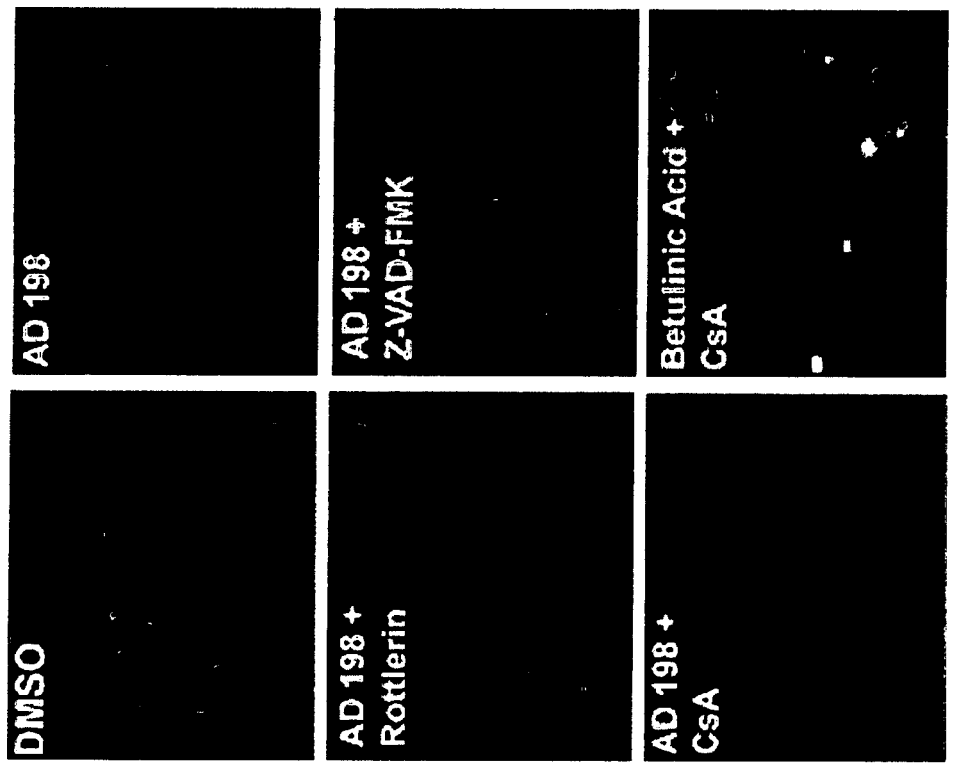
FIG. 2 shows photomicrographs of 32D.3 cells treated with either DMSO, 5 μM AD 198, 5 μM AD 198 and 10 μM rottlerin, 5 μM AD 198 and 200 μM Z-VAD-FMK, or 5 μM AD 198 and 5 μM CsA for three hours, followed by staining with DEPSIPHER™ (Trevigen, Inc., Gaithersburg, Md., United States of America) for 20 min and observation by fluorescence microscopy. An additional group of cells were treated with 15 μg/mL betulinic acid for 5 hr or 5 μM CsA for 1 hr followed by a combination of 5 μM CsA and 15 μg/mL betulinic acid for 5 hr. Cellular fluorescence distribution was observed by epifluorescence microscopy. The photomicrographs are representative of at least 3 independent determinations.

The mitochondria seem a likely target for AD 198, as it has been previously shown that the mitochondria of untreated 32D.3 cells contain PKC-δ. See Barrett, C. M., et al., *Molec. Cancer Therapeutics*, 1, 469-481 (2002). Therefore, the effects of PKC-δ inhibition on AD 198-induced mitochondrial membrane depolarization were assessed. FIG. 2 shows the status of mitochondrial membrane potential ($\Delta\psi_m$) by staining with DEPSIPHER™, a fluorescent cationic dye which dimerizes within polarized mitochondria to yield a punctate red pattern, as shown in control (DMSO-treated) cells. Treatment of cells with 5 µM AD 198 for 3 hr diminishes punctate fluorescence and induces cell shrinkage in approximately 75% of the observed cells. Combined exposure of cells with 10 µM rottlerin and 5 µM AD 198 preserves punctate fluorescence, indicating the preservation of mitochondrial membrane potential through PKC-δ inhibition. Competition with ATP binding (see Gschwendt, M., et al., *Biochem. Biophys. Res. Commun.*, 199, 93-98 (1994)) allows rottlerin to inhibit the activity of both PKC-δ holoenzyme and the constitutively active 40 kDa catalytic subunit release by caspase-3 during apoptosis. To determine whether AD 198-induced $\Delta\psi_m$ is mediated through holoenzyme activation or results less directly from caspase mediated cleavage of PKC-δ, 32D.3 cells were treated with 5.0 µM AD 198 in combination with the pan-caspase inhibitor Z-FAD-FMK under conditions (200 µM; 3 hr) known to inhibit PKC-δ cleavage. See Barrett, C. M., et al., *Molec. Cancer Therapeutics*, 1, 469-481 (2002). As shown in FIG. 2, inhibition of PKC-δ cleavage by Z-VAD-FMK fails to inhibit AD 198-induced $\Delta\psi_m$ as indicated by the loss of punctate fluorescence along with cell shrinkage. These results suggest that AD 198 activates PKC-δ holoenzyme to achieve mitochondrial depolarization. (See Lothstein, L., et al., *Anti-Cancer Drugs.*, In Press (2006); He, Y., et al., *Cancer Res.*, 65, 10016-10023 (2005)).

AD 198-mediated depolarization is not blocked by the expression of Bcl-2 or Bcl-X$_L$. See Barrett, C. M. et al., *Molec. Cancer Therapeutics*, 1, 469-481 (2002); and Bilyeu, J. D., et al., *Mol. Pharmacol.*, 65, 1-10 (2004). One inhibitory function of the anti-apoptotic Bcl-2 proteins is prevention of mitochondrial permeability transition pore complex (PTPC) formation and activation. See Costantini, P., et al., *J. Natl. Cancer Inst.*, 92, 1042-1053 (2000). Therefore, the ability of AD 198 to trigger $\Delta\psi_m$ despite inhibition of PTPC activation was also assessed. Cyclosporine A (CsA) has been shown to bind to cyclophilin D and inhibit both $\Delta\psi_m$ and cytochrome c release induced by a wide variety of stimuli. See Crompton, M., *Biochem. J.*, 341, 233-249 (1999); and Andre, N., et al., *Cancer Res.*, 60, 5349-5353 (2000). Treatment of 32D.3 cells with 5 µM CsA for 4 hr had no effect on $\Delta\psi_m$. Betulinic acid, a novel antitumor agent that induces apoptosis through direct interaction with mitochondria (see Fulda, S., et al., *J. Biol. Chem.*, 273, 33942-33948 (1998)) induces $\Delta\psi_m$ in a manner that is inhibited by CsA treatment, as shown by the preservation of punctate fluorescence. 5 µM CsA, however, does not inhibit AD 198-induced $\Delta\psi_m$.

Figure 3A:
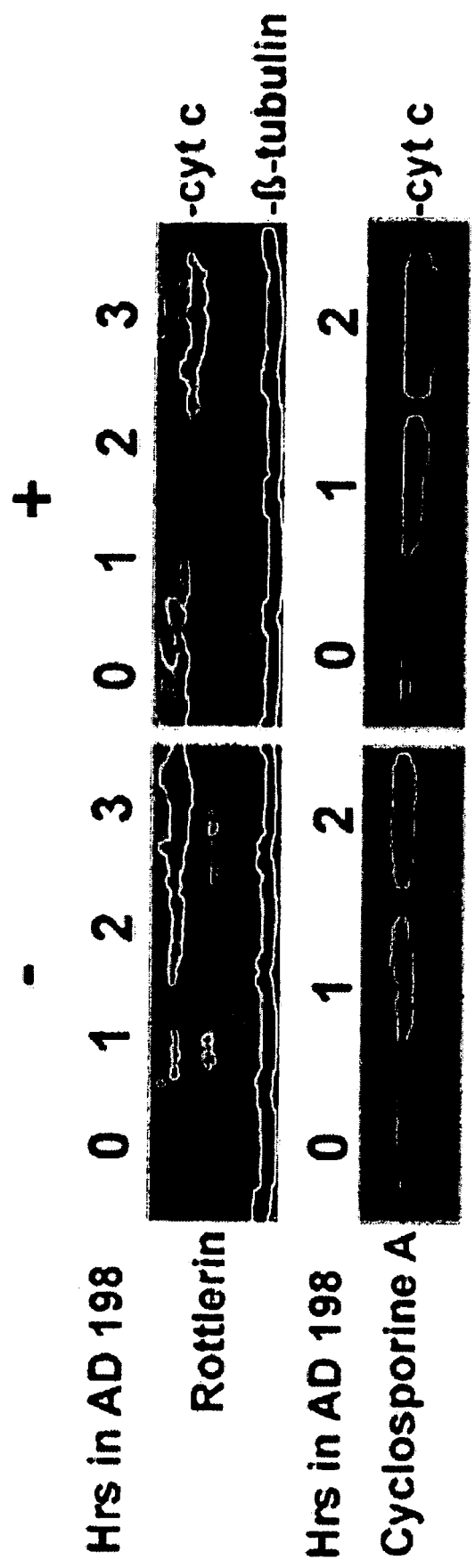
FIG. 3A shows immunoblots representing cytochrome c release in 32D.3 cells exposed to 5 μM AD 198 in the presence (+) or absence (−) of either 10 μM rottlerin or 5 μM CsA for the indicated times. The cells were fractionated to isolate the cytosolic fraction, which underwent SDS-PAGE and transfer to nitrocellulose. The nitrocellulose filters were treated with anti-cytochrome c monoclonal antibody (1:250) for 2 hr, followed by 1 hr treatment with 1:1000 dilution of goat anti-mouse-HRP-conjugated second antibody. Proteins were detected by chemiluminescence.
Figure 3B:
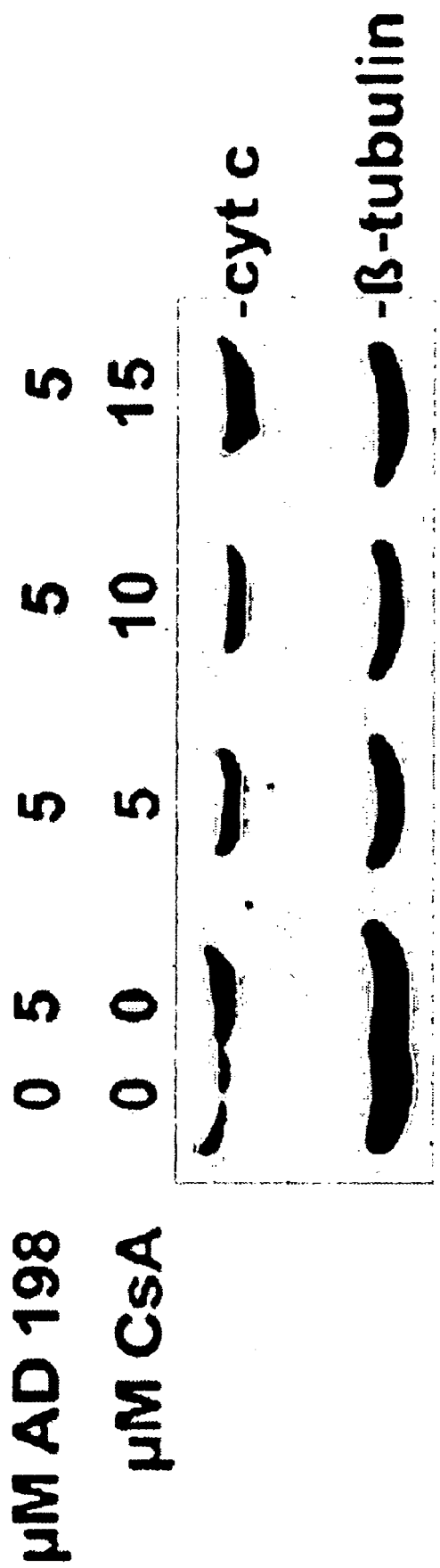
FIG. 3B shows the immunoblots of 32D.3 cells treated with either 5 μM AD 198, alone, or in combination with 5, 10, or 15 μM CsA as indicated above the immunoblots, followed by combined treatment with CsA and AD 198 for 2 hr. Cytosolic fractions were analyzed for cytochrome c content as described for FIG. 3A. The immunoblots are representative of at least 3 independent analyses.

The release of cytochrome c often coincides with $\Delta\psi_m$ and is an essential component for caspase-3 activation. See Costantini, P., et al., *J. Natl. Cancer Inst.*, 92, 1042-1053 (2000). AD 198 treatment of 32D.3 cells results in the rapid release of cytochrome, detectable by immunoblot analysis of cytosolic fractions after 2 hr of drug exposure. See FIG. 3A. Combined treatment of cells with AD 198 and 10 µM rottlerin inhibits cytochrome c release. However, 5 µM cyclosporine A treatment in combination with AD 198 did not inhibit cytochrome c release. Further, increasing concentrations of CsA up to 15 µM failed to inhibit cytochrome c release by AD 198. See FIG. 3B. These results indicate that AD 198-mediated cytochrome c release requires PKC-δ activation, but does not require PTPC formation and opening. (See Lothstein. L., et al., *Anti-Cancer Drugs.*, In Press (2006); He, Y., et al., *Cancer Res.*, 65, 10016-10023 (2005)).

Figure 4A:
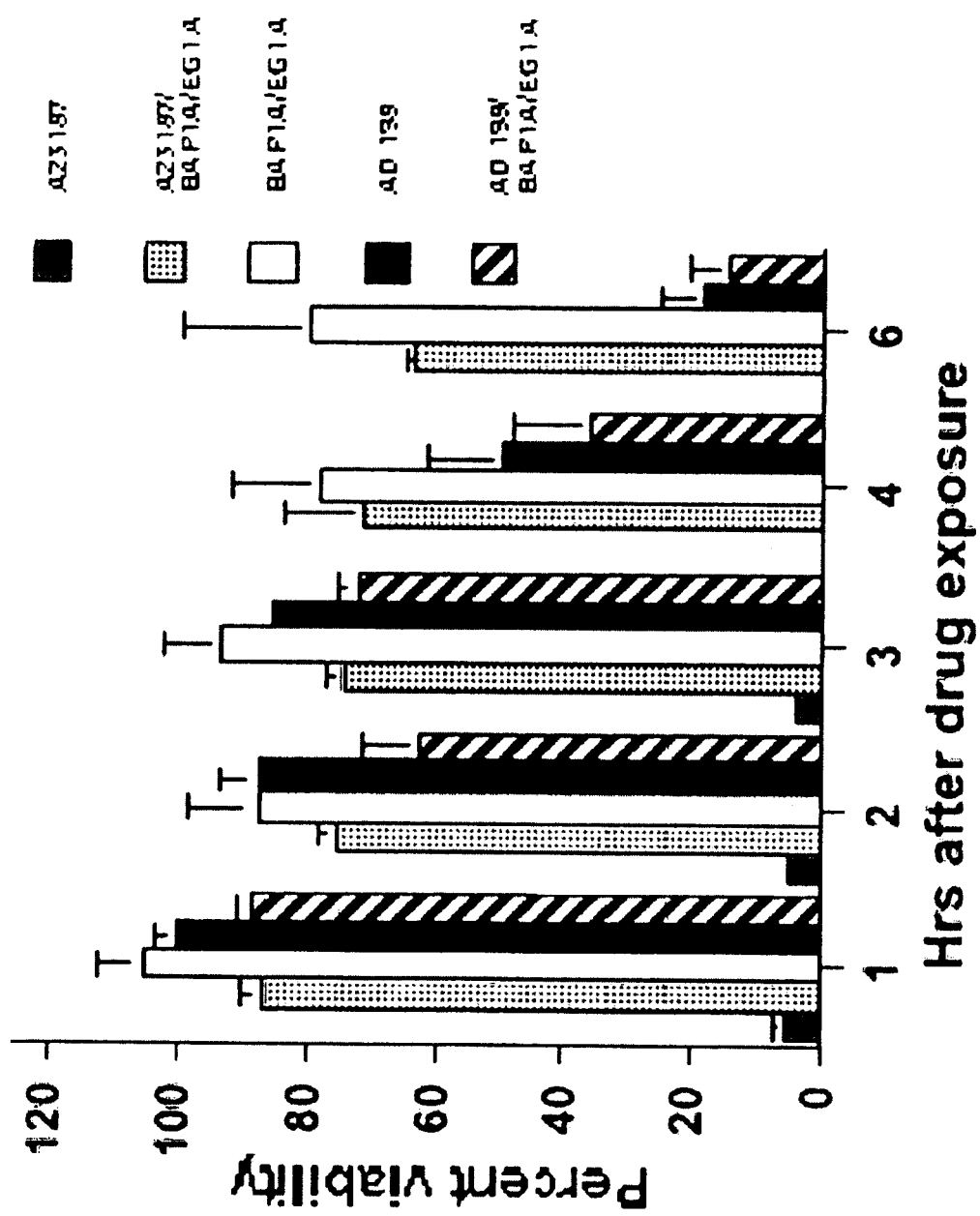
FIG. 4A shows a bar graph of cell viability following AD 198 drug treatment with and without $Ca^{2+}$ chelation. As indicated by the legend, 32D.3 cells were treated with either 5 μM AD 198 (solid bars) or 10 μM of the $Ca^{2+}$ ionophore A23187 (shaded bars) for 1 hr, then incubated in drug-free medium for the times specified. Alternatively, cells were treated with a mixture of $Ca^{2+}$ chelators, 25 μM BAPTA-AM/3 μM EGTA (open bars), or with 25 μM BAPTA-AM/3 μM EGTA for 1 hr prior to and during exposure to 5 μM AD 198 (striped bars) or with 25 μM BAPTA-AM/3 μM EGTA for 1 hr prior to and during exposure to 10 μM A23187 (stippled bars) followed by incubation in drug-free medium for the times indicated. Cell viability was monitored by trypan blue staining. Results are the mean of three independent determinations.
Figure 4B:
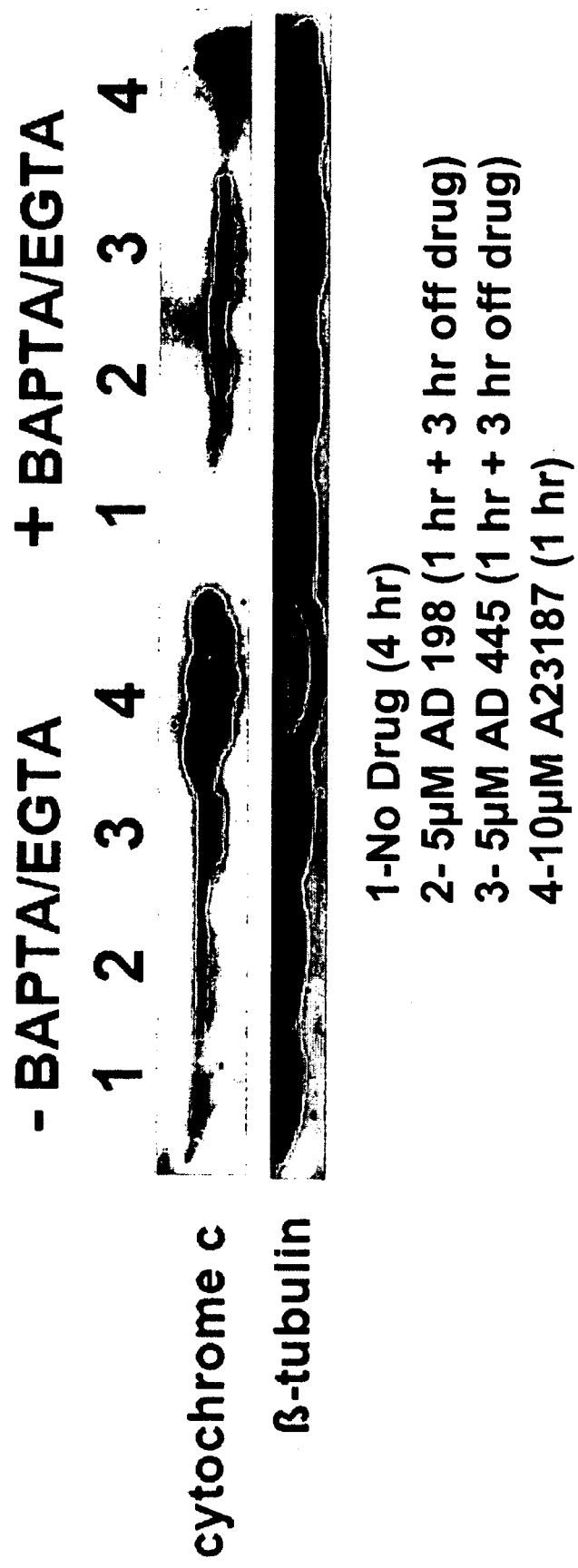
FIG. 4B shows the immunoblot analysis of cytochrome c release in cells treated with or without the $Ca^{2+}$ chelators BAPTA-AM and EGTA. As indicated by the legend, cells were also treated with 5 μM AD 198, 5 μM AD 445 or 10 μM A23187. Cytochrome c release was determined as described for FIG. 3A. The four lanes on the left were not treated with BAPTA-AM and EGTA (−BAPTA/EGTA). The four lanes on the right were treated with BAPTA-AM and EGTA (+BAPTA/EGTA). The two lanes marked 1 correspond to cells treated with no drug, the lanes marked 2 to cells treated with 5 μM AD 198 for 1 hour and then incubated in a drug free medium for 3 hr, the lanes marked 3 to cells treated with 5 μM AD 445 for 1 hr and then incubated in a drug free medium for 3 hr, and the lanes marked 4 to cells treated with 10 μM A23187 for 1 hr.

The independence of AD 198-mediated $\Delta\psi_m$ and cytochrome c release from PRPC status suggests that $Ca^{2+}$ uptake triggers $\Delta\psi_m$ through alternate micochondrial transport. See O'Rourke, B., *J. Physiol.*, 529, 23-36 (2000); Mukherjee, S. B. et al., *J. Biol. Chem.*, 277, 24717-24727 (2002); and Buntinas, L., et al., *Biochim. Biophys. Acta.*, 1504, 248-261 (2001). An alternative possibility is that $Ca^{2+}$ uptake does not play a role in AD 198-mediated mitochondrial responses. Intra- and extracellular $Ca^{2+}$ were chelated with BAPTA-AM and EGTA, respectively, prior to AD 198 treatment to determine whether AD 198-mediated cell kill is $Ca^{2+}$-dependent in 32D.3 cells. See FIG. 4A. The $Ca^{2+}$ ionophore A23187 induces >90% cell kill within 1 hr of treatment of 32D.3 cells. BAPTA-AM/EGTA treatment inhibited A23187 cytotoxicity, with less than 15% cell kill after 6 hr beyond that observed with BAPTA/EGTA alone, indicating effective $Ca^{2+}$ chelation. Under these conditions, the rate of AD 198-mediated cell kill was unaffected by $Ca^{2+}$ chelation. Further, BAPTA/EGTA treatment blocked cytochrome c release induced by A23187, but failed to block release by AD 198 or the closely related AD 445. See FIG. 4B. These results suggest that AD 198-induced apoptosis does not require cellular $Ca^{2+}$ flux. (See Lothstein, L., et al., *Anti-Cancer Drugs.*, In Press (2006); He, Y., et al., *Cancer Res.*, 65, 10016-10023 (2005)).

Example 3

PLS3 Phosphorylation Studies

Materials: The cDNA encoding full length PLS3 (See, Strausberg, R. L. et al., *Proc. Natl. Acad. Sci. U.S.A.* 99; 16899-16903 (2002)) was cloned into the QIAEXPRESS™ pQE30 vector (Qiagen, Inc., Valencia, Calif., United States of America) to construct PLS3 tagged with 6 consecutive histidine residues (6×His tag) at the N-terminus (pQE-PLS3). A point mutant PLS3(T21A) was generated using the QUIKCHANGE® Site-Directed Mutagenesis Kit (Stratagene, La Jolla, Calif., United States of America). As there were two serine residues generated at the cloning region of pQE30, one before and one after the consecutive histidine residues, these two serine residues were mutated to alanine to abrogate possible false phosphorylation. Mammalian expression vectors for His-tagged PLS3 and PLS3(T21A) were constructed with pCMV vector. Mammalian expression vectors for wild-type (pHA-PKC-δ) and kinase-defective PKC-δ (pHA-PKC-δ KD, K376R) were kindly provided by Dr. Jae-Won Soh (Herbert Irving Comprehensive Cancer Center, Columbia University, New York, N.Y., United States of America). Mammalian PKC-δ small interfering RNA (siRNA) expression plasmid (pKD-PKC-δ-v3) was from Upstate (Lake Placid, N.Y., United States of America). The polyclonal antibody to PLS3 was raised in rabbits against full-length recombinant PLS3 (Proteintech Group, Inc., Chicago, Ill., United States of America). The first 50 amino-acid fragment of PLS3 was made as His-tagged protein similar to full-length PLS3. The monoclonal antibody PKC-δ was obtained from BD Biosciences (Palo Alto, Calif., United States of America). Monoclonal antibodies to phosphothreonine (PT) and β-actin were obtained from Sigma-Aldrich Chemicals (St. Louis, Mo., United States of America). The polyclonal antibody to voltage-dependent anion channel was obtained from Affinity BioReagents (Golden, Colo., United States of America). Secondary anti-mouse or anti-rabbit antibodies conjugated horseradish peroxidase, as well as protein A Sepharose beads were obtained from Amersham Pharmacia Biotech (Piscataway, N.J., United States of America). Recombinant human PKC-δ enzyme was purchased from Calbiochem Biosciences (La Jolla, Calif., United States of America). [γ-$^{32}$P]ATP was from Life and Analytical Sciences (Boston, Mass., United States of America). The siRNA against PLS3 and a random sequence siRNA were from Qiagen (Valencia, Calif., United States of America). Z-VAD-FMK was from ICN Pharmaceuticals, Inc. (Aurora, Ohio, United States of America) and CsA was from Sigma-Aldrich (St. Louis, Mo., United States of America). MITOTRAKER® Green was from Molecular Probes, Inc. (Eugene, Oreg., United States of America). Cell culture and transfection reagents and media were purchased from Invitrogen Corporation (Carlsbad, Calif., United States of America).

Cell Culture, Transfection, and Treatment: HeLa cells were cultured in Dulbecco's modified Eagle's medium (DMEM) containing 10% fetal bovine serum, 2 mM L-glutamate and penicillin (100 units/mL)-streptomycin (100 µg/mL) at 37° C. in a humidified 5% $CO_2$ atmosphere. HeLa cells at 90% confluence were transfected with different mammalian expression vectors using LIPOFECTAMIN™ 2000 transfection reagent according to the manufacturer's protocol (Invitrogen Corporation, Carlsbad, Calif., United States of America). At 24 hr or 48 hr after transfection, cells were treated with 1:100 dilution of AD 198 that was dissolved in DMSO. For down-regulation of PLS3, HeLa cells at 50% confluence were transfected with siRNA against PLS3 or a scrambled control. Forty-eight hours later, cells were treated with AD 198 for 16 h and harvested for flow cytometry. The whole cell lysate was extracted for analysis with Western blotting.

Expression and purification of Recombinant Proteins: *E. COLI* strain M15 [pREP4] containing the pQE-PLS3 or PLS3 (T21A) plasmid was used to generate recombinant His-tagged PLS3 proteins after induction with 1 mM isopropyl-β-thiogalactoside (IPTG). Bacteria were lysed in a buffer containing 100 mM NaH$_2$PO$_4$, 10 mM Tris-HCl, 8 M urea, pH 8.0 and His-tagged proteins were purified on nickel-nitrilotriacetic acid affinity beads (Ni-beads) and washed extensively with the same buffer at pH 6.3. Bound proteins were eluted in the same buffer (pH 4.5) as described by the manufacturer (Qiagen, Valencia, Calif., United States of America). The purity of the protein was examined by gel electrophoresis, followed by Coomassie blue staining.

Purification of His-tagged Proteins from Transfected HeLa Cells: After washing with ice-cold PBS, HeLa cells transfected with the pCMV-PLS3 or PLS3(T21A) vector were incubated in lysis buffer (50 mM NaH$_2$PO$_4$, 500 mM NaCl, 20 mM imidazole, 1% Triton X-100, 20 mM 2-mercaptoethanol, pH 8.0) for 5 min and sonicated briefly on ice. The lysates were centrifuged at 10,000×g for 10 min at 4° C. The supernatant was saved. Protein concentrations of the supernatants were measured with the Bio-Rad protein assay (Bio-Rad Laboratories, Hercules, Calif., United States of America) and each sample was adjusted to the same concentration. The supernatants, now adjusted to contain the same concentration of protein, were incubated with Ni-beads on a shaker for 2 h at 4° C. Beads were then pelleted at 800×g for 2 min at 4° C. and washed with ice-cold wash buffer (50 mM NaH$_2$PO$_4$, 500 mM NaCl, 20 mM imidazole, 1% Triton X-100, pH 8.0) five times. After washing, the beads were resuspended in SDS buffer and analyzed by Western blotting.

Preparation of Whole Cell Lysates and Subcellular Fractionation: HeLa cells were washed with ice-cold PBS, lysed in ice-cold lysis buffer (50 mM Tris-HCl, pH 7.4, 100 mM NaCl, 1% Triton X-100, 1 mM EDTA, and 1 mM phenylmethylsulfonyl fluoride) for 5 min and sonicated briefly on ice. Cell lysates were centrifuged at 10,000×g for 10 min at 4° C. The supernatants were saved as the whole cell lysates and used for further immunoprecipitation or added into the SDS sample buffer for Western blotting. Subcellular fractionation was done as described previously. See Liu, J. et al., *Cancer Res.*, 63, 1153-1156 (2003).

Western Blot analysis: Equal amounts of protein were analyzed by 10% SDS-PAGE and electrotransferred to Immobilon-P membranes (Millipore Corporation, Bedford, Mass., United States of America). Monoclonal PKC-δ, phosphothreonine, and β-actin antibodies and polyclonal PLS3 antibody were used at 1:1,000 dilution and polyclonal PLS3 antibody was used at 1:2,000 dilution for immunoblotting. Secondary anti-mouse or anti-rabbit antibodies conjugated to horseradish peroxidase were used at 1:2,000 dilution and incubated with the membranes for 1 hr at room temperature. After washing 3 times with TBS/T (1×TBS and 0.1% Tween-20), the blots were developed with enhanced chemiluminescence (ECL) reagents (Pierce; Rockford, Ill., United States of America).

Immunoprecipitation: Whole cell lysates were incubated with 1.25 µg/mL PKC-δ antibody at 4° C. for 2 h and then incubated with protein G Sepharose beads for an additional 2 h. After extensive washing with radioimmunoprecipitation (RIPA) buffer (20 mM Tris-HCl, pH 8.0, 1% NP-40, 0.2% deoxycholate, 120 mM NaCl), the pellets were resuspended in SDS sample buffer and subjected to Western blotting.

Analysis of Apoptotic Cells by Flow Cytometry and Determination of the Transmembrane Potential in Mitochondria: Cell death was quantified by TUNEL (Terminal Deoxynucleotidyltransferase-mediated dUTP-biotin Nick End Labeling; Roche Diagnostics, Basel, Switzerland) or propidium iodide (PI) staining, followed by flow cytometry. For TUNEL staining, HeLa cells were fixed with 1% paraformaldehyde for 15 min on ice and 70% ethanol for 1 h at −20° C. After washing with ice-cold PBS containing 0.125% BSA, cells were incubated in 50 µL of enzyme solution (350 µL dH$_2$O, 100 µL TDT buffer, 50 µL CoCl$_2$, 10 µL dUTP, 2 µL TDT enzyme) at 37° C. for 30 min and 100 µL of staining buffer (20 mL 20×SCC, 8 mL dH$_2$O, 10 µL Triton X-100, 0.5 g nonfat dry milk, 500 µL staining buffer, 1.25 µL avidin-FITC) at room temperature for 30 min. The fluorescence intensity was analyzed by FACScan (BD Biosciences, San Jose, Calif., United States of America). For PI staining, HeLa cells were fixed in 0.5 mL cold 70% ethanol at −20° C. overnight. Cell pellet was resuspended in 300 µL of PBS containing 0.025 mg/mL PI, 0.05% Triton X-100, 0.1 mg/mL RNase A and incubated at room temperature for 30 min. The DNA content per nucleus was evaluated by FACScan. For mitochondrial potential analysis, HeLa cells were incubated with MITOTRACKER® Green at 37° C. for 20 min. The cells were collected and washed with PBS and analyzed by FACScan.

In Vitro Phosphorylation Assay: In vitro phosphorylation was performed in a total volume of 60 µL of reaction mixture. Recombinant protein was diluted to less than 0.2 M urea immediately before phosphorylation assays. Reaction mixtures containing 0.1 µg recombinant human PKC-δ enzyme, 20 mM HEPES buffer (pH 7.4), 4 mM MnCl$_2$, 50 µM ATP, 20 µCi [α-$^{32}$P]ATP, and 1 µg of recombinant PLS3 protein. The reaction mixture was incubated at room temperature for 20 min and terminated by adding 20 µL of 4×SDS sample buffer. The phosphorylated products were separated by SDS-PAGE, electrotransferred to IMMOBILON-P membranes, and exposed by autoradiography.

Example 4

Results of PLS3 Phosphorylation Studies

Figure 5A:
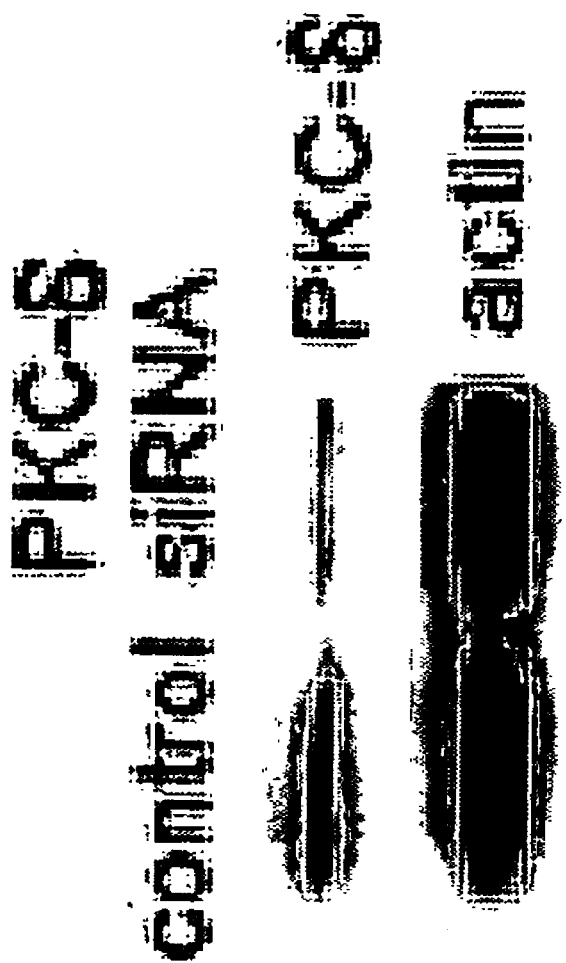
FIG. 5A shows an immunoblot analysis of PKC-δ down-regulation caused by transfection of HeLa cells with mammalian PKC-δ siRNA expression plasmid pKD-PKC-δ-v3. Whole cell lysates were harvested at 48 hr post transfection for Western blotting.
Figure 5B:
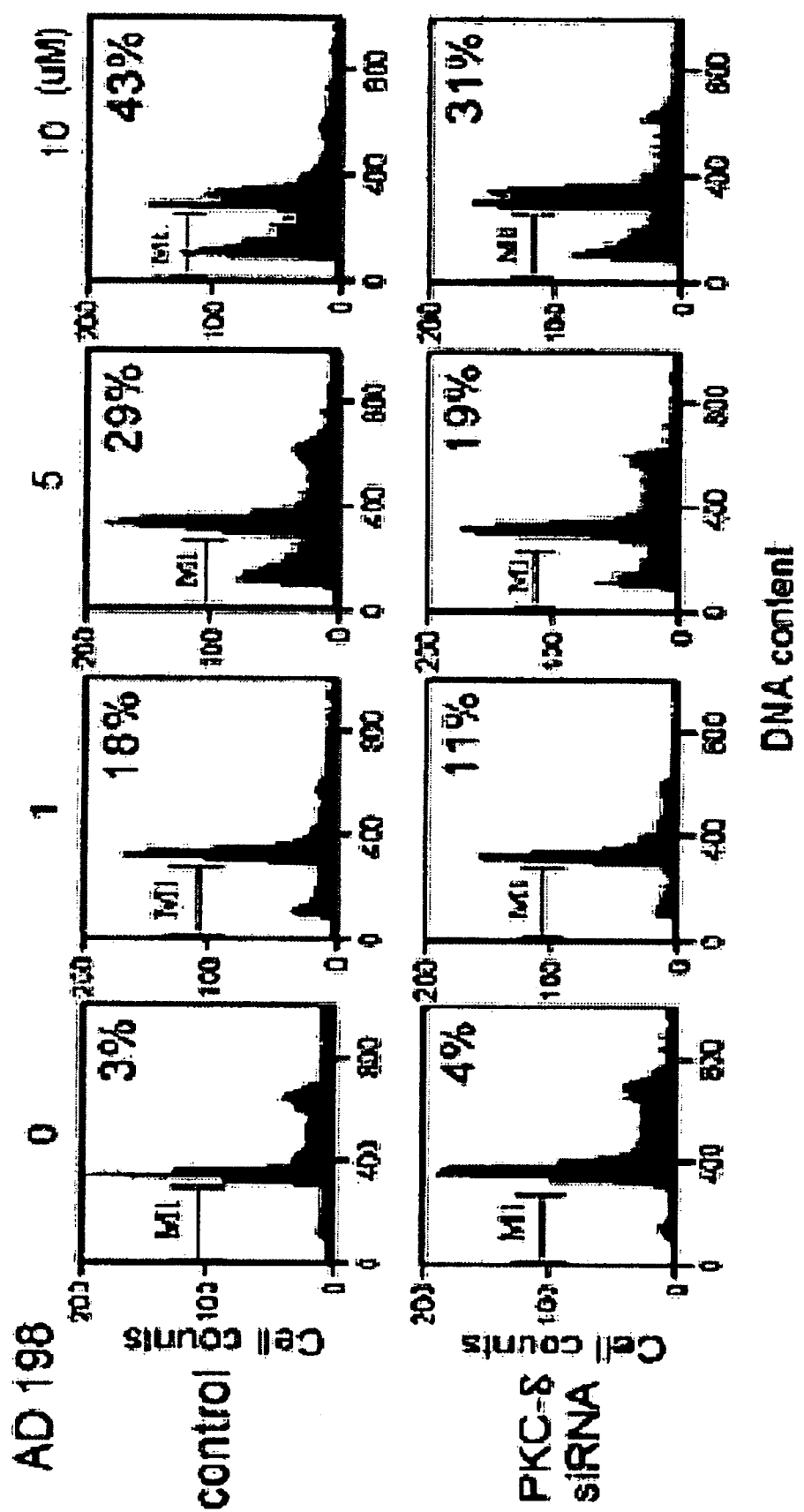
FIG. 5B shows fluorescence emission graphs of AD 198-δ-induced apoptosis in HeLa cells transfected with either mammalian PKC-δ siRNA plasmid pKD-PKC-δ-v3 or a control vector. The cells at 90% confluence were transfected with the vector for 48 hr. Then, cells were treated with AD 198 at 0, 1, 5, and 10 µM for 16 hours. After the cells were harvested, the apoptotic population was determined by propidium iodide staining. The sub-$G_1$ population is marked by M1 gate and used to represent the apoptotic population.
Figure 5C:
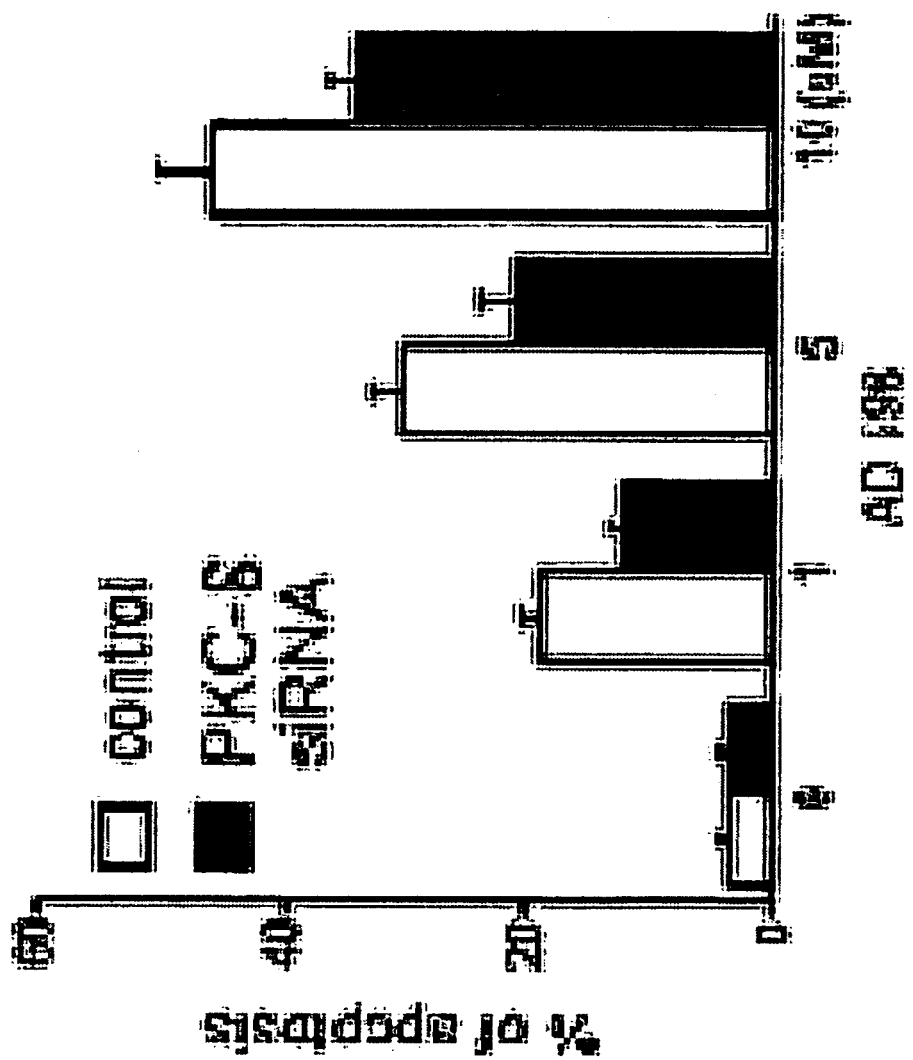
FIG. 5C is a bar graph showing the percent apoptosis induced by the indicated doses of AD 198 in HeLa control cells (open bars) versus HeLa cells transfected with the PKC-δ siRNA expression plasmid (solid bars) as described for FIG. 5B. Data represent the mean from three independent experiments with the standard deviation (SD) as indicated.

To determine whether AD 198-induced apoptosis is suppressed by the down-regulation of PKC-δ, HeLa cells were transfected with pKD-PKC-δ-v3 plasmid, which expresses PKC-δ siRNA to down-regulate PKC-δ. See FIG. 5A. Cells were treated with AD 198 at 0, 1, 5, and 10 µM for 16 hr. As shown in FIGS. 5B and 5C, at all concentrations of AD 198, less apoptosis was detected when PKC-δ was downregulated, confirming that AD 198 apoptosis is PKC-δ dependent.

To assess whether PLS3 was involved in PKC-δ dependent, AD 198-induced apoptosis, HeLa cells were transfected with the vector to overexpress wild-type PLS3. See FIG. 6A. Cells were then treated with various concentrations of AD 198 for 16 h. At three different doses of AD 198, HeLa cells with overexpression of PLS3 were more sensitive to AD 198-induced apoptosis than those without PLS3 overexpression, indicating that overexpression of PLS3 sensitized HeLa cells to AD 198-induced apoptosis. See FIGS. 6B-6C.

Figure 6A:
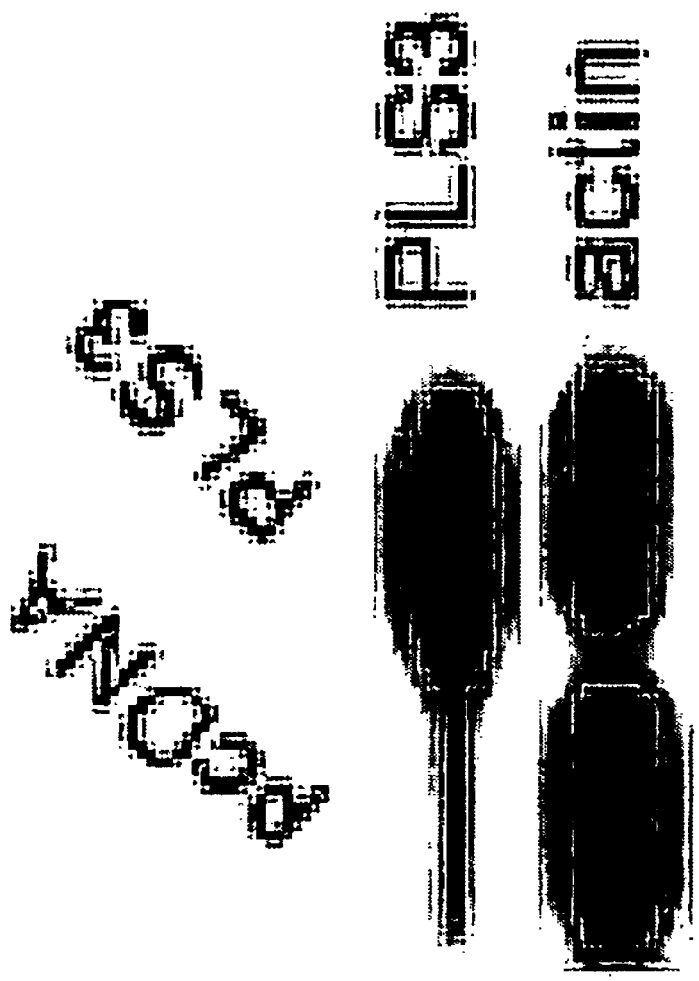
FIG. 6A is an immunoblot showing PLS3 expression in HeLa cells at 90% confluence transfected with either a pcDNA control vector or a PLS3 expression vector for 24 hours.
Figure 6B:
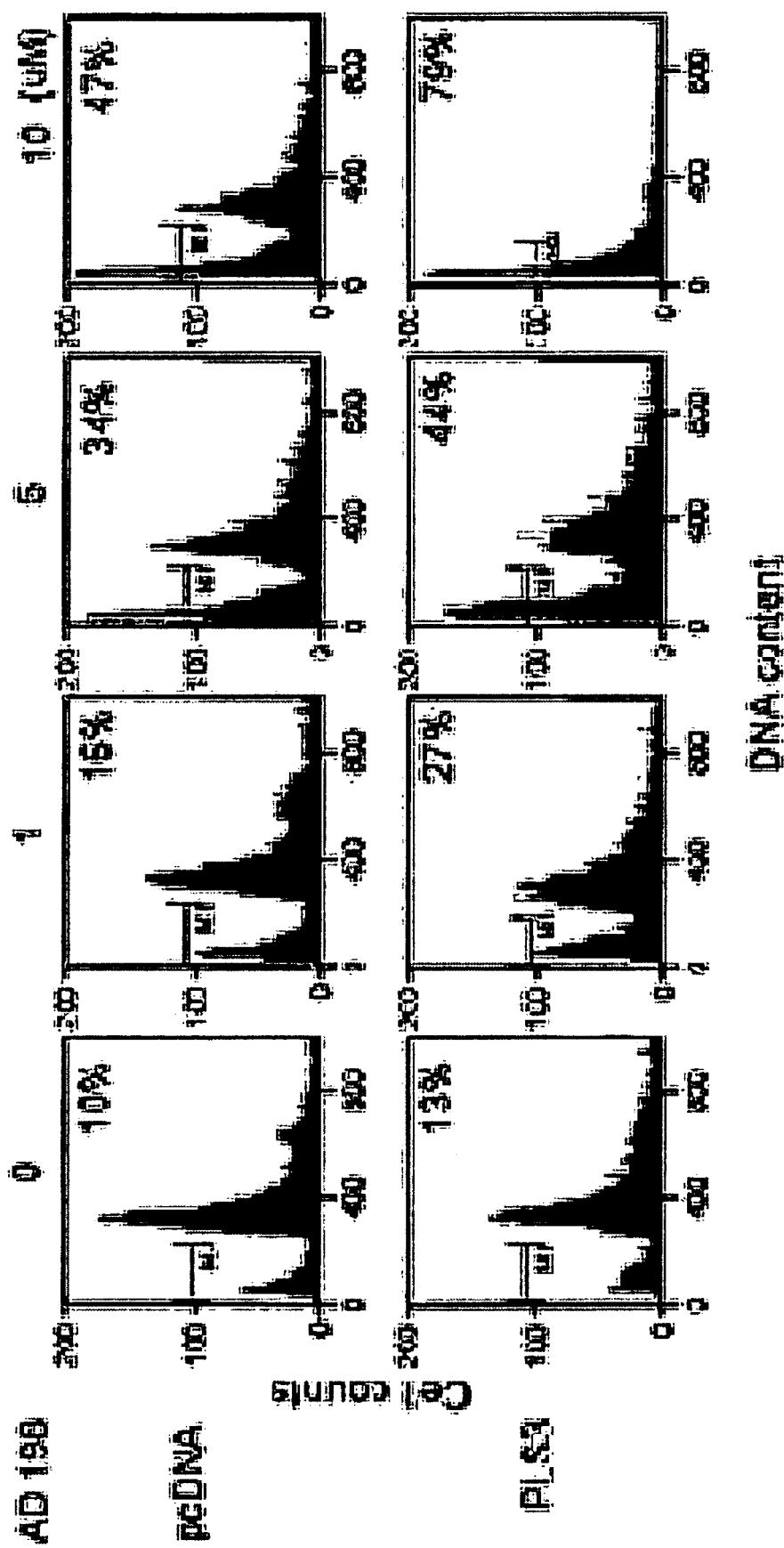
FIG. 6B shows fluorescence emission graphs of AD 198-induced apoptosis in control cells (pcDNA) and in cells over-expressing PLS3. HeLa cells transfected as described for FIG. 6A were incubated with AD 198 at 0, 1, 5, and 10 µM. Cells were harvested at 16 hr after AD 198 exposure and the apoptotic population determined by staining with propidium iodide. The sub-$G_1$ population was marked by M1 gate and used to represent the apoptotic population.
Figure 6C:
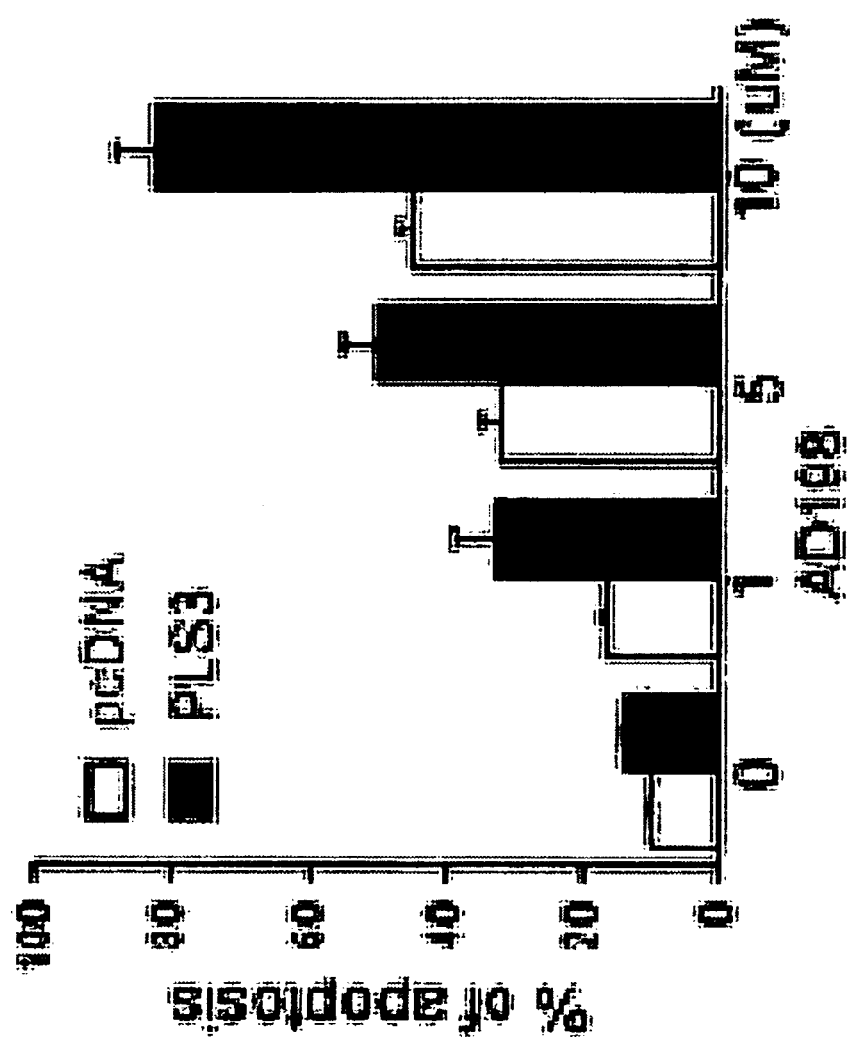
FIG. 6C is a bar graph showing the effect of PLS3 overexpression on AD 198-induced apoptosis. Cells were transfected with either a pcDNA control vector (open bars) or a PLS3 vector (solid bars) as described for FIG. 6A, treated with 0, 1, 5, or 10 µM AD 198 as indicated, and apoptosis was measured as described for FIG. 6B. Data represent the mean percent apoptosis in three independent analyses with the SD as indicated.
Figure 6D:
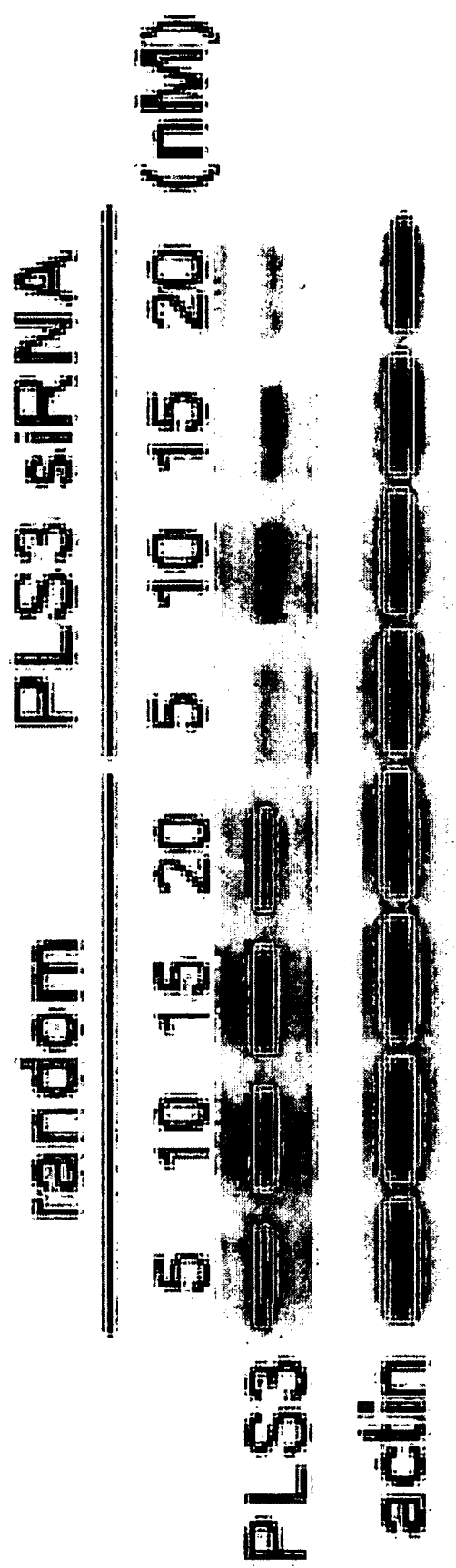
FIG. 6D is an immunoblot showing the down-regulation of PLS3 by siRNA. HeLa-PLS3 cells were transfected with siRNA against PLS3 or random control siRNA at 5, 10, 15, and 20 nM. Whole cell lysates were harvested after 48 hr for Western blotting.
Figure 6E:
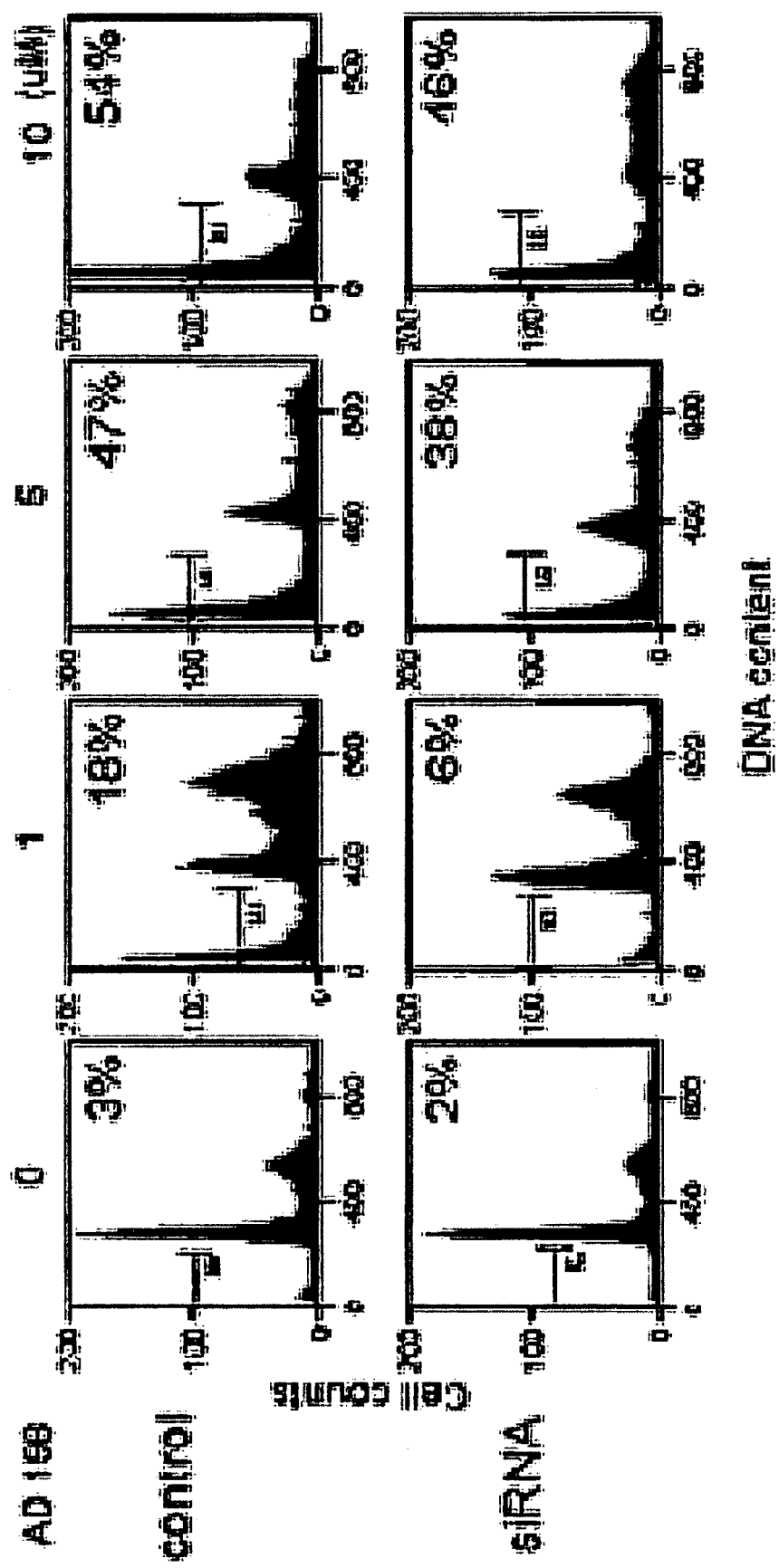
FIG. 6E are fluorescence emission graphs showing how the down-regulation of PLS3 affects AD 198-induced apoptosis. HeLa cells at 50% confluence were transfected with 20 nM siRNA against PLS3 or a random control siRNA for 48 hr. Cells were then treated with AD 198 at 0, 1, 5, and 10 µM for 16 hr followed by staining with propidium iodide. The apoptotic sub-$G_1$ population is marked by M1 gate and the percentage apoptosis is as indicated.
Figure 6F:
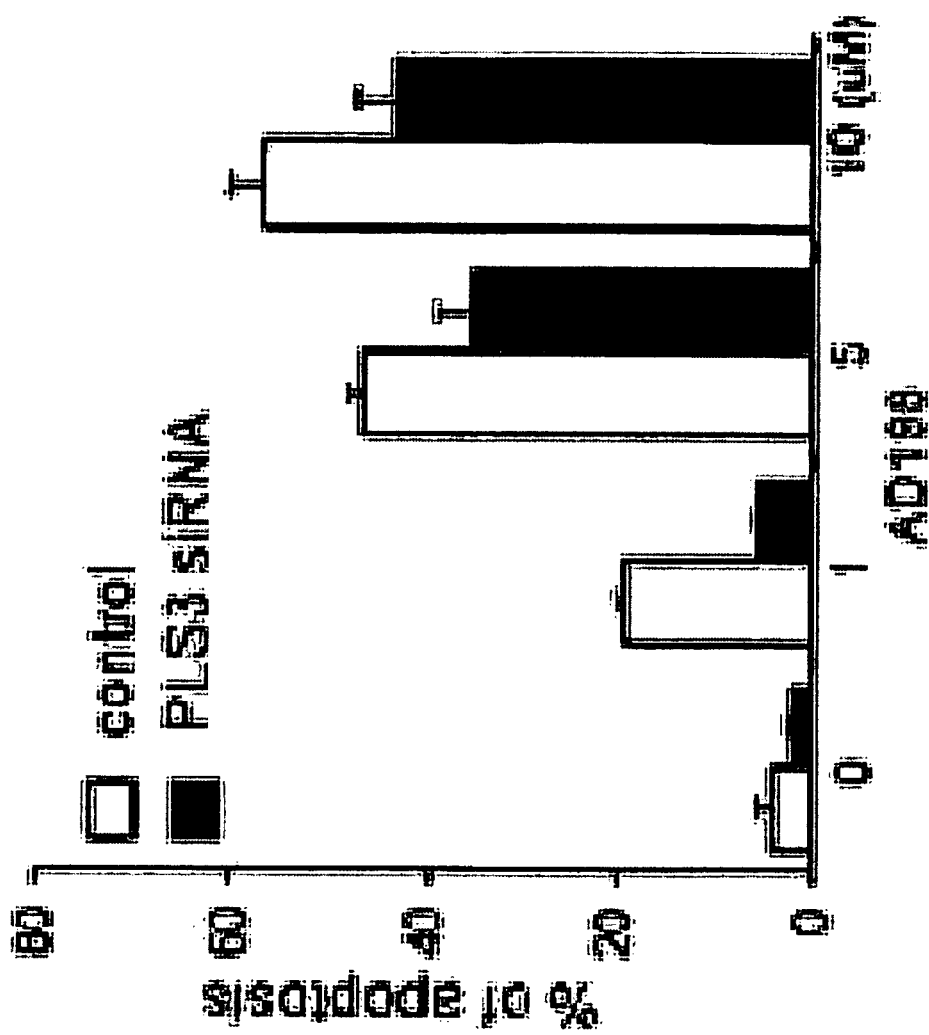
FIG. 6F is a bar graph showing the affect of PLS3 down-regulation on AD 198-induced apoptosis. Cells were treated and apoptosis measured as described for FIG. 6E. Cells transfected with siRNA against PLS3 are shown with the solid bars, and cells transfected with random control siRNA are shown by the open bars. Data represent the mean and SD of three independent determinations.

FIG. 6D shows how down-regulation of PLS3 by increasing amounts of siRNA against affects AD 198-induced apoptosis. Flow cytometry analysis demonstrates that apoptosis in HeLa cells transfected with siRNA against PLS3 was suppressed compared with HeLa cells transfected with scrambled siRNA control. See FIGS. 6E-6F. This result provides further evidence that AD 198-induced apoptosis is mediated by a PLS3-dependent pathway.

Figure 7A:
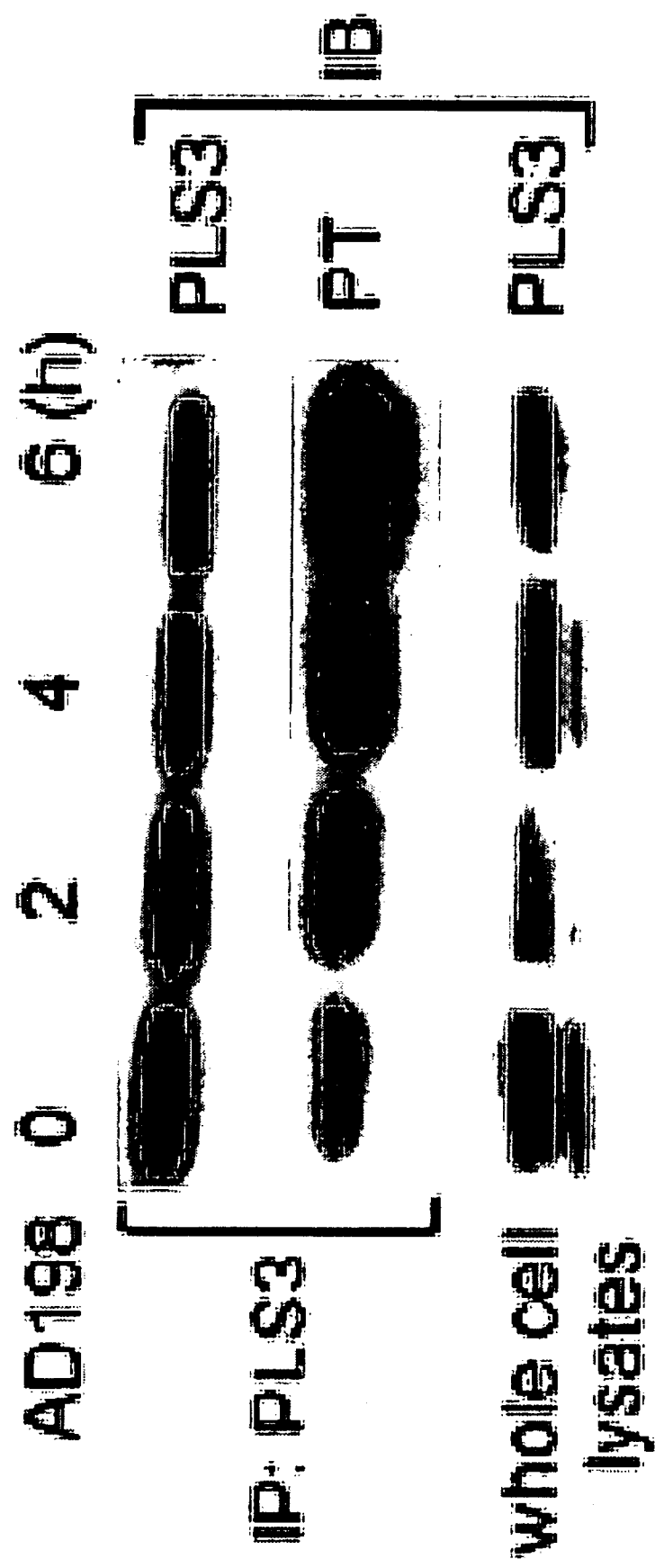
FIG. 7A is an immunoblot showing AD 198 induction of PLS3 phosphorylation at threonine. HeLa cells were transfected with the His-tagged PLS3 expression vector and treated with AD 198 for 0, 2, 4, and 6 hr. Whole cell lysates were incubated with Ni affinity beads to pull down His-tagged PLS3. The pulldown samples were analyzed by Western blotting with antibodies against phosphothreonine and PLS3.
Figure 7B:
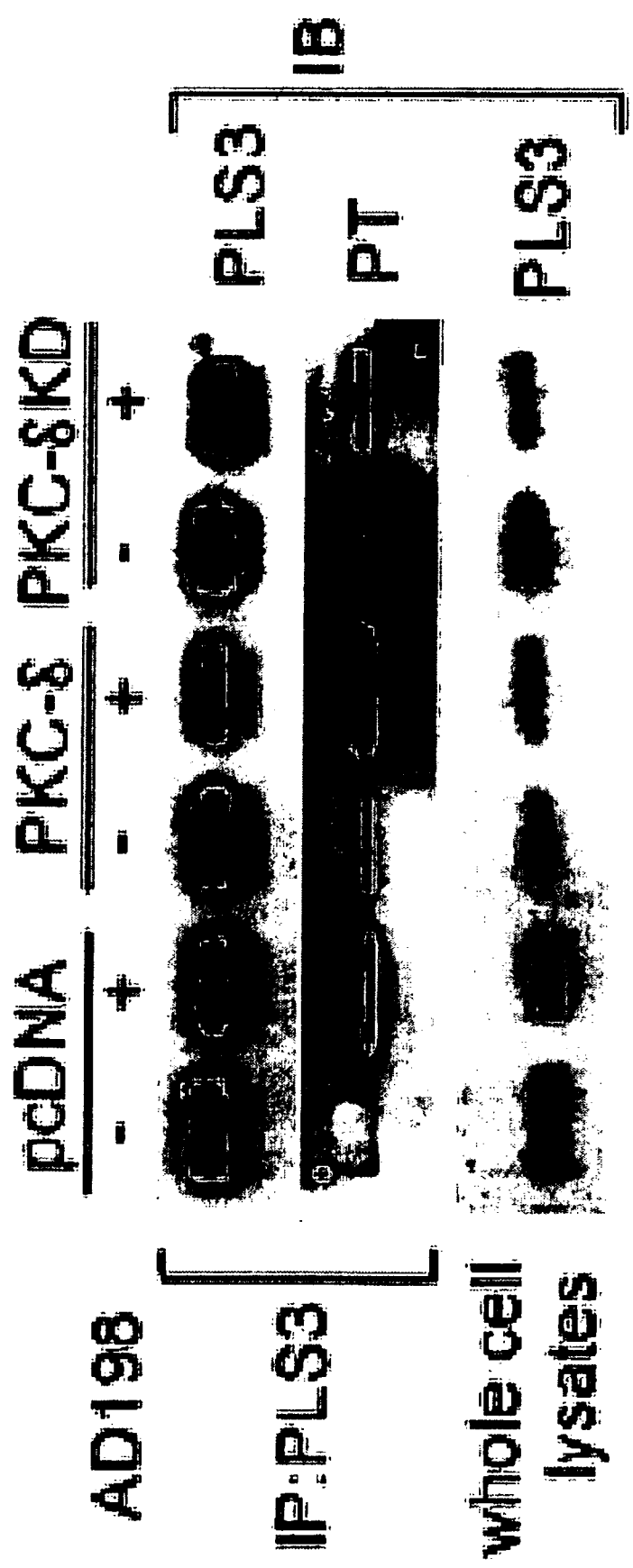
FIG. 7B is an immunoblot comparing AD 198-induced PLS3 phosphorylation by cells expressing PKC-δ and cells expressing kinase-defective PKC-δKD. HeLa cells were transfected with the His-tagged PLS3 combined with the pcDNA empty vector, PKC-δ, or PKC-δKD. Cells were incubated with (+) or without (−) AD 198 (5 µM) for 2 hr. Whole cell lysates were incubated with Ni beads to pull down His-tagged PLS3, and analyzed with antibodies against phosphothreonine and PLS3.
Figure 7C:
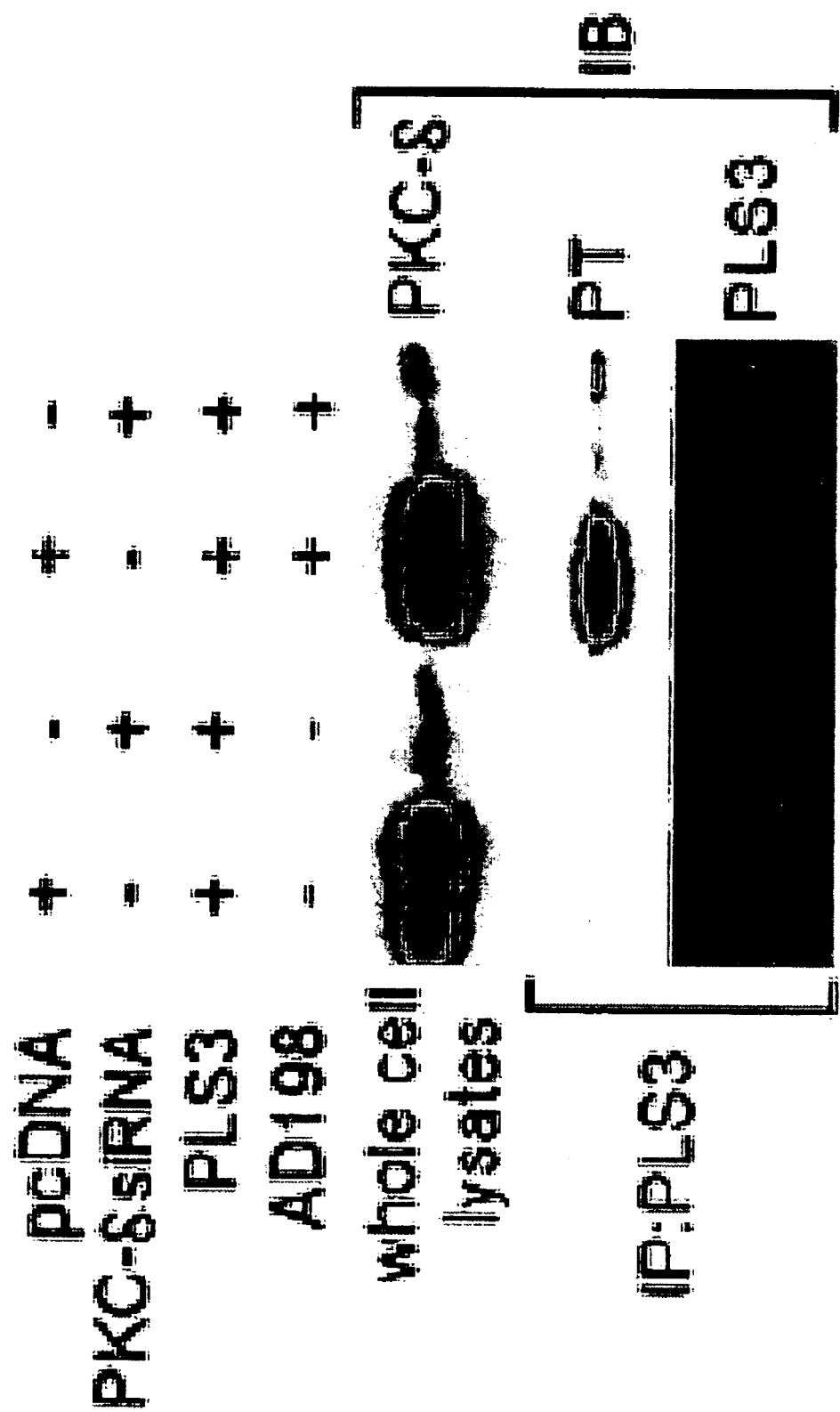
FIG. 7C is an immunoblot showing the affects of down-regulation of PKC-δ on AD 198-induced PLS3 phosphorylation. HeLa cells were transfected with various combinations of pcDNA, pKD-PKC-δ-v3 and pCMV-His-PLS3 as indicated by the (+) and (−) symbols. Cells were treated with (+) or without (−) AD 198 for 16 hr. Whole cell lysates were probed with PKC-δ antibody and PLS3 pulled down by Ni beads was probed with phosphothreonine antibody.

It has been previously demonstrated that UV treatment can induce the translocation of PKC-δ to mitochondria and the phosphorylation of PLS3. See Liu, J., et al., *Cancer Res.*, 63, 1153-1156 (2003). It also has been shown that phosphorylated PLS3 can be recognized by the anti-PT antibody, but not by the anti-phosphoserine antibody. See Liu, J., et al., *Cancer Res.*, 63, 1153-1156 (2003). To investigate whether AD 198 induces PLS3 phosphorylation by activating PKC-δ, a mammalian expression vector for His-tagged PLS3 was constructed. HeLa cells were transfected with the His-tagged PLS3 vector and treated with AD 198 for 0, 2, 4, and 6 h. His-tagged PLS3 was pulled down with Ni-beads and phosphorylation of PLS3 was evaluated by Western blotting using the PT antibody. In control cells, there was a basal phosphorylation of PLS 3 at threonine, and threonine phosphorylation steadily increased after AD 198 induction for at least 6 h. See FIG. 7A. The same method of Ni-bead pull-down was then used to examine the effect of PKC-δ overexpression. His-tagged PLS3 along with PKC-δ or kinase-defective PKC-δ KD were co-transfected into HeLa cells, and then the cells were treated with AD 198. Probing His-tagged PLS3 with the PT antibody confirmed that AD 198 treatment enhanced PLS3 phosphorylation at theonine, and that overexpression of PKC-δ further enhanced this process but not the kinase-defective PKC-δ. See FIG. 7B. The presence of PLS3 phosphorylation in cells transfected with kinase-defective PKC-δ indicated that the endogenous PKC-δ was not completely suppressed. When PKC-δ was down-regulated by siRNA, phosphorylation of PLS3 at threonine after AD 198 treatment is also suppressed. See FIG. 7C. These results indicate that PKC-δ is the kinase activated by AD 198 to induce PLS3 phsophorylation.

Figure 8A:
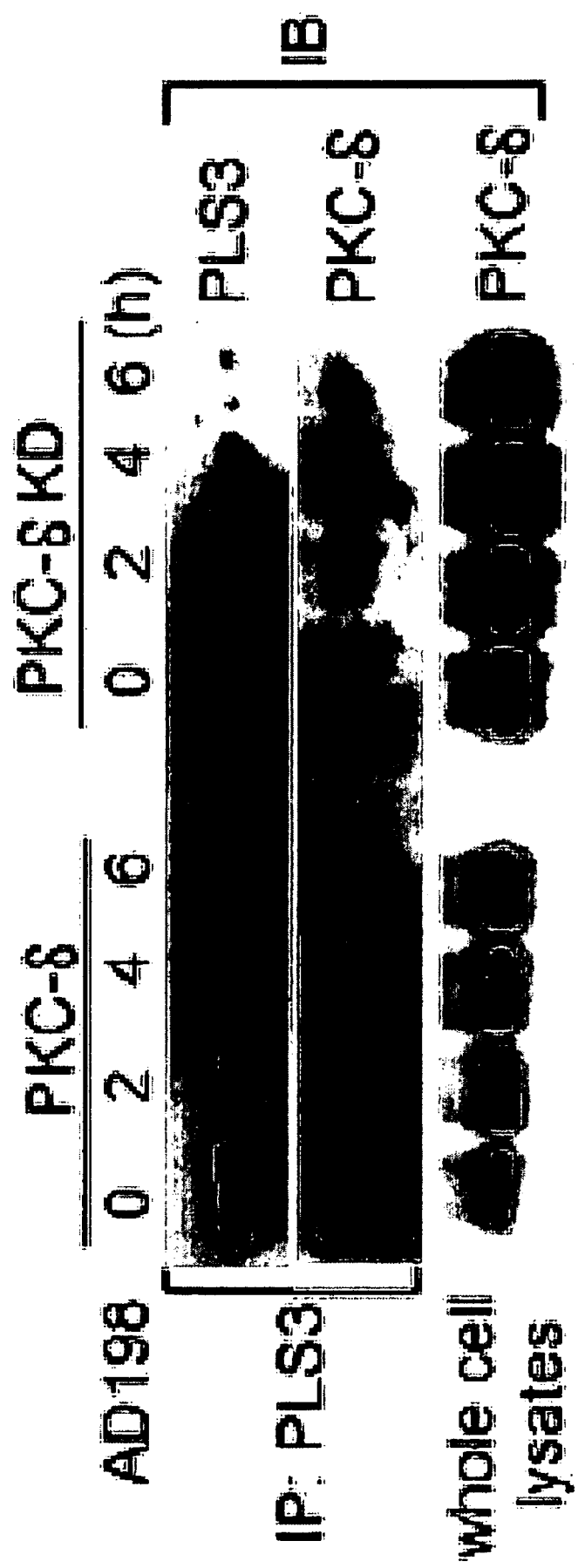
FIG. 8A is an immunoblot showing the interaction of PLS3 with wild-type PKC-δ and with the inactive kinase-defective PKC-δ mutant. HeLa cells expressing His-tagged PLS3 were transfected with PKC-δ or kinase-defective PKC-δ vectors. The cells were then incubated with AD 198 for 0, 2, 4, and 6 hr. Whole cell lysates were incubated with Ni beads to pull down His-tagged PLS3 and probed with antibodies against PLS3 and PKC-δ.
Figure 8B:
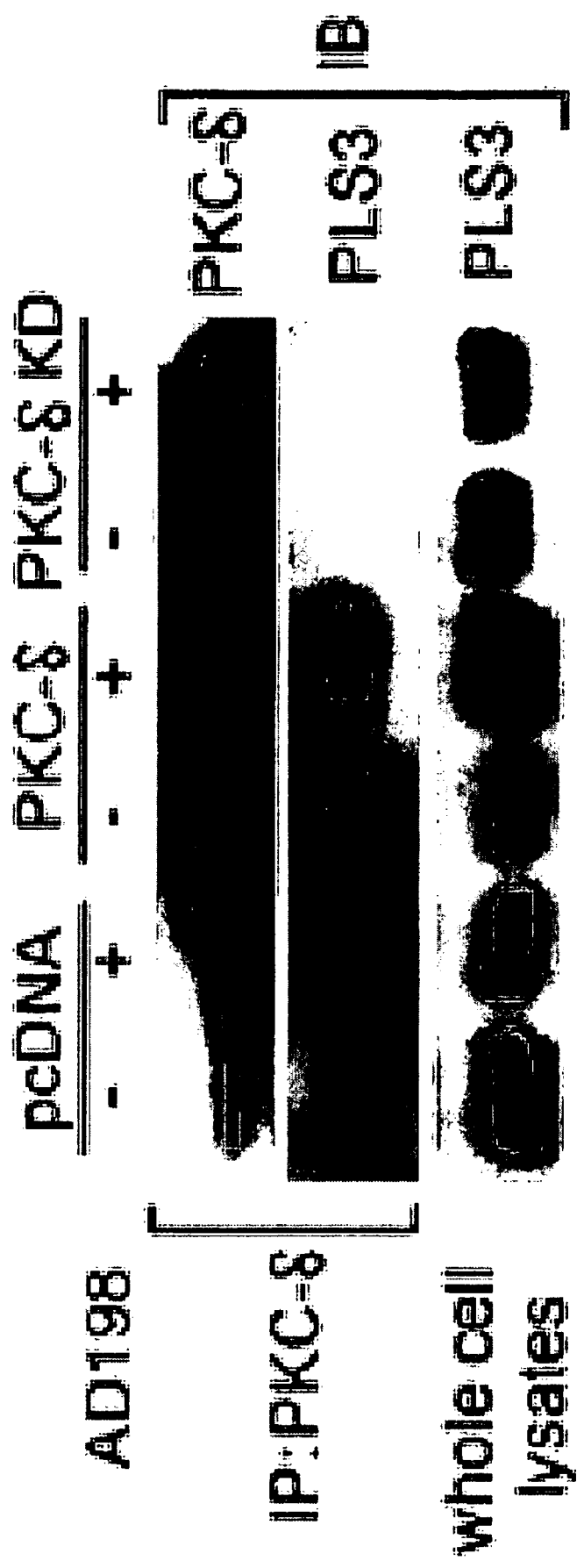
FIG. 8B is an immunoblot showing PLS3 interaction with PKC-δ. HeLa-PLS3 cells transfected with pcDNA, PKC-δ, or kinase-defective PKC-δ vectors were harvested before (−) and 2 hr after (+) AD 198 treatment. PKC-δ was immunoprecipitated from whole cell lysates and analyzed with antibodies against PKC-δ and PLS3. Western blotting of whole cell lysates revealed that the level of PLS3 expression was roughly similar before and after AD 198 treatment.

Examination of the interaction between PLS3 and PKC-δ after AD 198 treatment using Western blotting shows that PKC-δ was pulled down with PLS3 in cells co-transfected with PKC-δ. However, the interaction between PLS3 and PKC-δ KD was much weaker and did not increase after AD 198 treatment. See FIG. 8A. Similar results were obtained by immunoprecipitation of PKC-δ. In control cells, immunoprecipitates of endogenous PKC-δ contained PLS3, which increased after cells were treated with AD 198. Overexpression of PKC-δ increased the amount of PLS3 in the immunoprecipitate of PKC-δ regardless of AD 198 treatment. See FIG. 8B. These studies, combined with the results from Ni-bead pull-down confirmed the association between PLS3 and PKC-δ. No interaction between PLS3 and PKC-δ was seen in PKC-δ KD-transfected HeLa cells.

Figure 9A:
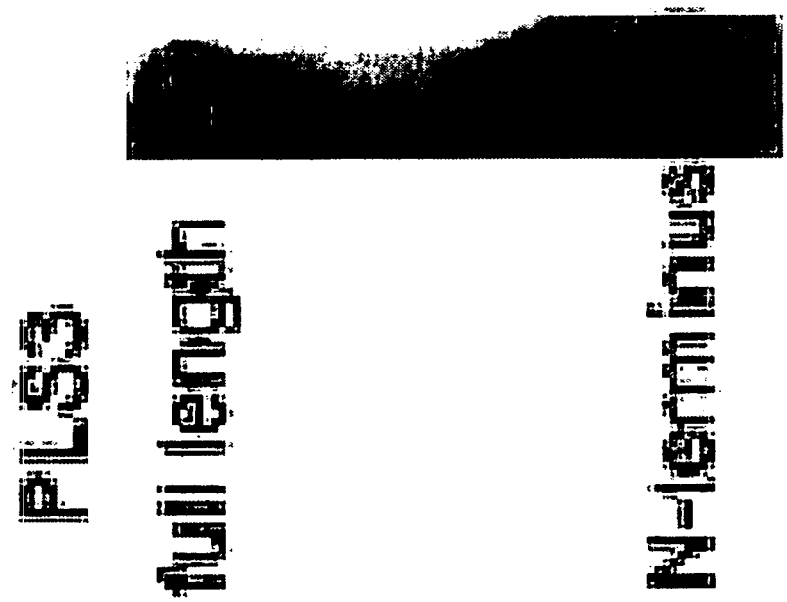
FIG. 9A is a radiograph of the in vitro phosphorylation of PLS3 by PKC-δ. Equal amounts of recombinant PLS3 and a 6 kDa $NH_2$-terminal fragment of PLS3 were mixed together and phosphorylated by purified PKC-δ in the presence of [$\gamma$-$^{32}$P]ATP. The phosphorylated sample was analyzed with a SDS gel and the gel was exposed by autoradiography.
Figure 9B:
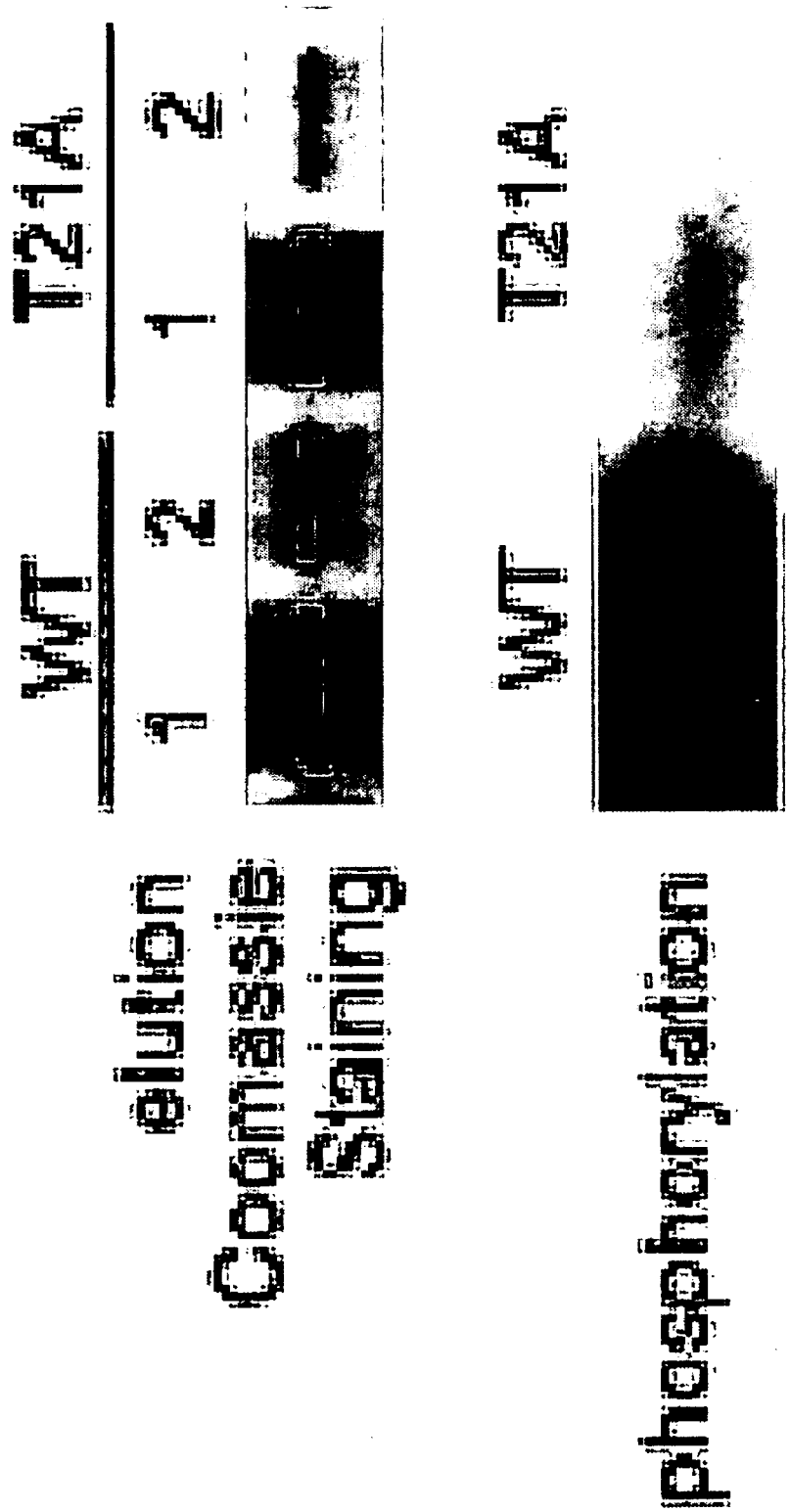
FIG. 9B is a gel showing the affect of a T21A mutation on PLS3 phosphorylation by PKC-δ. Recombinant His-tagged PLS3 (wild-type, WT) and T21A mutant were isolated by Ni beads from two elutions and analyzed with SDS gel. On the top, the yield of each protein in the two-step elution is indicated by Coomassie staining. The bottom indicates in vitro phosphorylation of equal initial amounts of PLS3 proteins by recombinant PKC-δ.

PLS3 is a high affinity substrate of PKC-δ in vitro. See Liu, J., et al., *Cancer Res.*, 63, 1153-1156 (2003). The in vitro phosphorylation of PLS 3 was repeated by mixing equal amounts of recombinant PLS3 and a 50 amino-acid NH$_2$-terminal fragment of PLS3 were mixed together and phosphorylating with purified PKC-δ in the presence of [γ-$^{32}$P] ATP. Phosphorylation was seen in both full-length PLS3 and in the amino-terminal fragment. See FIG. 9A. Point mutation was used to map the phosphorylation sites. Examination of the first 50 amino acids of PLS3 revealed only a single threonine, Thr21. Thr21 was mutated to an alanine using site-directed mutagenesis. As shown in FIG. 9B, mutation at Thr21 almost eliminates phosphorylation of PLS3 by PKC-6, suggesting that the Thr21 is the site of phosphorylation in PLS3 by PKC-δ in vitro.

Figure 9C:
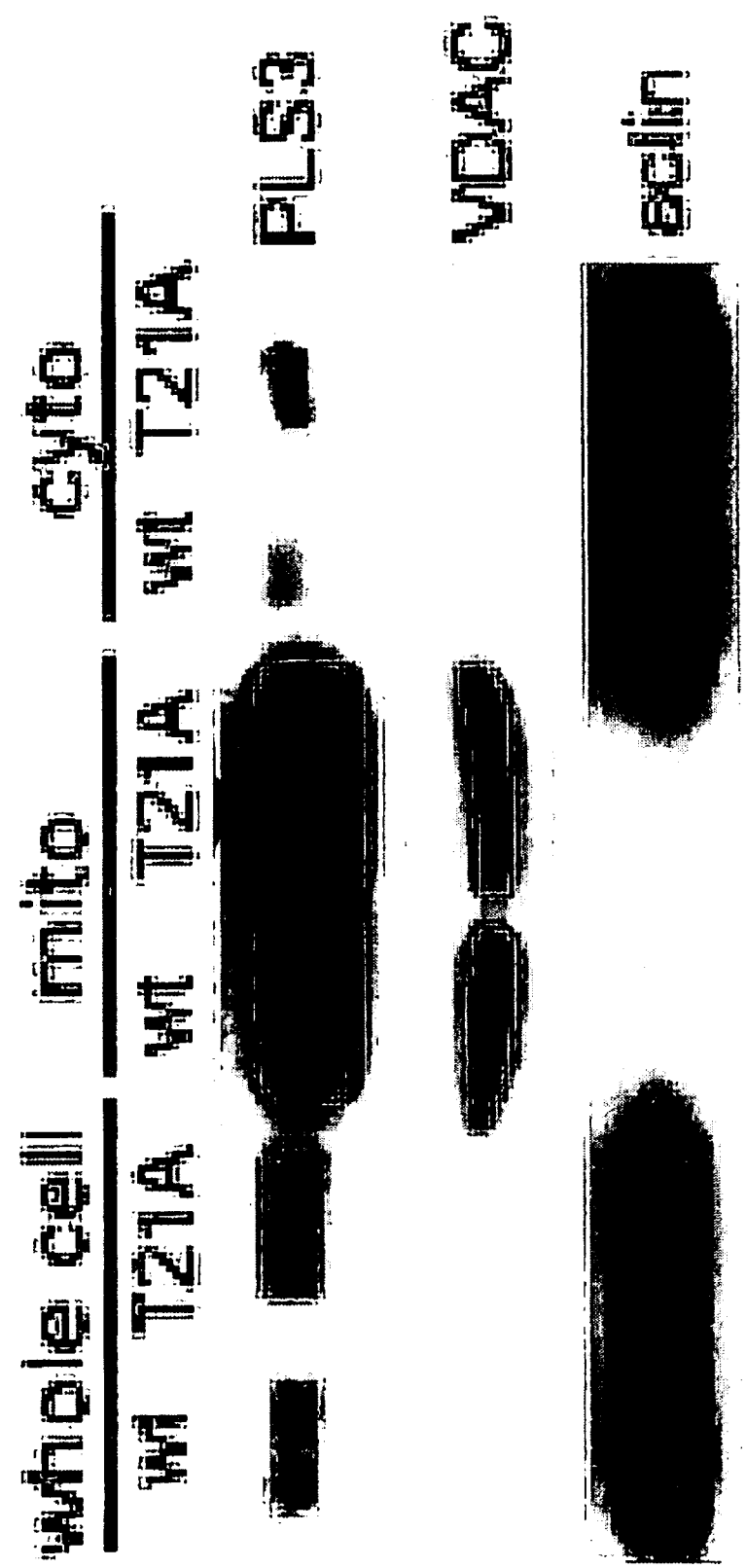
FIG. 9C is an immunoblot showing the subcellular fraction of cells transfected with the PLS3 (WT) or PLS3(T21A) expression vectors.

The mammalian expression vector pCMV-6His-PLS3 (T21A) was transfected into HeLa cells to investigate the effect of T21A mutation in vivo. Using Ni-beads to pull down His-tagged PLS3(T21A) from cell lysates, it was found that the PLS3(T21A) mutant could not be recognized by the PT antibody either before or after cells were treated with AD 198. See FIG. 9C. In contrast, wild-type PLS3 was recognized by the PT antibody, and the signal increased after AD 198 treatment, indicating that Thr21 is also the site of PLS3 phosphorylation by PKC-δ in vivo.

Figure 9D:
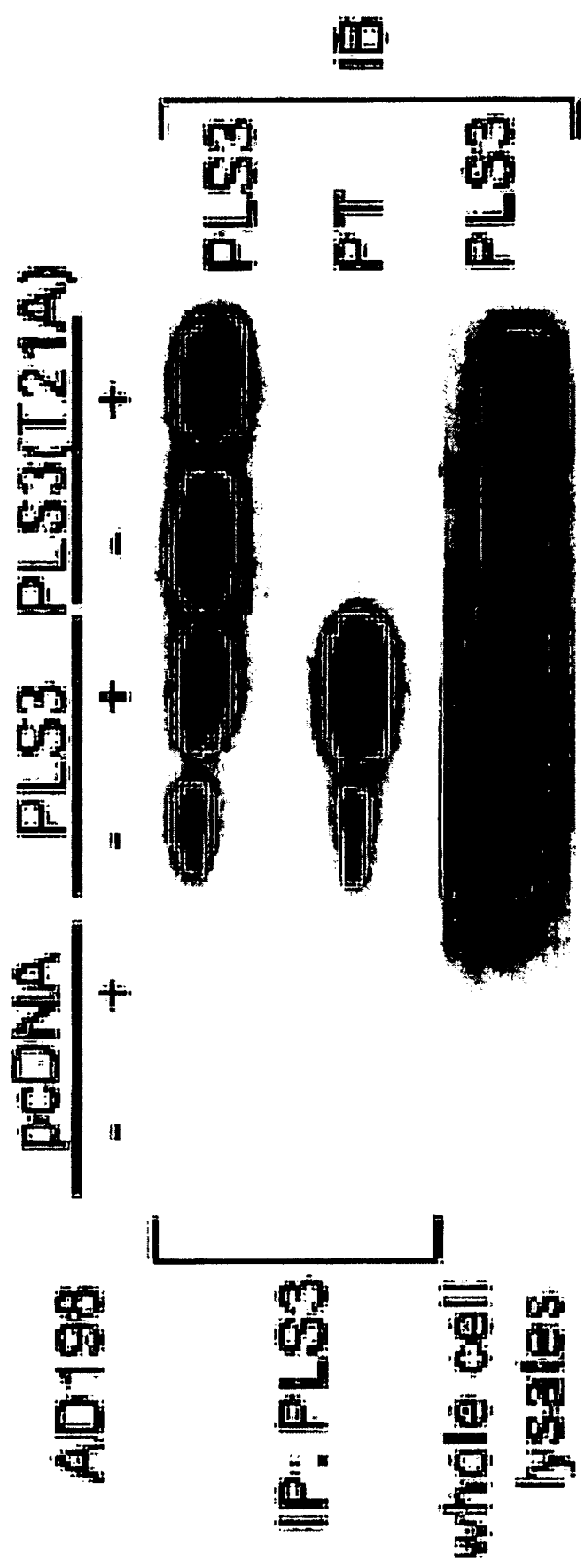
FIG. 9D is an immunoblot showing how the T21A mutation abolishes in vivo PLS3 phosphorylation after AD 198 treatment. HeLa cells were transfected with the control vector or vectors expressing His-tagged PLS3 or PLS3(T21A). His-tagged PLS3 protein was pulled down with Ni beads from cells treated with (+) or without (−) AD 198. Whole cell lysates and pulldown samples were analyzed with Western blotting using antibodies against PLS3 and phosphothreonine.
Figure 9E:
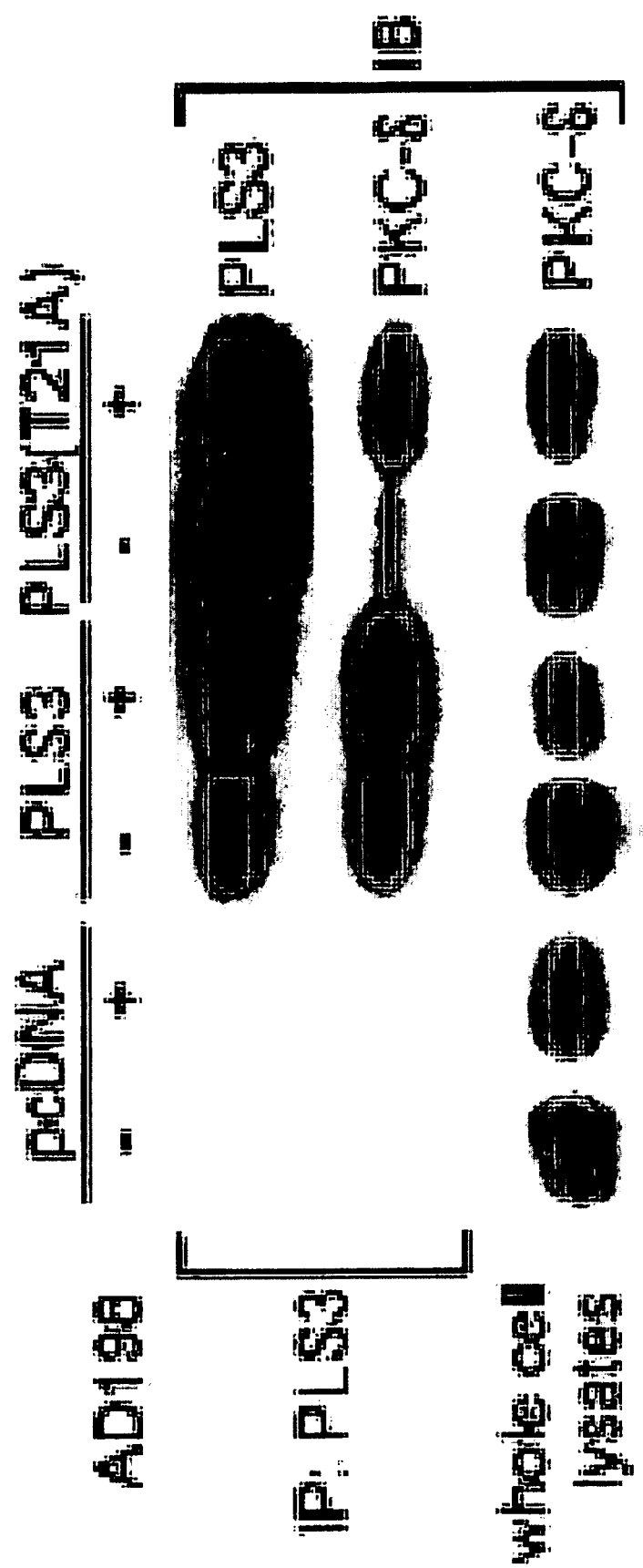
FIG. 9E is an immunoblot showing the interaction of PLS3 (T21A) with PKC-δ. HeLa cells were co-transfected with the PKC-δ vector and pcDNA, PLS3, or PLS3(T21A) vector. Whole cell lysates were incubated with Ni beads to pull down PLS3. The pulldown samples were analyzed by Western blotting using antibodies against PLS3 and PKC-δ.
Figure 9F:
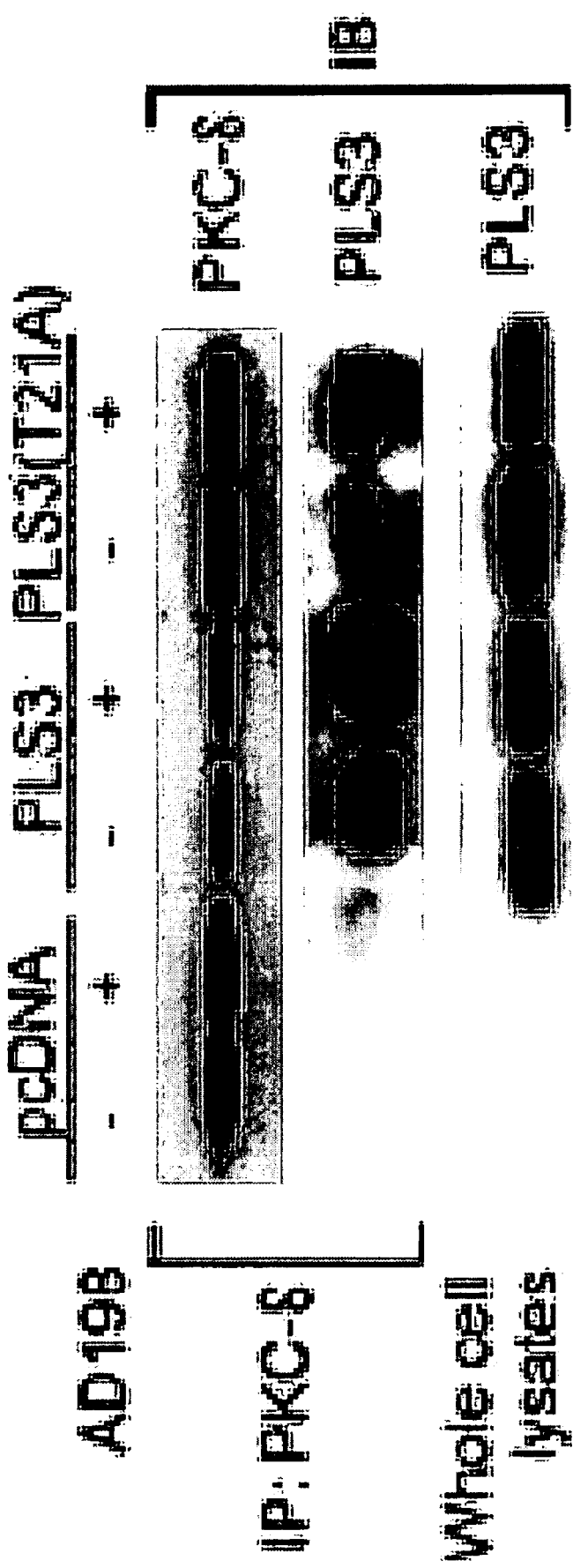
FIG. 9F is an immunoblot further showing the interaction of PLS3(T21A) with PKC-δ. HeLa cells were co-transfected as described for FIG. 9E. Whole cell lysates were immunoprecipitated with PKC-δ antibody. Whole cell lysates and immunoprecipitates were analyzed by Western blotting with the antibody against PLS3.

After pulling down His-tagged PLS3(T21A) by Ni-beads, the PLS3(21A) mutant could not be recognized by PT antibody, even after treatment with AD 198. See FIG. 9D. In contrast, wild type PLC3 was recognized by the same PT antibody and the signal increased with AD 198 treatment. To further study how the T21A mutation affects the interaction of PLS3 and PKC-δ, cells were co-transfected with the PKC-δ. The His-tagged PLS3 pulled down by Ni beads contained PKC-δ, but PLS(T21A) was less effective in binding PKC-δ compared to wild-type PLS3 before AD 198 treatment, athough the amount of PLS3(T21A) was higher by blotting the same blot with PLS2 antibody. See FIG. 9E. Upon incubation with AD 198, there was increased association of PLS3 and PKC-δ for wild-type PLS3 versus mutant PLS3(T21A). The reciprocal immunoprecipitation with the PKD-δ antibody showed similar results. Cells treated with AD 198 had more PLS3 present in the PKC-δ immunoprecipitate. The PLS3(T21A) mutant had a weaker interaction with PKC-δ. See FIG. 9F. These results indicate that the interaction between PLS3 and PKC-δ was compromised in PLS3 (T21A), and therefore, AD 198-induced association between PLS3 and PKC-δ requires phosphorylation residue Thr21 in PLS3.

Figure 10A:
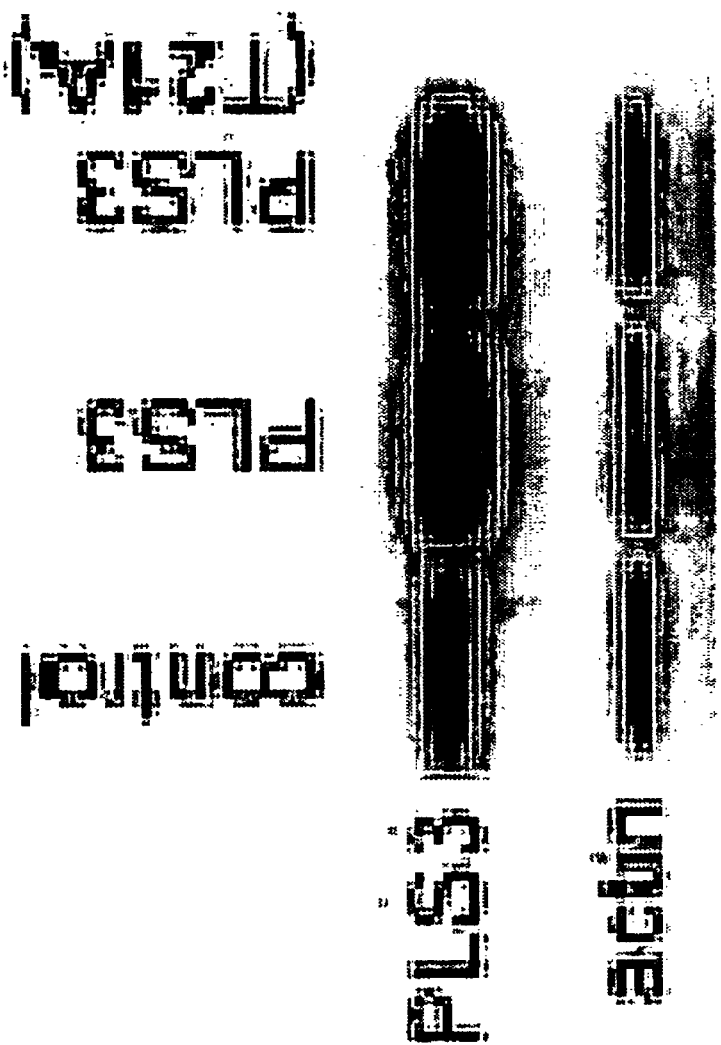
FIG. 10A is an immunoblot showing protein expression in HeLa cells transfected with the empty vector (control) or vectors expressing PLS3 or PLS3(T21A). Cells were harvested for Western blotting with antibodies against PLS3 and actin.
Figure 10B:
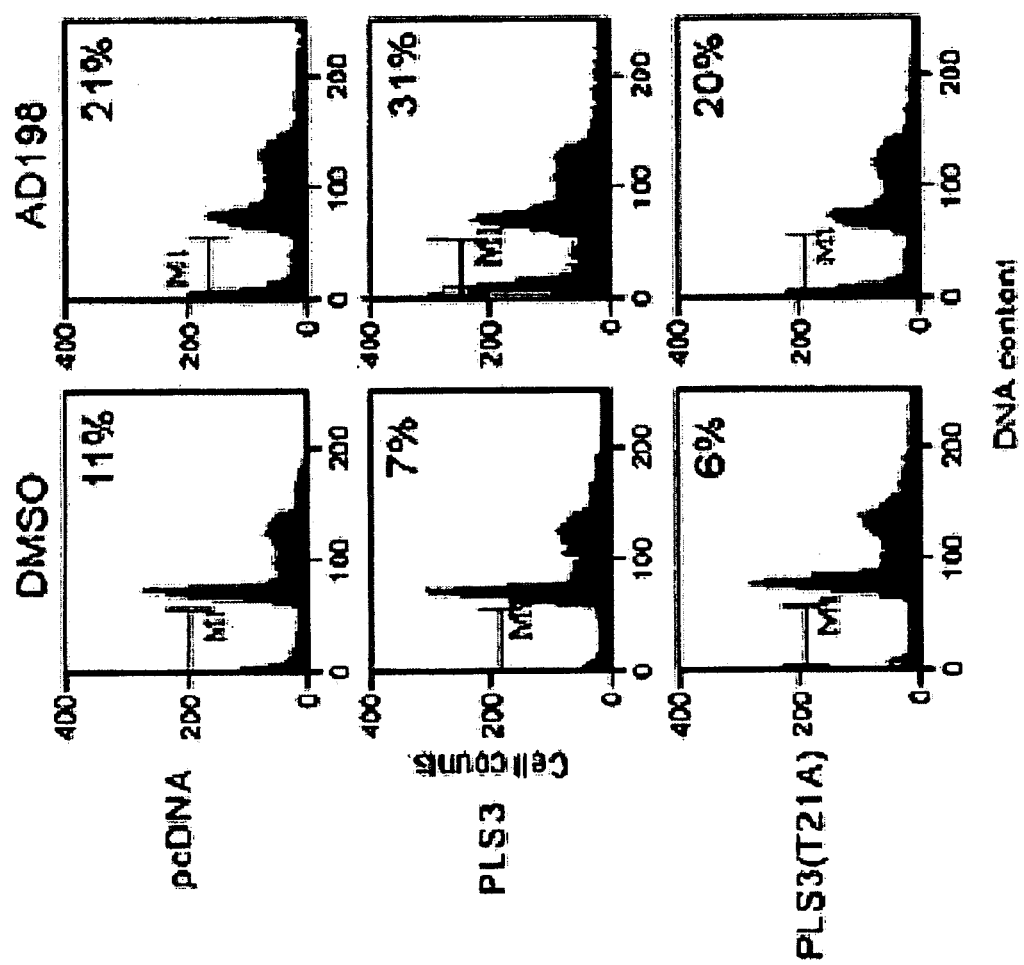
FIG. 10B shows fluorescence emission graphs of AD 198-induced apoptosis in cells transfected as described for FIG. 10A. The transfected cells were treated with DMSO or 5 µM AD 198 for 16 hr followed by flow cytometry analysis with propidium iodide staining. The sub-$G_0$ apoptotic population was determined and indicated in each panel.
Figure 10C:
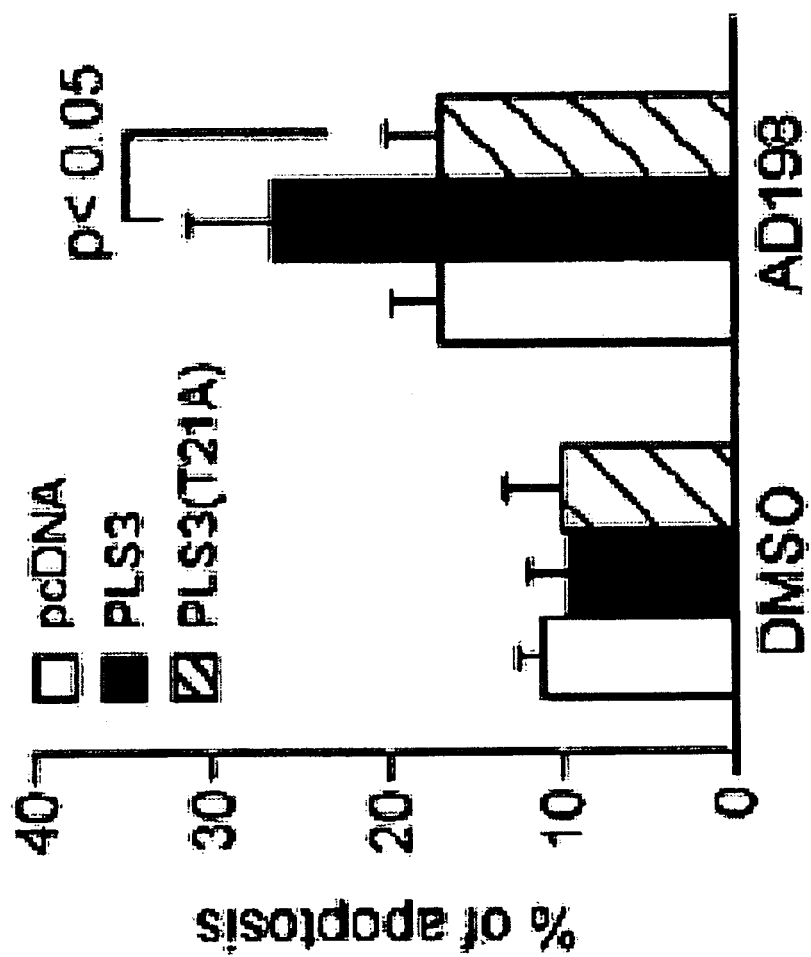
FIG. 10C is a bar graph showing the average apoptotic population in control cells (open bars) and in cells transfected with PLS3 (solid bars) or PLS3(T21A) (striped bars). The transfected cells were treated with DMSO or AD 198 as described for FIG. 10B. Results are the averages of three independent experiments. Statistical significance (P>0.05) was achieved by the paired t test between wild type PLS3 versus control or PLS3(T21A).

If PLS3 phosphorylation at Thr21 is critical for the apoptotic effect of AD 198-activated PKC-δ, the overexpression of PLS3(T21A) should not be able to enhance AD 198-induced apoptosis as did the wild-type PLS3 (FIG. 6A). Therefore, HeLa cells were transfected with wild-type PLS3- or PLS3 (T21A)-expressing vector with AD 198, and apoptosis was analyzed using PI staining and flow cytometry. As shown in FIGS. 10B and 10C, wild-type PLS3 enhanced AD 198-induced apoptosis from 7% to 31%. Cells that expressed PLS3(T21A) had the same degree of apoptosis as the control cells after AD 198 treatment. Thus, it appears that AD 198-induced PKC-δ activation to phosphorylate PLS3 at Thr21 is critical to AD 198-induced apoptosis.

Figure 11A:
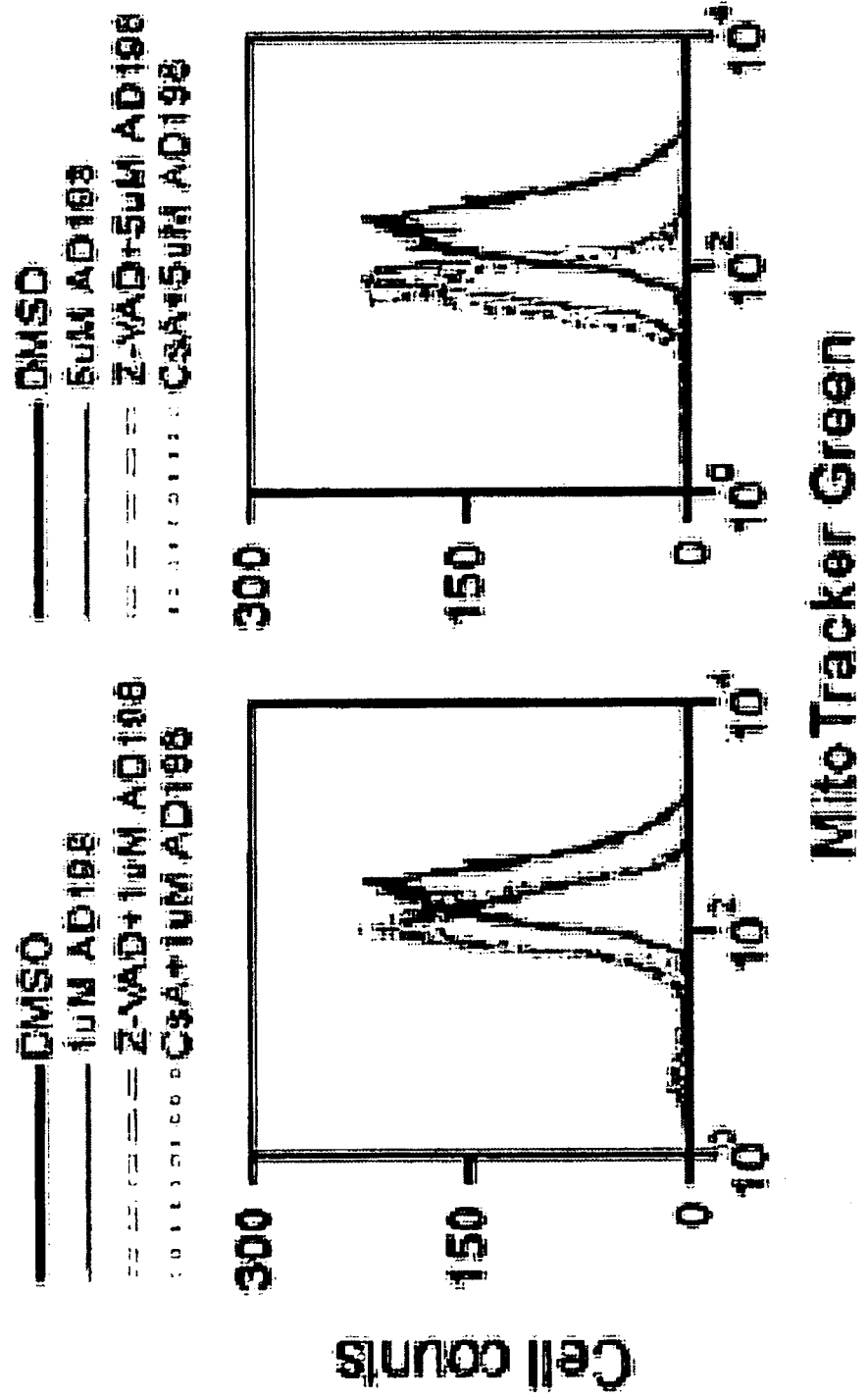
FIG. 11A is a flow cytometry analysis of the effects of Z-VAD-FMK and CsA on AD 198-induced loss of mitochondrial membrane potential. HeLa cells were treated with 50 µM Z-VAD-FMK or 5 µM CsA for 30 min, and then AD 198 was added at 0, 1, or 5 µM for 16 hr. Cells were incubated with MITOTRACKER® Green (Molecular Probes, Inc., Eugene, Oreg., United States of America) at 37° C. for 20 min followed by flow cytometry analysis. Cells treated with DMSO are shown by the heavy solid lines. Cells treated with AD 198 only are shown by the light solid lines. Cells treated with Z-VAD-FMK and AD 198 are shown by the dashed lines. Cells treated with CsA and AD 198 are shown by the dotted lines.
Figure 11B:
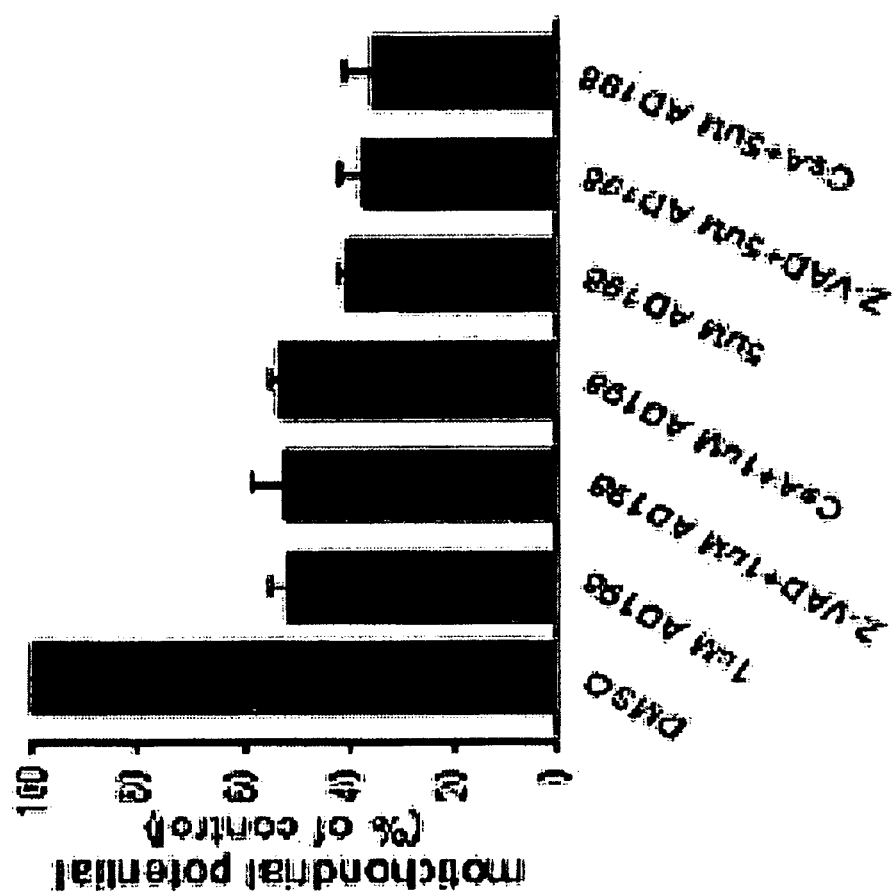
FIG. 11B is a bar graph representing the results of the flow cytometry data shown in FIG. 11A. The bars represent the mean mitochondrial potential (as a percentage of the mitochondrial potential of control cells) from three independent determinations.
Figure 11C:
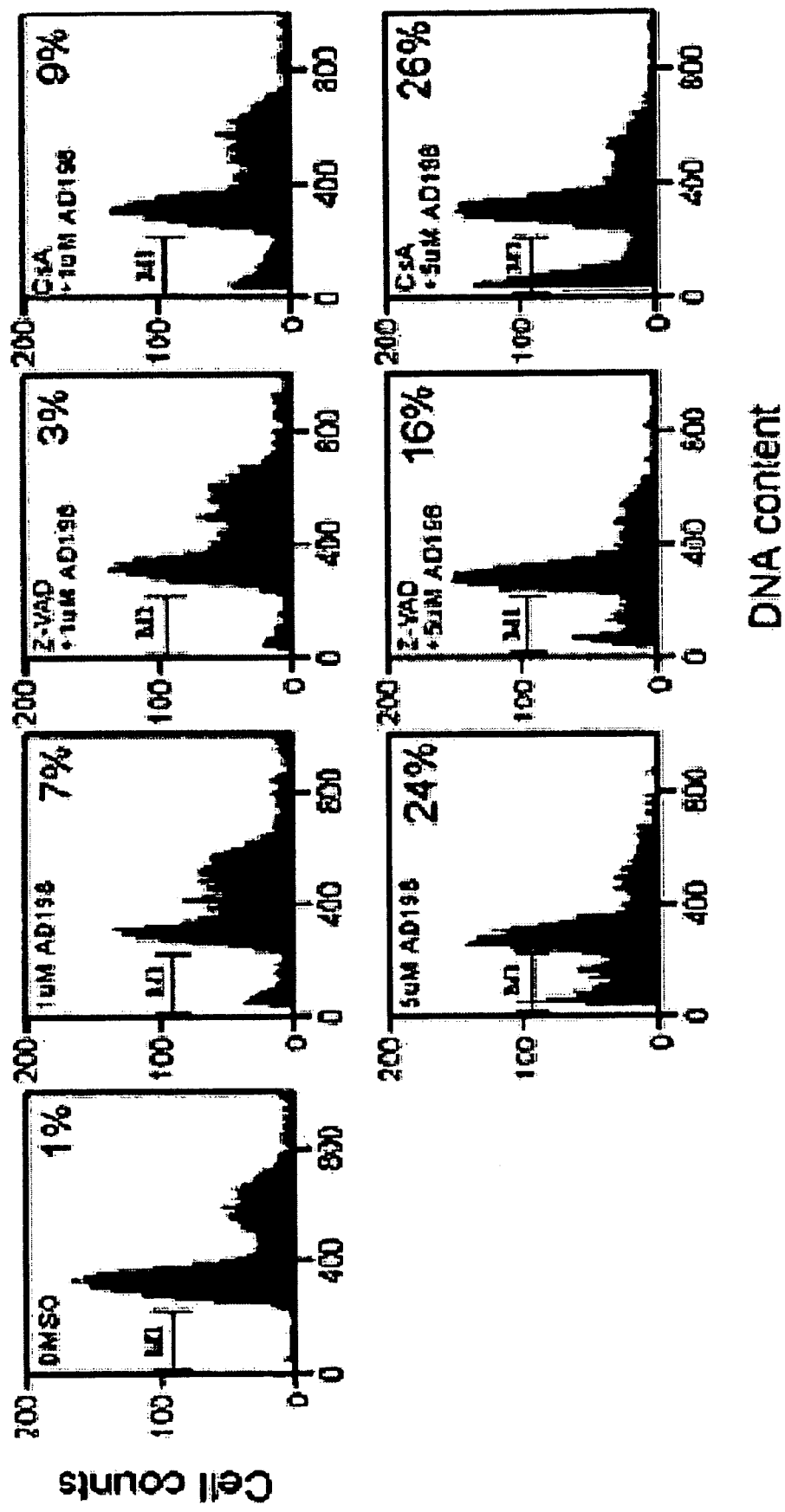
FIG. 11C is the fluorescence emission data showing that Z-VAD-FMK, but not CsA, inhibits AD 198-induced apoptosis. HeLa cells were treated as described for FIG. 11A and collected for staining with propidium iodide.
Figure 11D:
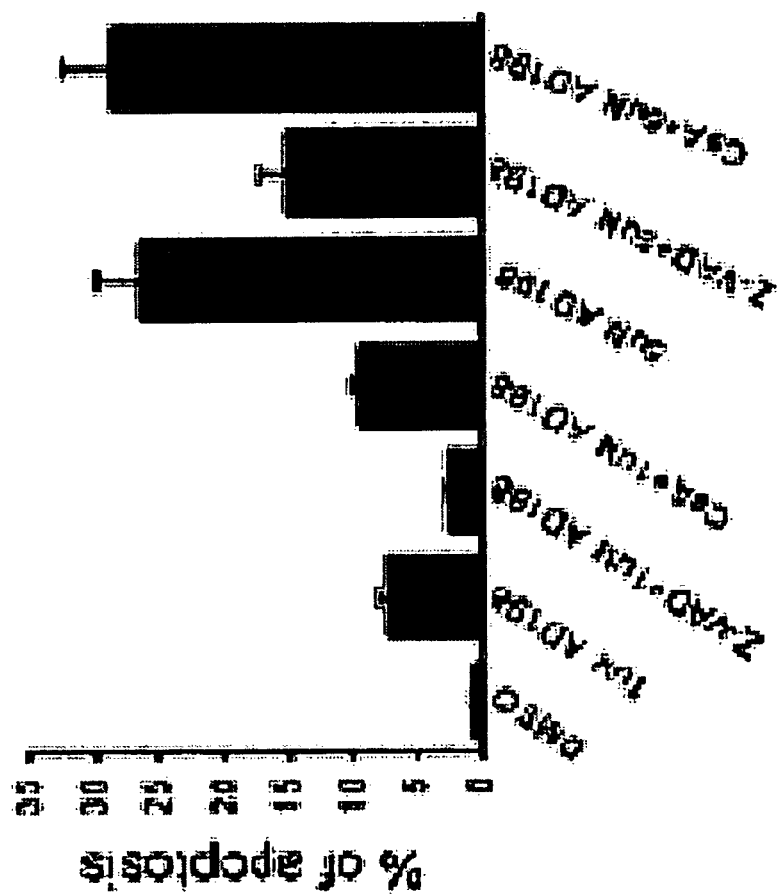
FIG. 11D is a bar graph of the apoptosis data shown in FIG. 11C. Columns represent the mean of independent determinations.
Figure 11E:
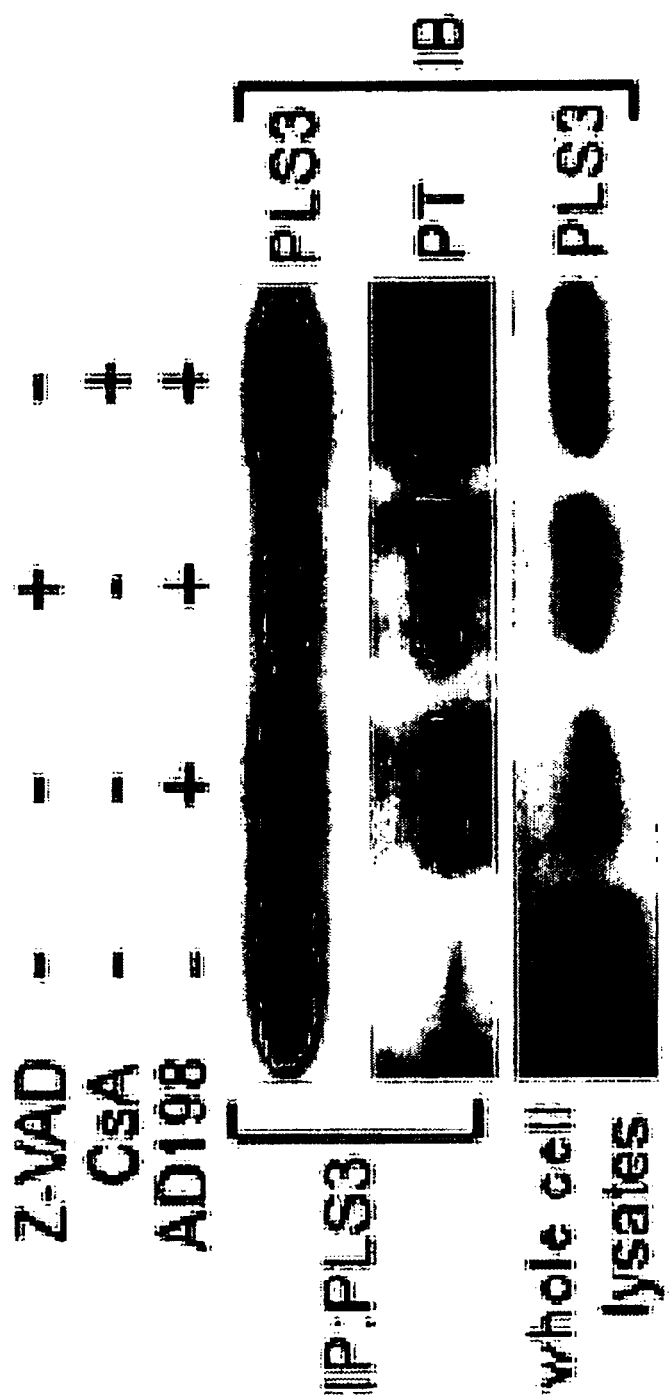
FIG. 11E is an immunoblot showing the effects of Z-VAD-FMK and CsA on AD 198-induced PLS3 phosphorylation. HeLa cells were transfected with the vector expressing His-tagged PLS3. Cells were treated with (+) or without (−) AD 198 (5 µM) along with Z-VAD-FMK or CsA for 2 hr as indicated by the (+) and (−) symbols, and harvested for Ni bead pulldown. Whole cell lysates and pulldown samples were probed with antibodies against phosphothreonine and PLS3.

Finally, to determine how PLS3 phosphorylation is positioned in the apoptosis pathway, HeLa cells were treated with pancaspase inhibitor Z-VAD-FMK followed by AD 198. Z-VAD-FMK did not block AD 198-induced mitochondrial permeability but did suppress AD 198-induced apoptosis. See FIGS. 11A-11D. Further, PLS3 phosphorylation in the presence of Z-VAD-FMK was tested by pulling down the His-tagged PLS3 with Ni beads and probing with PT antibody. Threonine phosphorylation of PLS3 after AD 198 treatment was not affected by Z-VAD-FMK. See FIG. 11E. This result suggests that AD 198-induced PLS3 phosphorylation occurs upstream of caspase activation. Similar studies were carried out to examine if AD 198-induced PLS3 phosphorylation is upstream or downstream of mitochondrial membrane transition. When the mitochondrial permeability transition pore complex was blocked by CsA, AD198-induced loss of mitochondrial membrane potential and PLS3 phosphorylation were not affected. See FIGS. 11A, 11B and 11E. Thus, it appears that PLS3 phosphorylation occurs independent of mitochondrial permeability transition.

Example 5

Circumvention of Drug Resistance in Human Leukemia Cells

Currently, the most effective treatment for chronic myelogenous leukemia (CML) involves the administration of imatinib mesylate (GLEEVEC®), which prevents ATP binding to the fusion tyrosine kinase Bcr-Abl, whose expression as a result of the t(9;22)(q34;q11) reciprocal chromosomal translocation produces the CML malignancy. See Salesse. S. et al., *Oncogene*, 21, 8547-8559 (2002). Incomplete cytogenetic remission following imatinib treatment is indicative of cellular resistance to imatinib through either Bcr-Abl-dependent or -independent mechanisms, including kinase mutations of Bcr-Abl that inhibit imatinib binding, Bcr-Abl overproduction, overexpression of the MDR1 (P-glycoprotein) and MRP1 multidrug transporters, and as well as the increased LYN kinase expression leading to elevated levels of the anti-apoptotic Bcl-2 protein. See Shah, N. P., *Hematology (Am Soc Hematol Educ Program)*, 183-187 (2005); Gorre, M. E. et al., *Science*, 293, 876-80 (2001); Dai, Y., et al., *J Biol. Chem.*, 279, 34227-39 (2004).

Figure 12:
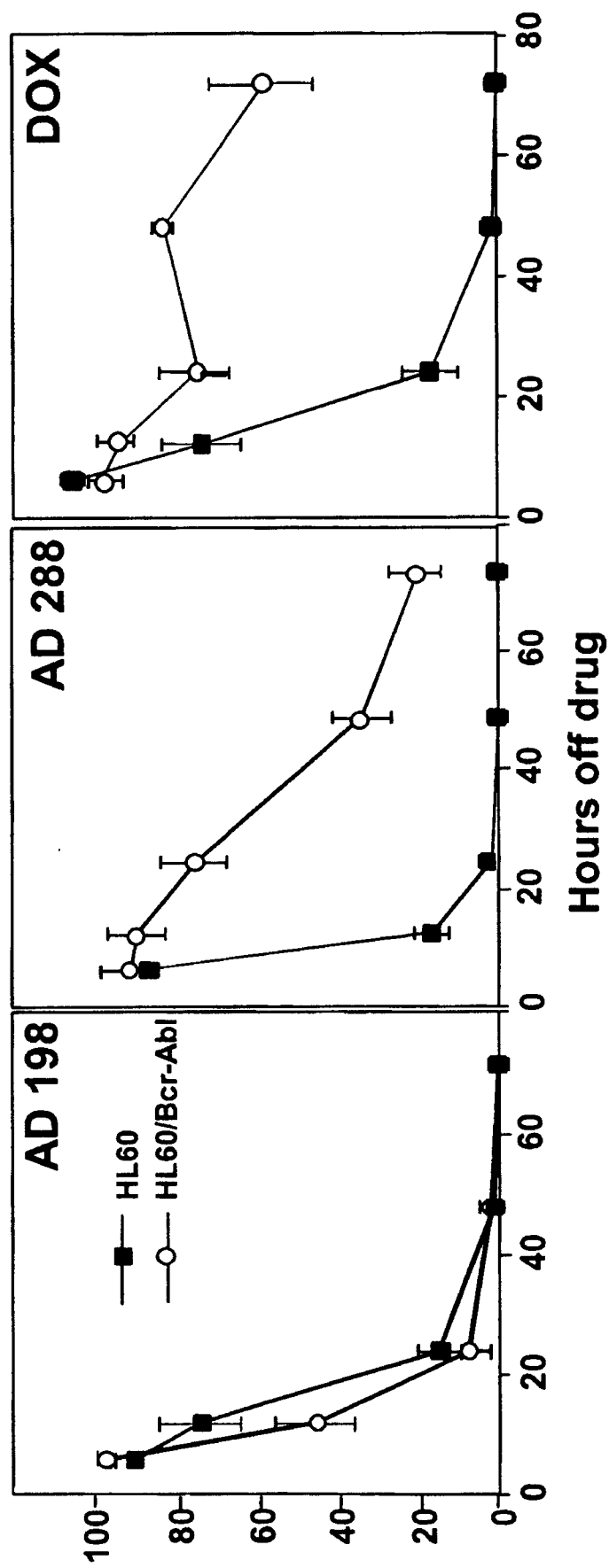
FIG. 12 is a set of graphs presenting a cytotoxicity analysis of 3 µM of AD 198 in HL-60 human promyelocytic leukemia cells with or without the expression of the fusion tyrosine kinase Bcr-Abl from a transfected expression vector, as described in Perkins, C., et al., Blood, 95:1014-22 (2000). Data represent the mean and SE of three independent determinations. ■ HL60; ○ HL60/Bcr-Abl.

The following experiments were designed to determine whether AD 198 possesses the ability to circumvent these multiple mechanisms of resistance in human myelogenous leukemia cells. In FIG. 12, HL-60 cells transfected with a Bcr-Abl expression vector, as described by Perkins, C. et al., *Blood*, 95, 1014-22 (2000), were assessed for sensitivity against the $IC_{90}$ concentrations of AD 198, AD 288, and DOX, as determined for wild-type HL-60 cells. Expression of Bcr-Abl has no effect on the cytotoxicity of AD 198, while HL-60/Bcr-Abl cells demonstrate significant resistance against both DOX and AD 288. These results demonstrate that the proliferative signaling by Bcr-Abl cannot block the cytotoxic effects of AD 198.

Figure 13:
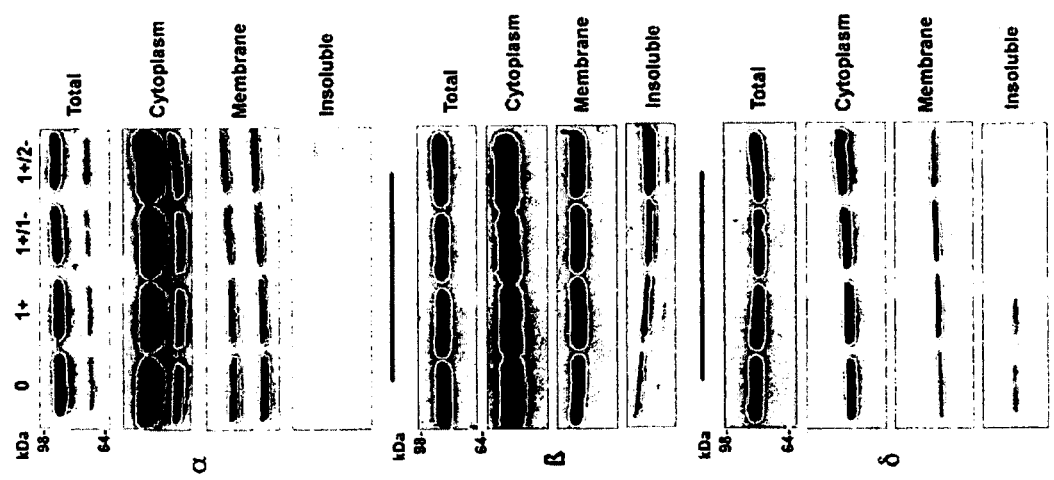
FIG. 13 is an immunoblot showing the translocation of the alpha (α), beta (β), and delta (δ) isoforms of protein kinase C between cytoplasmic, membrane, and detergent-insoluble fractions of K562 cells following treatment with 3 µM AD 198 using protocols as described in Barrett, C. M., et al., Molec. Cancer Ther. 1:469-481 (2002).
Figure 14:
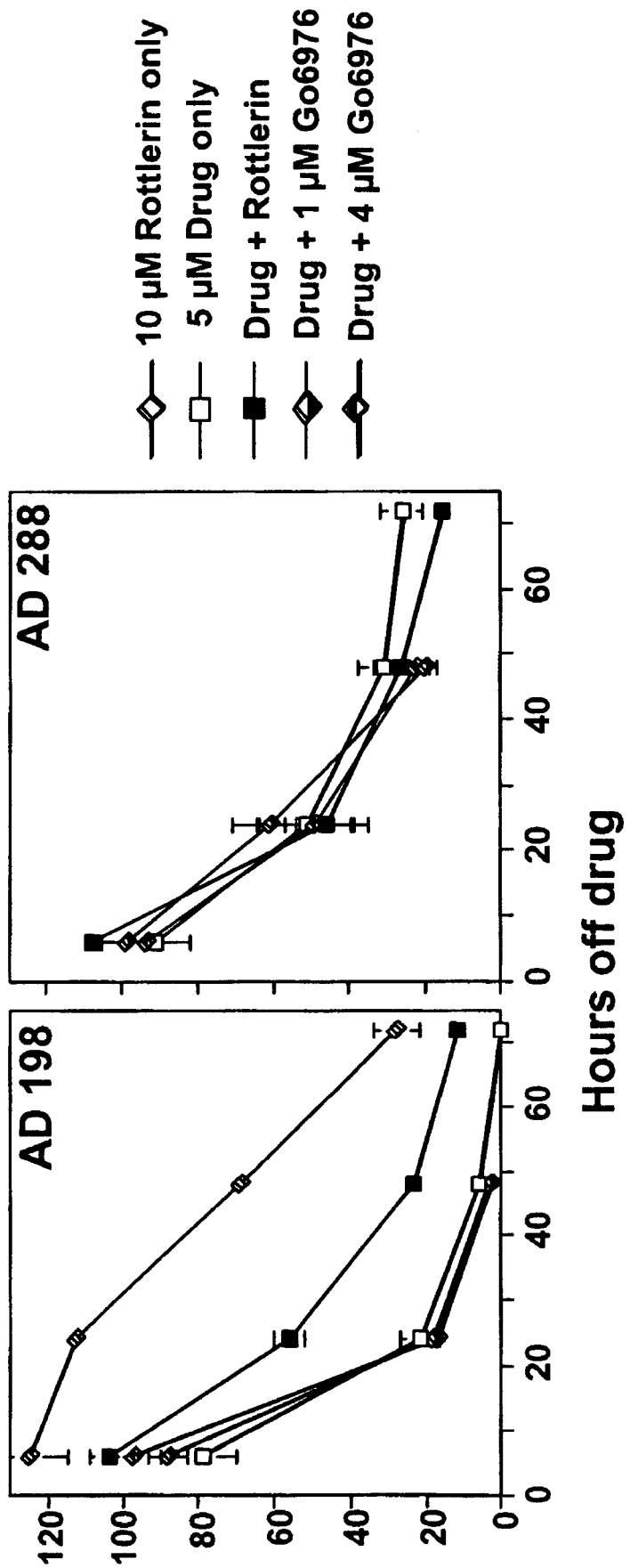
FIG. 14 is a set of graphs presenting a cytotoxicity analysis of 3 µM AD 198 or AD 288 in K562 cells co-treated with either the PKC-δ-specific inhibitor, rottlerin, or the PKC-α, β, and γ-selective inhibitor, Go6976 using protocols described in Barrett, C. M., et al., Molec. Cancer Ther. 1:469-481 (2002). Data represent the mean and SE of three independent determinations.

In K562 CML cells expressing endogenous Bcr-Abl, AD 198 induces rapid apoptosis that is associated with the translocation of PKC-δ from the cytosol to cell membranes, an indicator of PKC activation (FIGS. 13 and 14). Within 1 hour of treatment with 3 μM AD 198, PKC-δ translocation to membrane is detected by immunoblot analysis, while PKCs-α and -β are not translocated to membrane fractions. The significance of PKC-δ translocation/activation is demonstrated by the ability of the PKC-δ-selective inhibitor rottlerin (10 μM) to inhibit AD 198 cytotoxicity. The PKC-α and -β-selective inhibitor Go6976 has no effect on AD 198 cytotoxicity. In contrast, the cytotoxicity of the non-PKC interacting metabolite of AD 198 (AD 288) was not affected by either PKC inhibitor. These results indicate that AD 198 activates PKC-δ to induce cell kill.

Figure 15A:
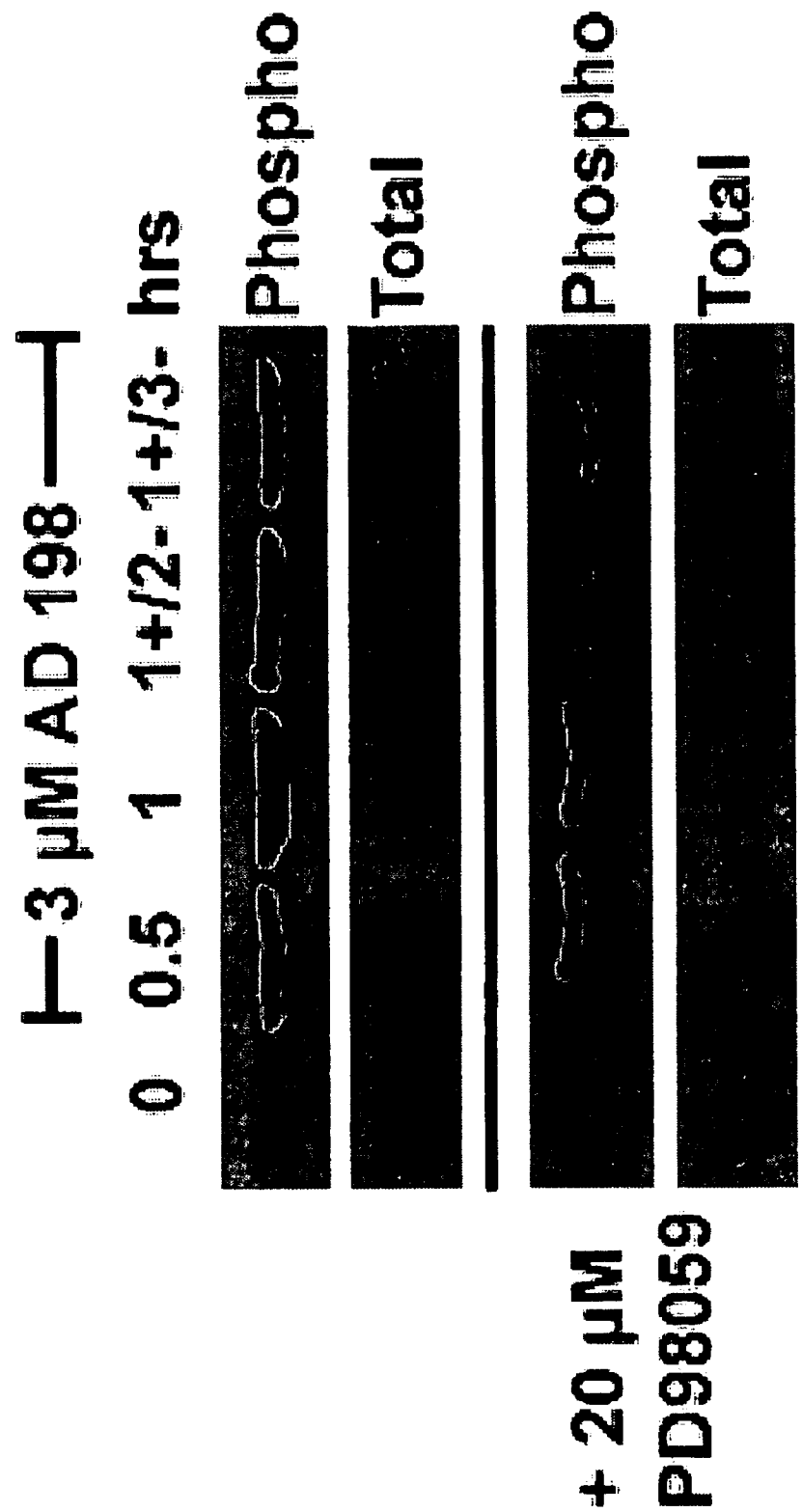
FIG. 15A is an immunoblot showing the phosphorylation of MAP kinase during treatment of K562 cells with 3 µM AD 198 in the absence or presence of the MAP kinase (MEK) inhibitor PD98059.
Figure 15B:
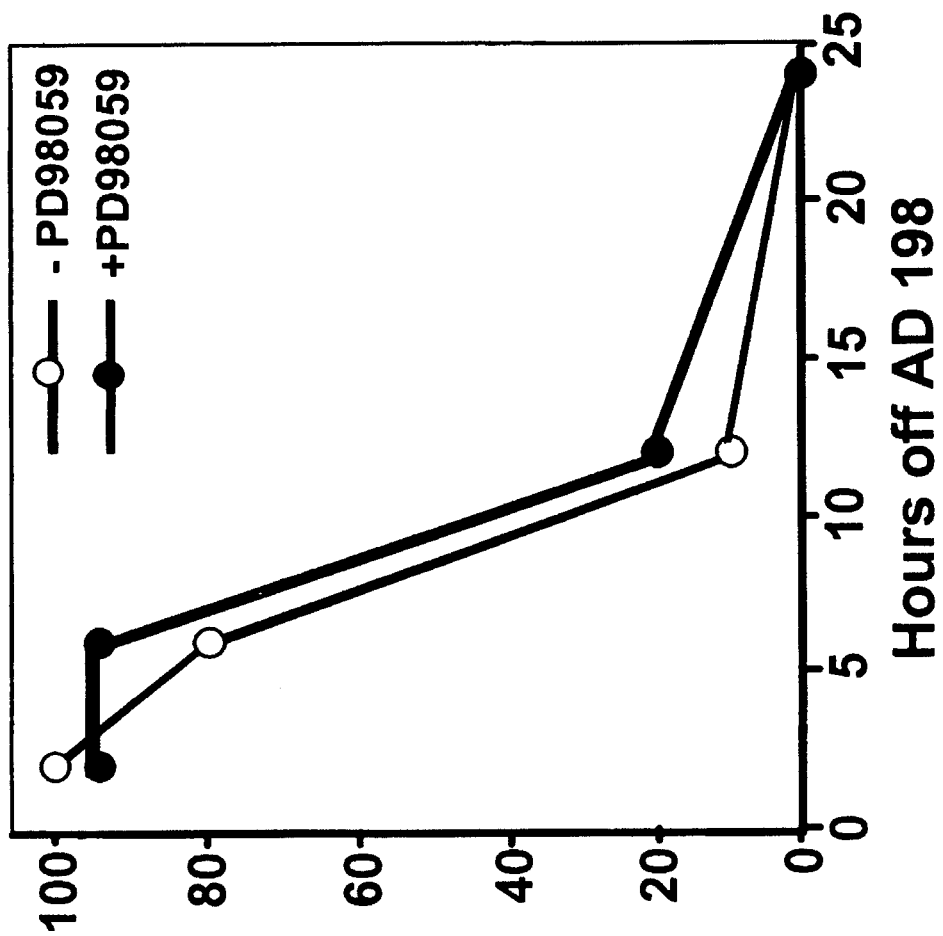
FIG. 15B is a graph presenting a cytotoxicity analysis of K562 cells treated with 3 µM AD 198 in the absence or presence of the MEK inhibitor PD98059 using protocols as described in Barrett. C. M., et al., Molec. Cancer Ther. 1:469-481 (2002). Data represent the mean of two independent determinations.

The next series of experiments were designed to determine whether AD 198 achieves cell kill in Bcr-Abl-expressing K562 cells by either inhibiting proliferative signaling pathways activated by Bcr-Abl or by inducing cell kill despite the proliferative signals produced by Bcr-Abl. Bcr-Abl has been shown to activate the Raf-1/Mek/MAPK(erk1,2) pathway, the PI3/AKT kinase pathway and the JAK/STAT pathway leading to anti-apoptotic Bcl-XL expression and pro-apoptotic Bad phosphorylative inhibition. See Steelman, L. S., et al., *Leukemia*, 18, 189-218 (2004). In FIG. 15A, it is shown that treatment of K562 cells with 3 μM AD 198 induces the phosphorylation and activation of the Raf-1/Mek/MAPK (erk1,2) pathway, as indicated by the increase in phospho-MAPK. In the presence of an inibitor of phosphorylation of the Raf-1/Mek/MAPK(erk1,2) pathway (PD98059; 20 μM), AD 198-induced phosphorylation is inhibited. However, as shown in FIG. 15B, the activation status of the Raf-1/Mek/MAPK (erk1,2) pathway has no effect on the sensitive of K562 cells to AD 198, indicating that AD 198 cytotoxicity does not rely on the inhibition of Bcr-Abl-mediated activation of the Raf-1/Mek/MAPK (erk1,2) pathway.

Figure 16:
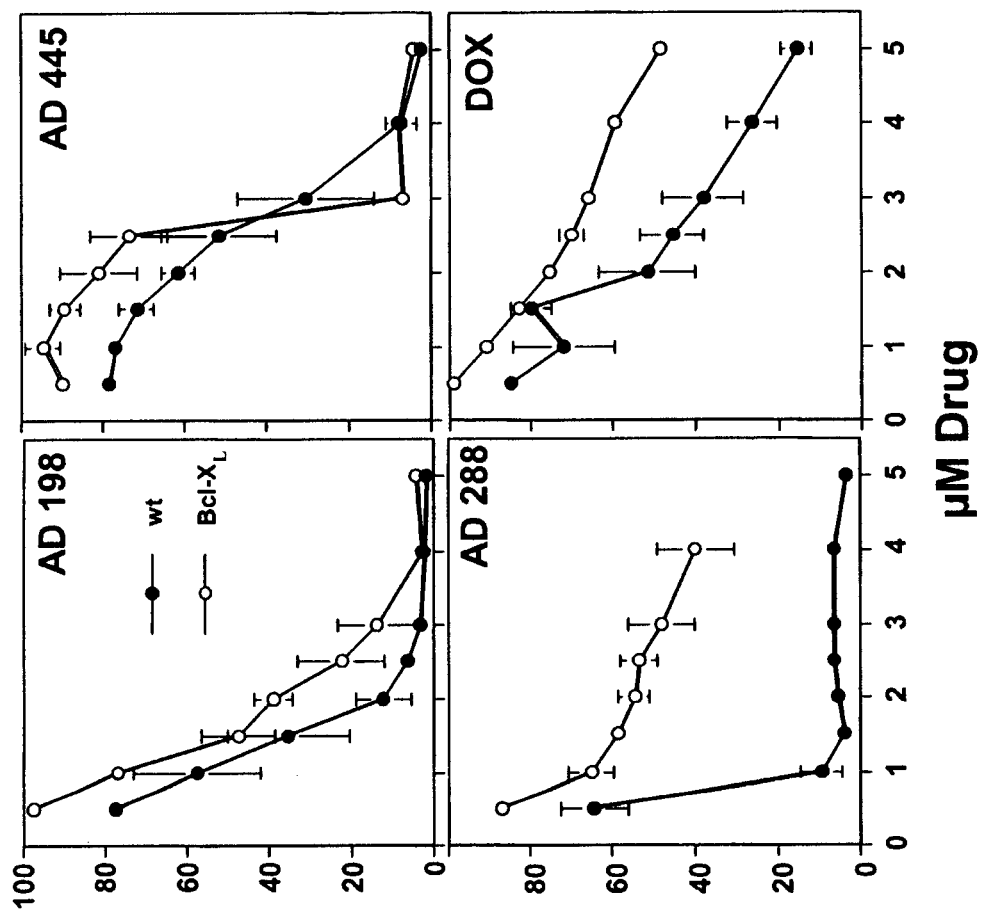
FIG. 16 is a set of graphs presenting a cytotoxicity analysis of 3 µM AD 198 in HL-60 human promyelocytic leukemia cells with or without the expression of the anti-apoptotic protein Bcl-$X_L$ from a transfected expression vector, as described in Perkins, C., et al., Blood, 95:1014-22 (2000). Data represent the mean and SE of three independent determinations.

Previous studies with 32D.3 murine myeloid cells and human MCF-7 breast cancer cells demonstrated that AD 198 and AD 445 cytotoxicity is Bcl-2 and Bcl-$X_L$ overexpression. See Barrett, C. M. et al., *Molec. Cancer Ther.*, 1, 469-481 (2002); and Bilveu, J. D., et al., *Molec. Pharmacol.*, 65, 1038-1047 (2004). FIG. 16 shows the cytotoxicity analysis or AD 198, AD 445, AD 288, and DOX against HL-60 cells with or without a Bcl-$X_L$ expression vector as described in Perkins, C. et al., *Blood*, 95, 1014-22 (2000). AD 198 and AD 445 cytotoxicity in HL-60 cells is unaffected by Bcl-$X_L$ expression, whereas Bcl-$X_L$ expression produces resistance to both DOX and AD 288.

Figure 17:
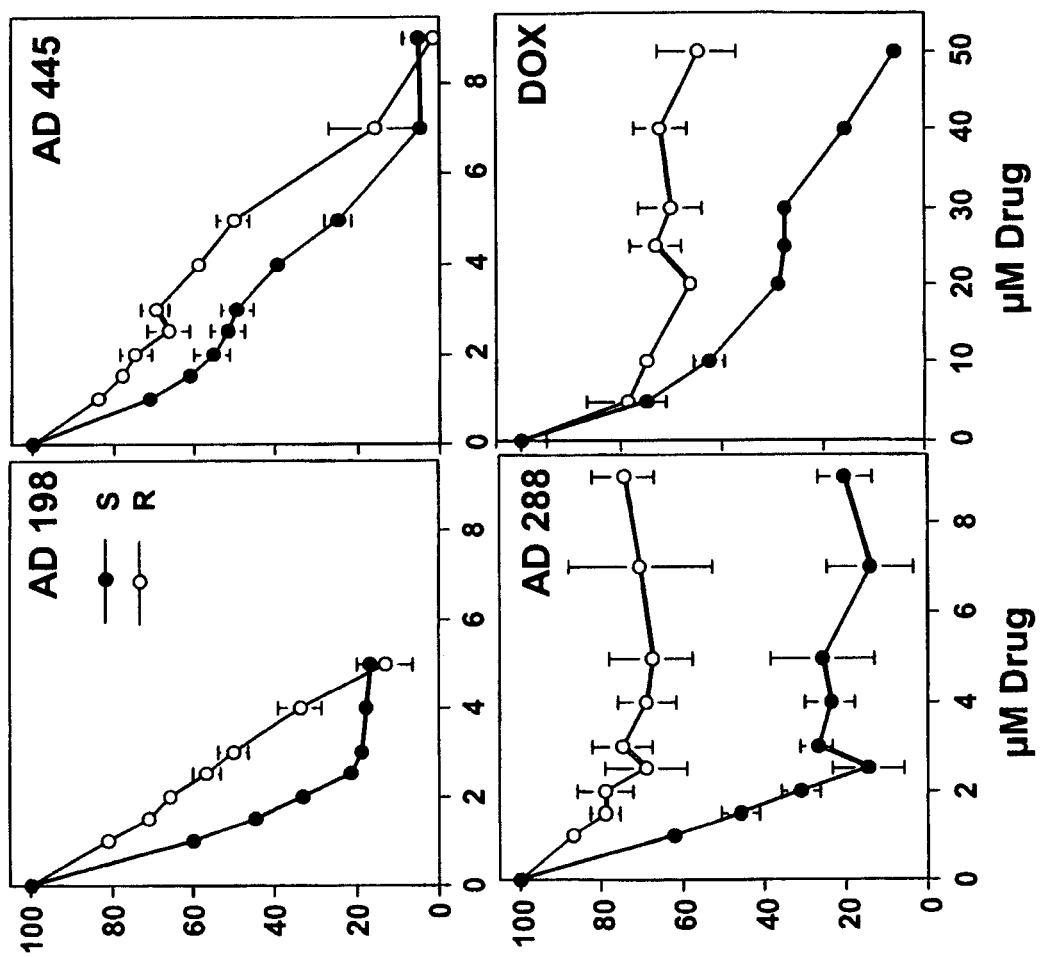
FIG. 17 is a set of graphs presenting a cytotoxicity analysis to determine the $IC_{50}$ and $IC_{90}$ values (drug concentration that inhibits cell growth by 50% and 90%, respectively) of AD 198 48 hours after a 1 hour exposure to the indicated concentrations of drug in drug-sensitive K562 cells (S) or K562 cells overexpression the multidrug transporter, P-glycoprotein (R), as initially derived by Yu, C., et al., Cancer Res., 63:2118-26 (2003). The data represent the mean and SE of three independent determinations.

K562 cells selected for resistance to DOX have been shown to express the multidrug transporter P-glycoprotein. See Grant, S., et al., *Leukemia*, 9, 808-14 (1995). In FIG. 17, these cells demonstrate only marginal resistance to AD 198 and AD 445, when comparing $IC_{50}$ values of resistant versus sensitive lines (1.5-fold) and no significant resistance based on comparisons of the $IC_{90}$ values of AD 198 and AD 445. In contrast, these cells were highly resistant to both DOX and AD 288.

Figure 18A:
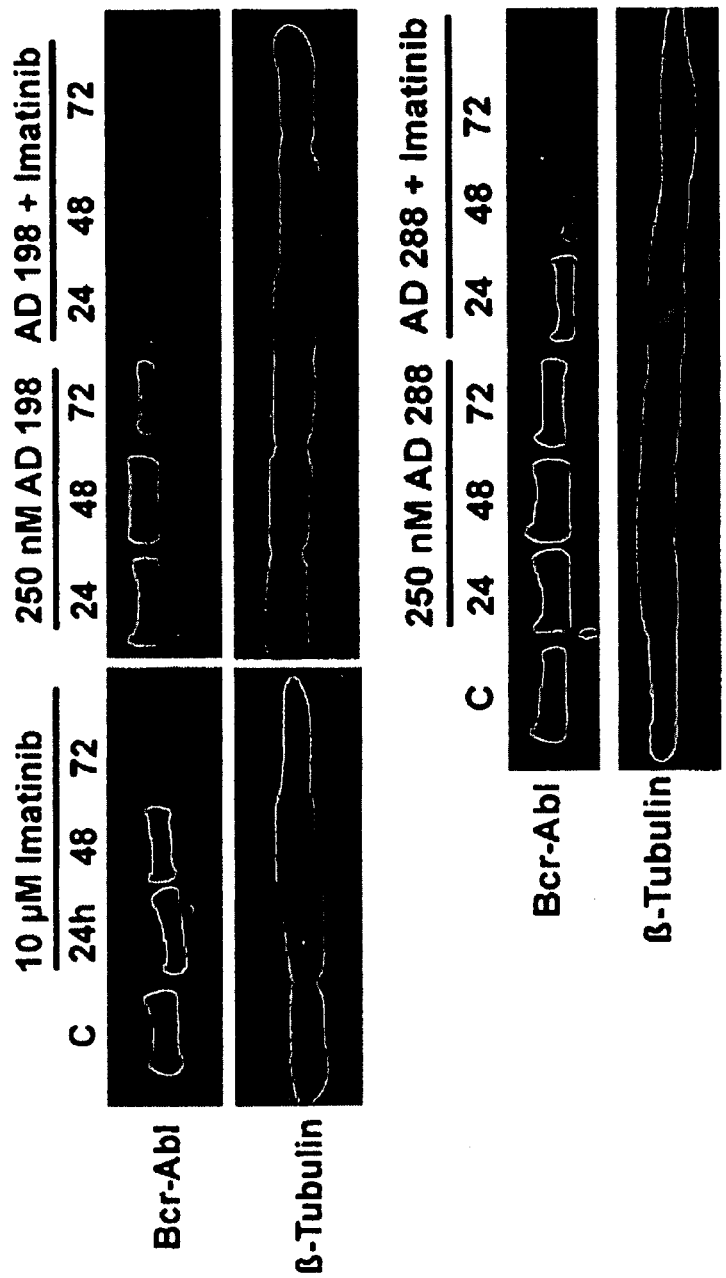
FIG. 18A is an immunoblot showing the changes in expression of Bcr-Abl in K562 cells during treatment with imatinib, AD 198, and AD 288 at the concentrations and combinations described for FIG. 18B.
Figure 18B:
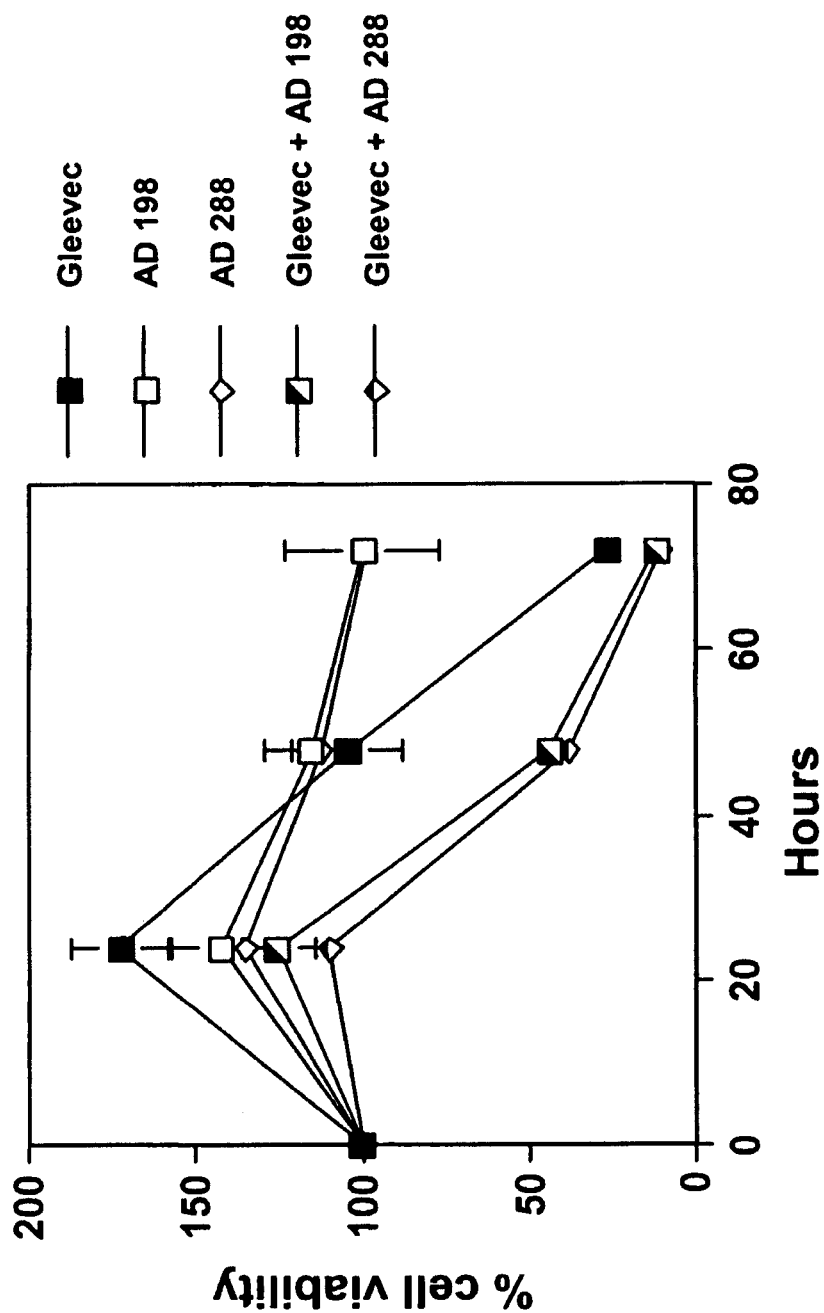
FIG. 18B is a graph presenting a cytotoxicity analysis of K562 cells treated with either 10 µM imatinib (GLEEVEC®), 0.25 µM AD 198, or 0.25 µM N-benzyladriamycin (AD 288), alone, or 10 µM imatinib in combination with either 0.25 µM AD 198, or 0.25 µM AD 288 using protocols as described in Barrett, C. M., et al., Molec. Cancer Ther., 1, 469-481 (2002). The data represent the mean and SE of three independent determinations.

In addition to the ability of AD 198 and AD 445 to circumvent multiple mechanisms of drug resistance in human myeloid leukemia cells, sub-cytotoxic doses of AD 198 and, to a slightly lesser extent, its metabolite, AD 288, demonstrate the ability to synergize with imatinib. Treatment of K562 cells with 10 μM imatinib produces a decrease in expression of Bcr-Abl at 72 hrs of exposure (FIG. 18A) that coincides with approximately 70% cell kill (FIG. 18B). Treatment with 0.25 μM of either AD 198 or AD 288, alone, produces a slight decrease in Bcl-Abl expression 72 hours after drug exposure that accompanies only marginal loss of cells. However, combined treatment of 10 μM imatinib with either 0.25 μM AD 198 or AD 288 produces a 90% loss of Bcr-Abl expression after 24 hours of drug exposure and a concomitant supra-additive increase in K562 cell kill.

Taken together, these results indicated that AD 198 and AD 445 can circumvent multiple mechanisms of cellular drug resistance in human myeloid leukemia cells that blunt the cytotoxic effects of imatinib. Further, AD 198 has the ability to synergize with imatinib through a mechanism that involves inhibition of Bcr-Abl protein expression.

Example 6

Chronic Drug Cardiotoxicity

The murine chronic anthracycline cardiotoxicity model system developed by Bertazzoli et al. was used. See Bertazzoli, C., et al., *Cancer Treat. Rep.*, 63, 1877-1883 (1979). Dose levels of test drugs for chronic administration were based upon the single dose $LD_{50}$ (30 days). Preliminary studies in mice of the same strain and sex as were used for the cardiotoxicity assessment ultimately gave a tightly titrated i.v. single dose $LD_{50}$ (30 days) for DOX of 23 mg/kg and for AD 198 of 46 mg/kg. For chronic administration, high, middle and low dose levels, corresponding to 0.2, 0.1 and 0.05 of the i.v. single dose $LD_{50}$ (30 days) of each drug were used.

Female CD1 mice (PAPIPLUS-virus free; Charles River Laboratories, Wilmington, Mass., United States of America) were divided into dose groups of 10 animals/group. AD 198 or DOX were administered at 0.2, 0.1, and 0.05 of the single dose $LD_{50}$ via the caudal vein. Mice were treated two times per week on weeks 1, 2, 5, 6, and 7; no treatments were administered on weeks 3 and 4 (total 10 injections). Four weeks after last treatments, animals were sacrificed and hearts excised immediately. Intact ventricular myocardia were fixed for a minimum of 24 hours in 10% formalin phosphate buffered to pH 7.0, then carefully sectioned into 2-3 mm thick slices before being dehydrated in graded ethanol and cleared in xylene prior to embedding in paraffin at 58° C. Sections (4 μm thick) were mounted on glass slides, deparaffinized in xylene and stained in the routine fashion with Mayer's hematoxylin and eosin. Slide labels were blinded to the evaluator. Myocardial lesions were evaluated by routine light microscopy and scored with regard to the severity and extent of damage according to the following:

Severity degree (S)
1—sarcoplasmic microvacuolization and/or inclusions, interstitial or cellular edema
2—as in 1, plus sarcoplasmic macrovacuolizations or atrophia, necrosis, fibrosis, endocardial lesions and thrombi Extension degree (E)
0: no lesions
0.5: less than 10 single altered myocytes on the whole heart section
1: scattered single altered myocytes
2: scattered small groups of altered myocytes
3: spread small groups of altered myocytes
4: confluent groups of altered myocytes
5: most of cells damaged Total Cardiotoxicity Score/Animal=$S \times E$ Mean Total Score (MTS) for each treatment group:

$MTS=\Sigma(S \times E)$/no. of animals

Example 7

In Vivo Drug Distribution

Female CD-1 mice were anesthetized momentarily with methoxyflurane and AD 198 (2.5 mg/kg in 20% NCI Diluent 12/80% saline) or DOX was administered as an i.v. bolus via the tail vein. At various times thereafter (5 min, 1 hr, 2 hr, 4 hr, 8 hr, 16 hr, and 24 hr) animals were sacrificed by exsanguinations under anesthesia and hearts were removed and rapidly frozen ($-70°$ C.) for later analysis. Tissue was weighed and homogenized in 3 volumes of Tris buffer (0.05 M, pH 8.5) containing 1.5% sodium lauryl sulfate and extracted 3 times with 9 volumes of ethyl acetate/n-propanol (9:1, by volume). All extracts were evaporated to dryness and reconstituted with methanol containing N-trifluoroacetyladriamycin-14-octanoate as an internal standard. Samples were analyzed by HPLC using both reversed phase separation (C18 NOVA-PAK® 4 µM; 5 mm×10 cm column; Waters Corporation, Milford, Mass., United States of America) and normal phase separation (PARTISIL® PXs 10 PAC column; Whatman Inc., Florham Park, N.J., United States of America). Quantitation was made on the basis of standard curves for AD 198 and AD 288 and recovery of internal standard. Identification was made on the basis of co-elution with laboratory standards in both HPLC separation systems.

Example 8

Monitoring of ROS Generation

Primary murine cardiocyocytes from female C57 mice (Harlan, Indianapolis, Ind., United States of America) isolated as described by Lester, J. W., et al. (Am. J. Physiol. Heart Circ. Physiol., 271, H1778-J1785 (1996)), were preloaded with 5-(and-6)-chloromethyl-2',7'-dichlorodihydrofluorescein diacetate, acetyl ester (CM-$H_2$DCFDA; Molecular Probes, Eugene, Oreg., United States of America) in PBS for 1 hr, followed by removal of PBS and replacement with warm RPMI-1640 medium with 10% FBS. After 15 min. incubation to allow cellular esterases to cleave acetate groups and make the dye sensitive to oxidation, 2.0 µM DOX, 2.0 µM AD 198 or 3.0 µM $H_2O_2$ was added to the cells in suspension for 2 hr, followed by incubation in drug-free medium for 23 hr. Cellular fluorescence was quantified by flow cytometry at an excitation wavelength of 525 nm.

Example 9

Perfused Heart Studies

Perfusion studies were performed as described previously. See Pyle et al., Am. J. Physiol. Heart Circ. Physiol., 279, H1941-1948 (2000). Briefly, hearts were removed from methoxyflurane-anesthetized adult female Wistar rats, female C57 mice or progeny of C57B1/6J×129SvJae F1 heterozygous mice (provided by Dr. Robert O. Messing, University of California, San Francisco, Calif., United States of America; see also Jin, Z. Q. et al., Am. J. Physiol. Heart, Circ. Physiol., 282, H1970-1977 (2002)) bred to produce homozygous PKC-$\epsilon^{-/-}$. Isolated hearts were cannulated in ice-cold modified Krebs-Henseleit buffer (4.7 mM KCl, 118 mM NaCl, 1.2 mM $MgSO_4$, 1.3 mM $CaCl_2$, 25 mM $NaHCO_3$, 11 mM glucose, 1.2 mM $KH_2PO_4$, 0.05 mM EDTA, 2 mM lactic acid, pH 7.4) and then mounted on a Langendorff perfusion apparatus.

While mounted, hearts were placed in a 100 mL bath of oxygenated (95% $O_2$/5% $CO_2$), 37° C. modified Krebs-Henseleit buffer and perfused with the same at a pressure equal to 100 cm $H_2O$. A pressure transducer was inserted through the left atrium into the left ventricle. A cellophane balloon on the end of the pressure transducer was inflated until left ventricular end-diastolic pressure (EDP) was 5 to 15 mm Hg. Pacing at 300 beats per minute was initiated 10-15 minutes after instrumentation. Pacing voltage was set at twice the threshold value. Pre-ischemic LVDP and EDP were averaged from the first 10 min of baseline perfusion. Only hearts with an LVDP between 80-150 mm Hg and an EDP between 5-15 mm Hg were included in the data analysis. Pre-ischemic LVDP was calculated as the pressure difference between peak systolic pressure and EDP.

Figure 20A:
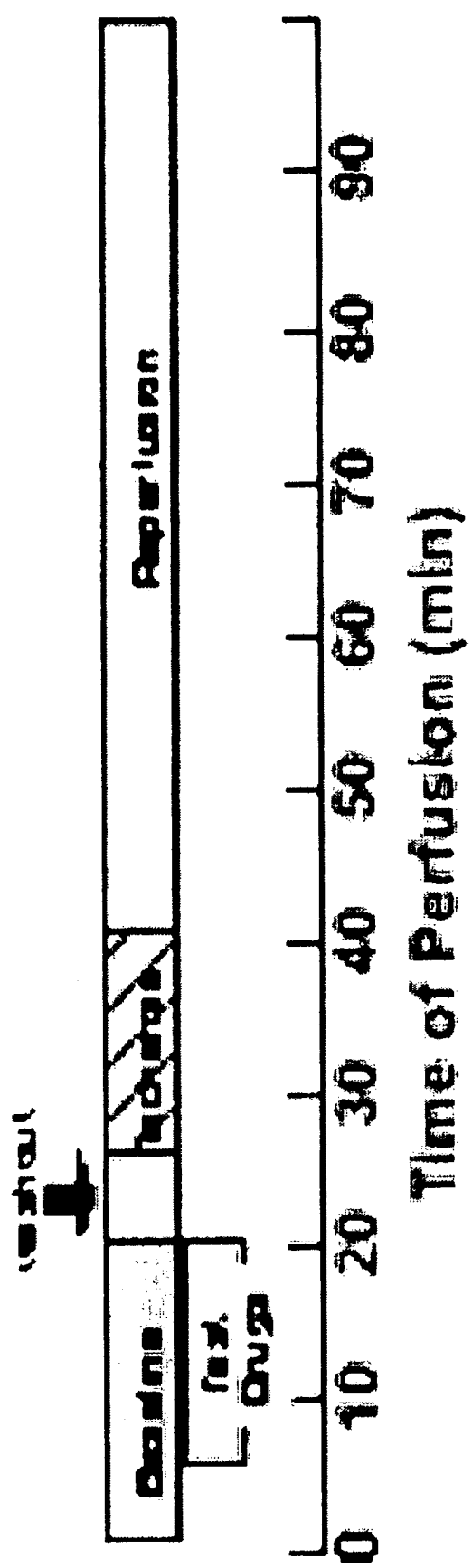
FIG. 20A is a schematic showing the timeline for the Langendorff perfusion protocol, in which excised rat or mouse hearts are perfused with Henseleit buffer for 20 min alone or with either DMSO, DOX, or AD 198 for 15 min. Following a 5 min washout period in Krebs-Heinseleit buffer, the hearts are subjected to global ischemia through vascular occlusion for 15 min. Reperfusion is for 60 min in buffer.

Baseline perfusion or drug perfusion in Modified Krebs-Henseleit buffer was carried out for 20 min followed by a 2-5 min washout of the perfused heart with Modified Krebs-Henseleit buffer plus vehicle. See FIG. 20A. Global ischemia was induced for 15 min, during which time pacing was discontinued. Reperfusion was for 60 min. Post-ischemic LVDP was determined by averaging the last 10 min of post-ischemic reperfusion. Hearts were excluded from data analysis if irreversible post-ischemic dysrhythmias were evident after 20 min of reperfusion. Test drugs were diluted from concentrated stock solutions in DMSO into modified Krebs-Henseleit buffer prior to perfusion.

Example 10

Immunoblot Analysis of Cardiomyocyte Proteins

Rat ventricular myocytes were isolated as previously described. See Liu, Q., and Hofmann, P. A., Am. J. Physiol. Heart Circ. Physiol., 285, H97-H103 (2003). For translocation studies, total membrane fractions were isolated by differential centrifugation in the absence of non-ionic detergent. Identification of PKCs-$\alpha$, -$\delta$, and -$\epsilon$ in cell fractions was performed by SDS-PAGE and immunoblotting as described previously. See Barrett, C. M. et al., Molec. Cancer Therapeutics, 1, 469-481 (2002).

Example 11

Results of Cardiotoxicity Studies

As described above in Example 6, CD1 mice were treated with 0.2, 0.1, and 0.05 times the single $LD_{50}$ dose of DOX over a 10-week period to determine the cardiac effect of chronic dosing with AD 198 and compare that to the effects of chronic dosing with DOX. Four weeks after the final drug dose, excised hearts were assessed for cardiac damage, using as a quantitative measure the severity and extent of myocardial damage to yield mean total score (MTS). As shown in Table 2, at a dose range for DOX of 1.15 to 4.6 mg/kg, MTS increases from 0.7 to 6.14, with overt cardiac damage observed in 90-100% of the animals. In contrast, 0.2, 0.1, and 0.05 of the single dose $LD_{50}$ of AD 198 produced only marginal histological effects with an MTS of 0.1-0.25 that did not appear to be drug concentration-dependent. These results indicate that at chronic dosing levels sufficient to achieve DOX-induced cardiotoxicity, AD 198 is non-cardiotoxic.

TABLE 2

Chronic Cardiotoxicity in DOX and AD 198-trated CD-1 mice.

| Agent | Dose, mg/kg | MTS | Affected Hearts (%) |
|---|---|---|---|
| control |  | 0 | 0 |
| AD 198 | 9.2 | 0.1 | 20 |
| AD 198 | 4.6 | 0.3 | 40 |
| AD 198 | 2.3 | 0.1 | 20 |
| DOX | 4.6 | 6.1 | 100 |
| DOX | 2.3 | 1.9 | 100 |
| DOX | 1.2 | 0.7 | 90 |

Values are the mean of 10 animals per dose group. Calculation of mean total score (MTS) is described in Example 1.

Given the reported significant role of semiquinone-generated ROS in DOX-mediated cardiotoxicity, studies were undertaken to determine whether AD 198 non-cardiotoxicity is attributable to the lack of AD 198-generated ROS in cardiomyocytes, either through reduced uptake of AD 198 into the heart or a reduced ability of the semiquinone ring in AD 198 to generate ROS. Therefore, AD 198 was administered to CD1 mice i.v. through the tail vein as described in Example 7. After various time points, hearts were excised and analyzed for anthracycline content. The results indicated that the non-cardiotoxic characteristic of AD 198 was not due to low drug uptake into the heart.

Figure 19:
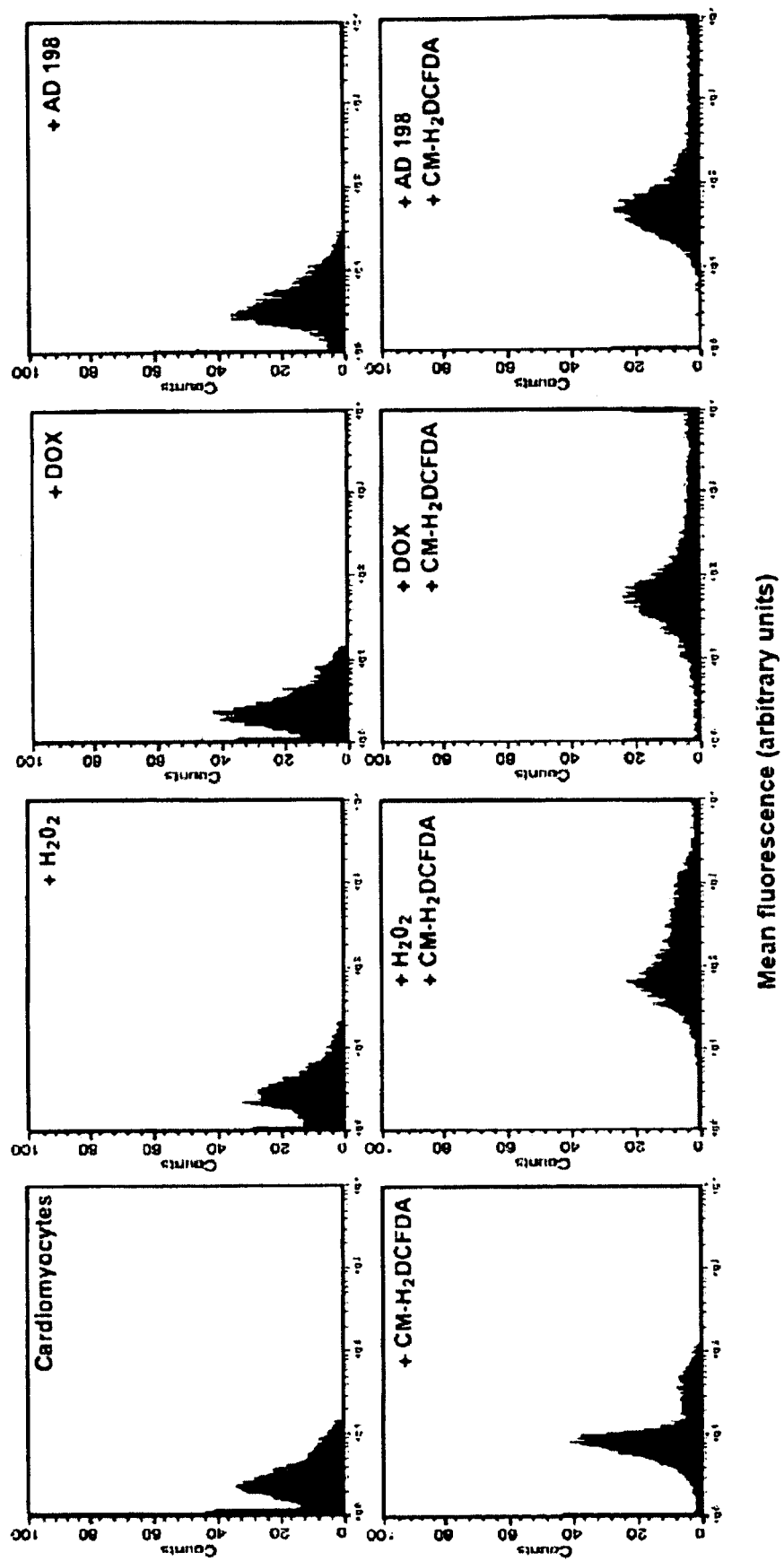
FIG. 19 is fluorescence emission data of freshly isolated rat cardiomyocytes treated with DMSO (cardiomyocytes), $H_2O_2$, DOX, or AD 198, with or without a pretreatment using the ROS detection agent CM-$H_2$DCFDA. Reagent oxidation was detected by increased fluorescent emission following excitation at 525 nm (x-axis). Y-axis represents cell count. Data are representative of three independent analyses.

To determine whether AD 198 is capable of generating ROS, the relative abilities of AD 198 and DOX to produce the oxidation of the ROS detection reagent $DM-H_2DCFDA$ were studied as described in Example 8. Primary rat ventricular cardiomyocytes were preloaded with $CM-H_2DCFDA$, then treated with either DOX or AD 198 for 2 hr. Oxidation of $CM-H_2DCFDA$ was monitored by increased fluorescence of the reagent due to oxidation by anthracycline-generated ROS. As shown in FIG. 19, $H_2O_2$, a positive control, produced an approximately 26-fold increase in fluorescence over cells treated with either $H_2O_2$ or $CM-H_2DCFDA$, alone. Both AD 198 and DOX treatments produced similar increases in $CM-H_2DCFDA$ fluorescence, at 44- and 37-fold respectively, indicating comparable generation of ROS over the same time frame.

Given the ability of AD 198 to generate levels of ROS comparable to DOX, mechanisms by which AD 198 can ameliorate this potentially cardiotoxic effect were investigated. PKCs δ and ε are of particular interest within the context of these studies, since activation of these PKC isoforms has been implicated in cardioprotective signaling within cardiomyocytes. See Liu, G. S., et al., *J. Mol. Cell. Cardiol.* 31, 1937-1948 (1999); and Kawamura, S., et al.,*Am. J. Physiol.*, 275, H2266-H2271 (1998). Further, direct binding and activation of PKC by phorbol esters has been shown to promote cardioprotection in perfused hearts. See Cohen, M. V., et al., *Annu. Rev. Physiol.*, 62, 79-109 (2000).

As described in Example 9, perfused heart studies were used to determine whether AD 198 can induce cardioprotective signaling within rodent hearts through PKC activation. Hearts excised from anesthetized rats were perfused with either DMSO (solvent control), AD 198, or DOX, then subjected to global ischemia by vascular occlusion. Following ischemia, hearts were reperfused with buffer and the recovery of LVDP was monitored using the standard Langendorff perfused heart protocol. See FIG. 20A.

Figure 20B:
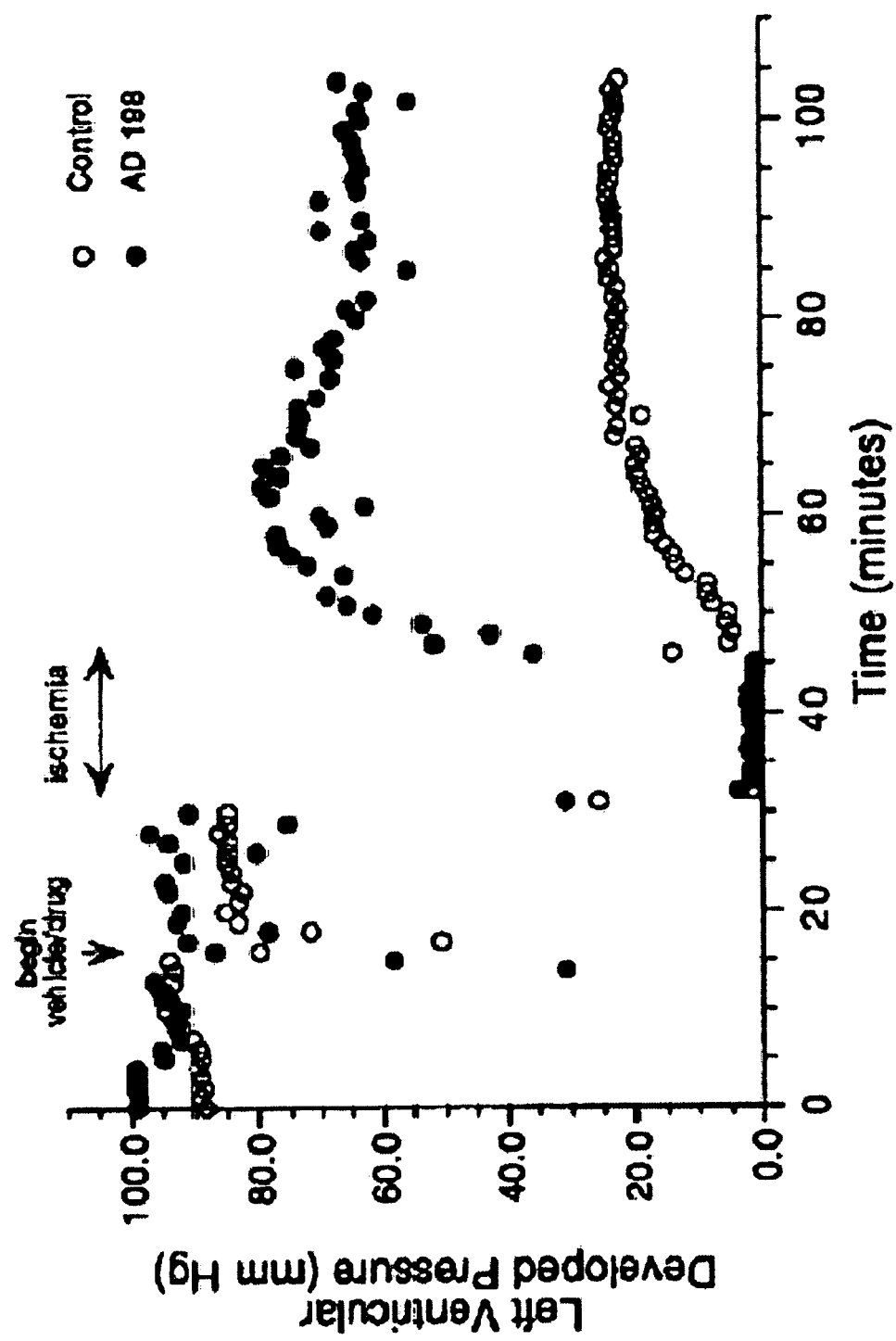
FIG. 20B is a graph showing the cardiac function as measured in terms of LVDP over the timecourse of the Langendorff perfusion studies on isolated rat hearts. Hearts were perfused with 0.1 µM AD 198 (solid circles). Control hearts were perfused with DMSO (open circles). Data are representative of multiple independent analyses.

A 15 min perfusion of 1% DMSO in Krebs-Henseleit buffer prior to 15 min of global ischemia results in a 22% recovery of LVDP to baseline levels after 60 min of reperfusion. See FIG. 20B. Perfusion of 1 µM DOX prior to ischemia lowered LVDP recovery during reperfusion to 7.5% (data not shown). In contrast, perfusion with 1 µM AD 198 prior to global ischemia resulted in LVDP recovery that ranged from 53% to 70% of baseline levels. Interestingly, 0.1 µM AD 198 perfusion prior to ischemia yielded an even higher LVDP recovery of 84.2%.

Figure 21:
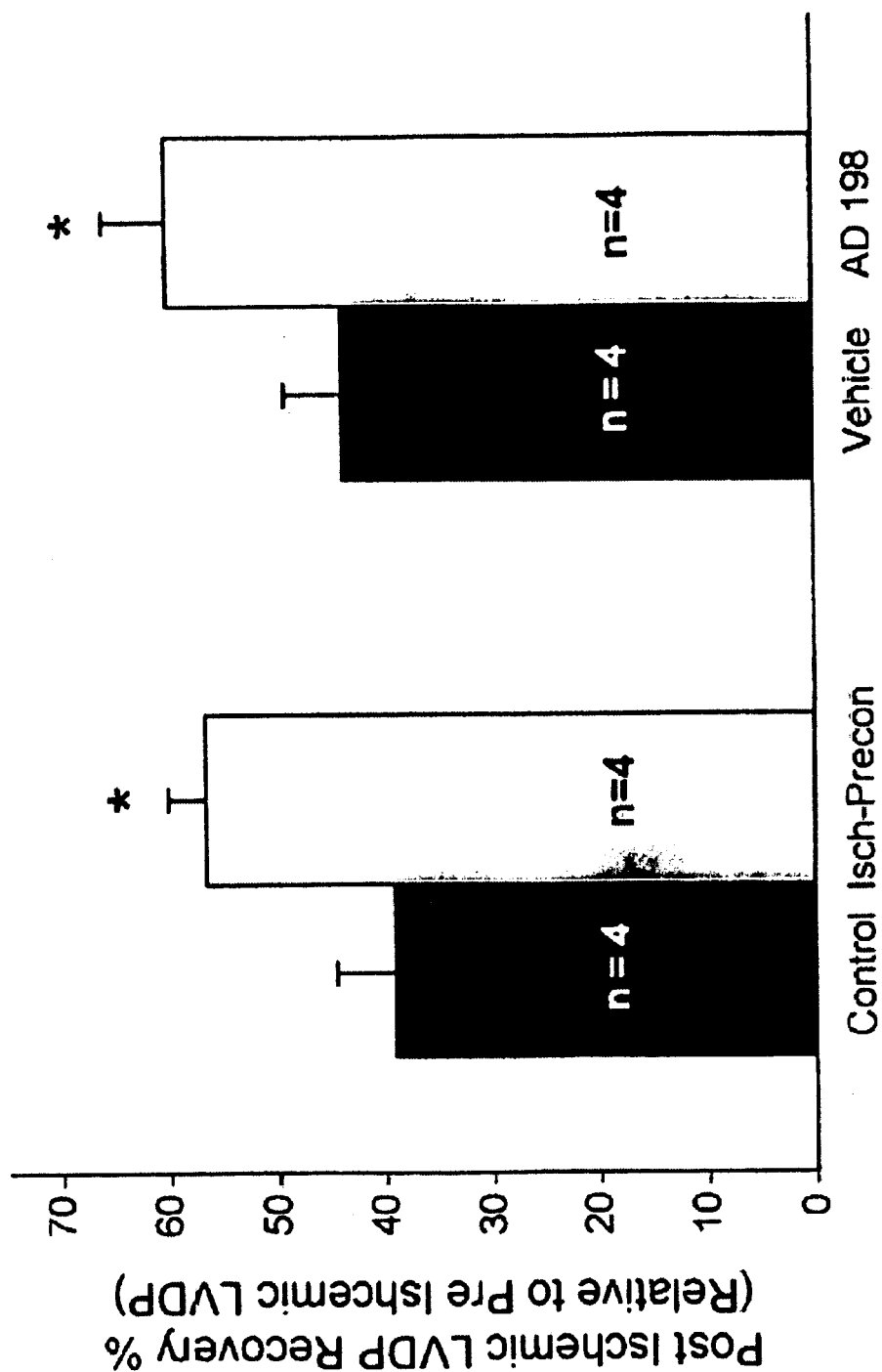
FIG. 21 is a bar graph comparing the cardioprotection afforded by either AD 198 (right-hand shaded bar) or preconditioning ischemia (left-hand shaded bar). Excised C57 mouse hearts were subjected to Langendorff analysis using DMSO (vehicle) and 0.1 µM AD 198 treatment as described for FIGS. 20A and 20B. Preconditioning ischemia was performed by subjecting hearts to three 1 min occlusions prior to global ischemia. Values from control hearts (those not subjected to preconditioning ischemia or drug treatment) are shown in the solid bars.

These results indicate that AD 198, like phorbol esters, confers protection against ischemic damage in rat hearts. Likewise, C57 mouse hearts pretreated with 0.1 µM AD 198 exhibited a 60% recovery of LVDP during post-ischemic reperfusion. See FIG. 21 and Table 3, below. In this study, AD 198 displayed an extent of cardioprotection comparable to that of preconditioning ischemia, which resulted in 56.6% recovery of LVDP.

TABLE 3

Ischemic Protection of Perfused C57 Mouse Hearts by AD 198.

| | Mean LVDP (mm Hg) ± std. Error | | |
|---|---|---|---|
| Treatment | Pre-Ischemic | Post-Ischemic | Percent Recovery |
| Control | 70.9 ± 13.1 | 29.0 ± 8.1 | 39.1 |
| Preconditioning Ischemia | 57.6 ± 5.9 | 32.5 ± 3.6 | 56.6 |
| Vehicle | 78.6 ± 9.2 | 33.5 ± 2.2 | 43.8 |
| AD 198 (0.1 µM) | 69.8 ± 13.6 | 41.0 ± 5.9 | 60.0 |

Figure 22:
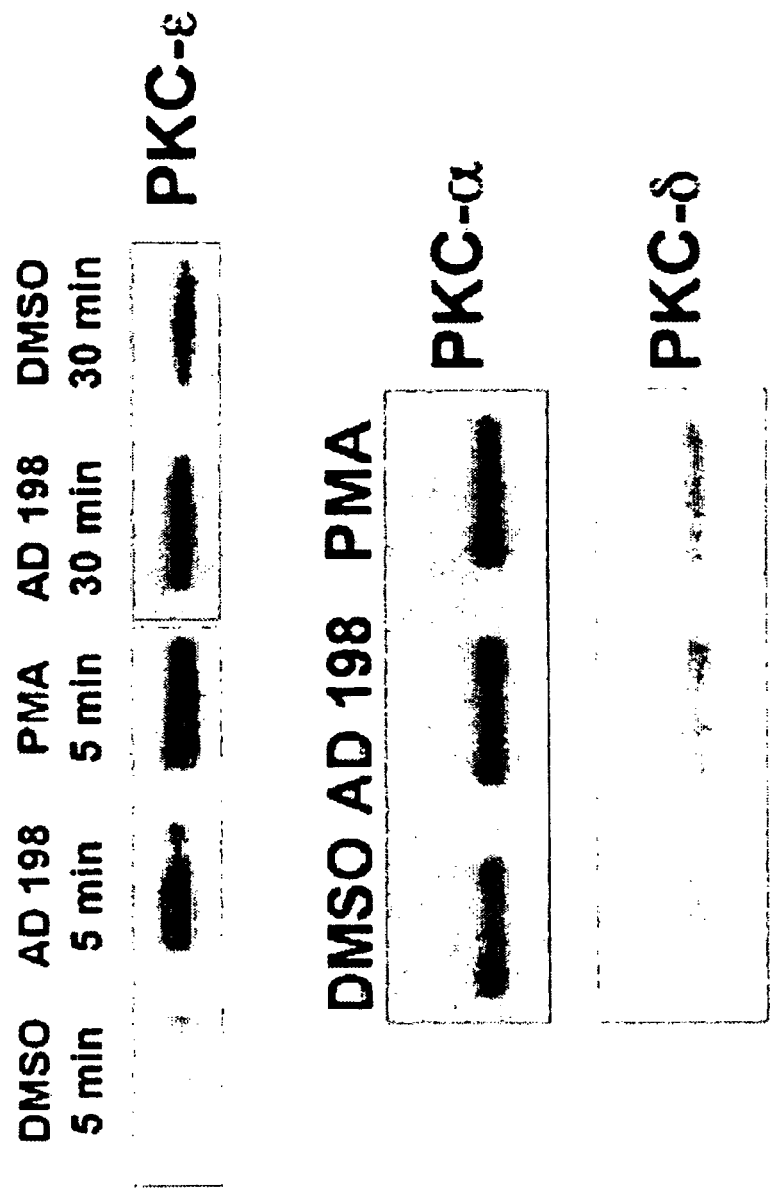
FIG. 22 is an immunoblot analysis of PKC translocation in drug-treated rat cardiomyocytes. Isolated primary rat cardiomyocytes were treated with either AD 198 (0.1 μM) or PMA (0.1 μM) for 5 and 30 min for PKC-ε, or for 5 min for PKC-α or PKC-δ. Total membrane fractions were isolated by differential centrifugation in the absence of non-ionic detergent, subjected to SDS-PAGE and prepared for immunoblot analysis using antibodies against the PKC isoforms.

Correlated with the cardioprotective effects of AD 198 is its ability to induce rapid, but transient, translocation of PKC-ε in primary rat cardiomyocytes. See FIG. 22. Freshly isolated rat cardiomyocytes were exposed to either DMSO, 0.1 µM AD 198, or 0.1 µM PMA for 5 min or 30 min prior to cell fractionation. Immunoblot analysis was as decribed in Example 10. After 5 min exposure to either AD 198 or PMA, there is a 5-fold increase in membrane-associated PKC-ε compared with cardiomyocytes treated with DMSO alone. However, after 30 min, the amount of membrane-associated PKC-E decreased approximately 50%. Marginal translocation of PKC-δ was observed within 5 min of AD 198 and PMA exposure, while no translocation of PKC-α was detected. Thus, as with the cardioprotective PKC activator PMA, AD 198-mediated cardioprotection is associated with rapid, but transient translocation of PKC-ε in primary rat cardiomyocytes.

Figure 23A:
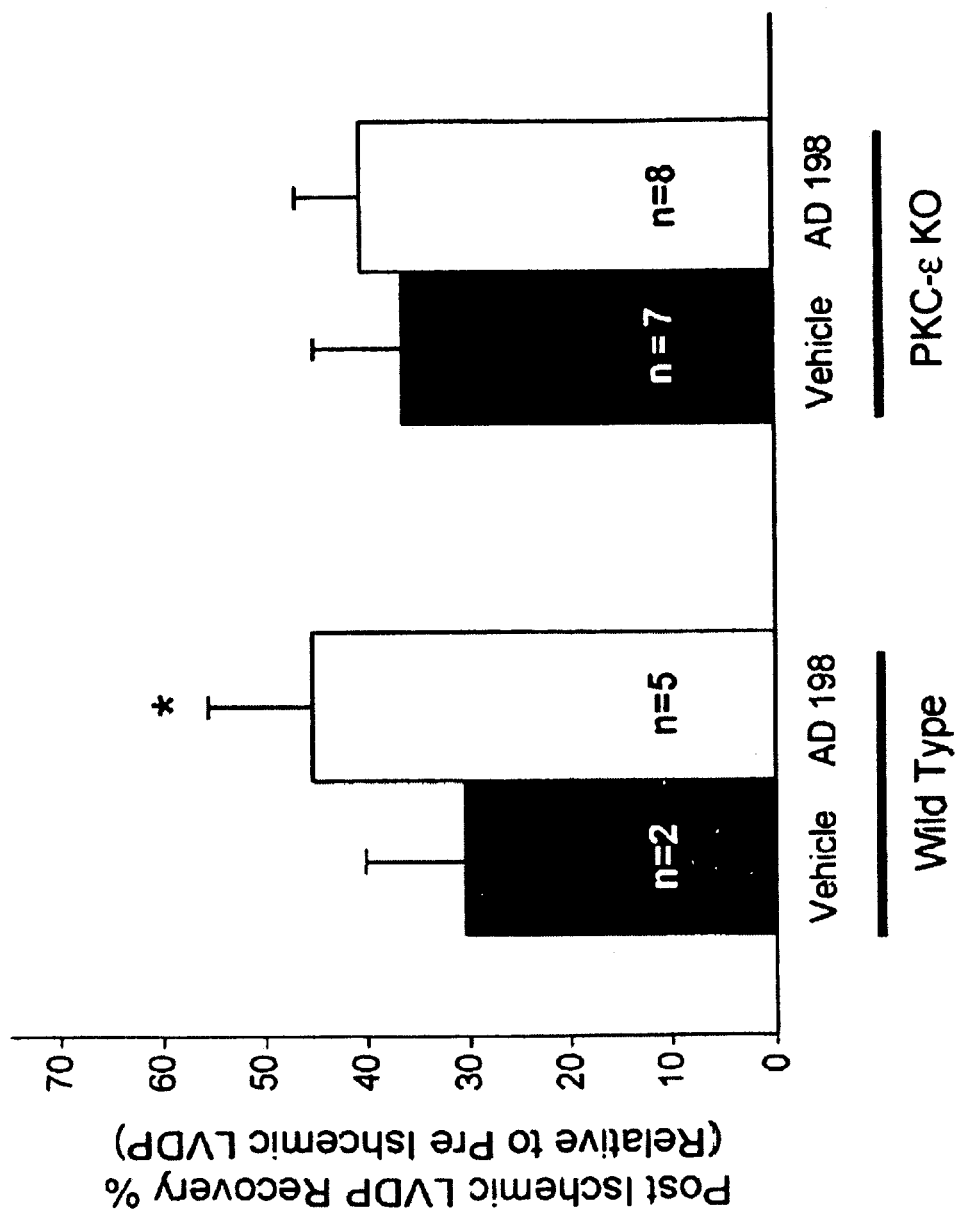
FIG. 23A is a bar graph comparing AD 198 cardioprotection in wild type and PKC-ε$^{(-/-)}$ (PKC-ε KO) C57 mice using Langendorff perfusion analysis. Excised mouse hearts were subjected to Langendorff analysis using vehicle and 0.1 μM AD 198 treatment conditions as described in the legends of FIGS. 13A and 13B. Results were expressed as percent recovery of post-ischemic LVDP after 60 min of reperfusion. The two bars on the left compare AD 198 treatment (shaded bar) to treatment with DMSO (solid bar) in wild type mice. The two bars on the right compare AD 198 treatment (shaded bar) to treatment with DMSO (solid bar) in PKC-ε KO mice.
Figure 23B:
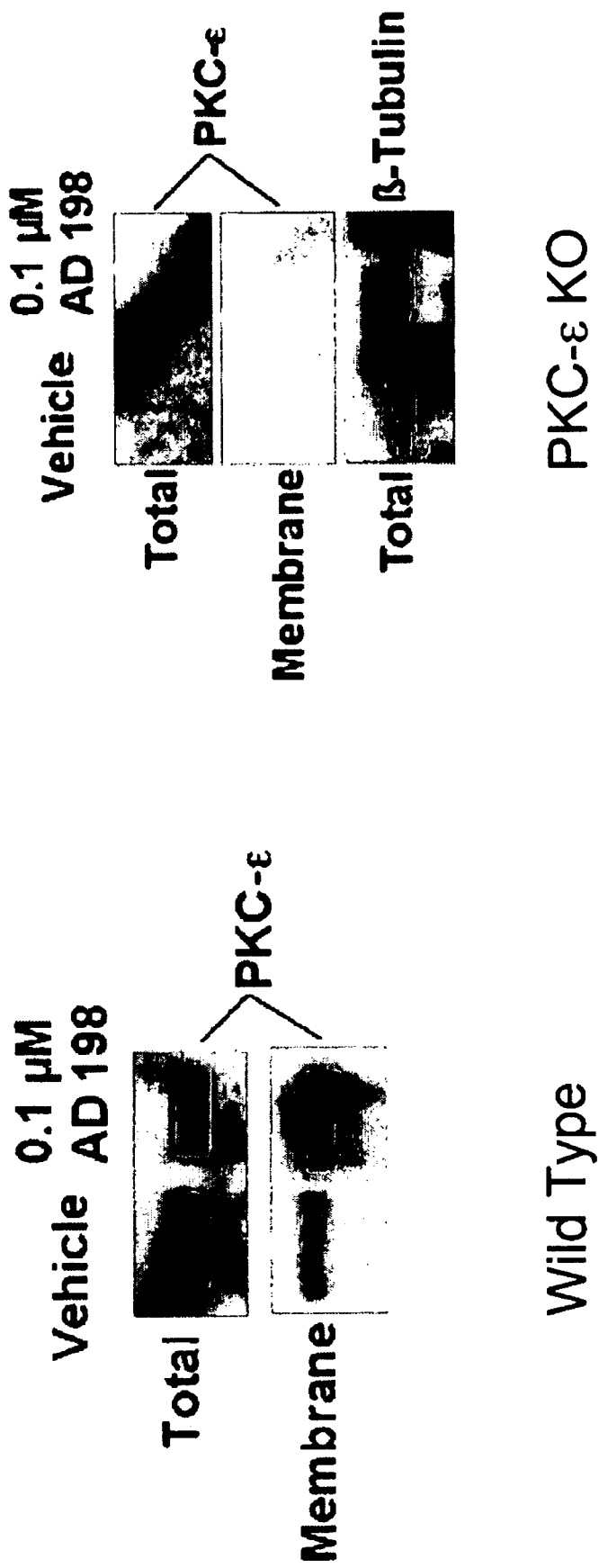
FIG. 23B is an immunoblot analysis of PKC-ε expression and translocation in wild type and PKC-ε$^{(-/-)}$ (PKC-ε KO) mice in fractioned ventricular myocytes from excised hearts following perfusion analysis as described for FIG. 23A.

To determine whether PKC-ε is the principal target of AD 198 in mediating cardioprotection, the cardioprotective effects of AD 198 in hearts excised from PKC-ε knockout (KO) mice were assessed according to the reperfusion methods described in Example 9. The results of the reperfusion study are shown in FIG. 23A. In homozygous wild-type mice, perfusion with vehicle (DMSO) prior to global ischemia resulted in a 30% recovery of LVDP, while perfusion with 0.1 µM AD 198 prior to global ischemia produced an increase in recovery of LVDP of 45%. AD 198-mediated cardioprotection correspond to a pronounced translocation of PKC-ε to the membrane fraction of ventricular myocytes isolated from drug-treated hearts. See FIG. 23B. In contrast, PKC-ε$^{(-/-)}$ mice were not afforded significant protection by AD 198 perfusion compared with control (DMSO) mice. These findings suggest that PKC-ε plays a principal role in cardioprotection by AD 198, as recovery of LVDP corresponds to PKC-ε translocation to membrane fractions excised from treated hearts.

Example 12

Cardioprotection of AD 198 Used in Combination Treatment with Trastuzumab

Figure 24A:
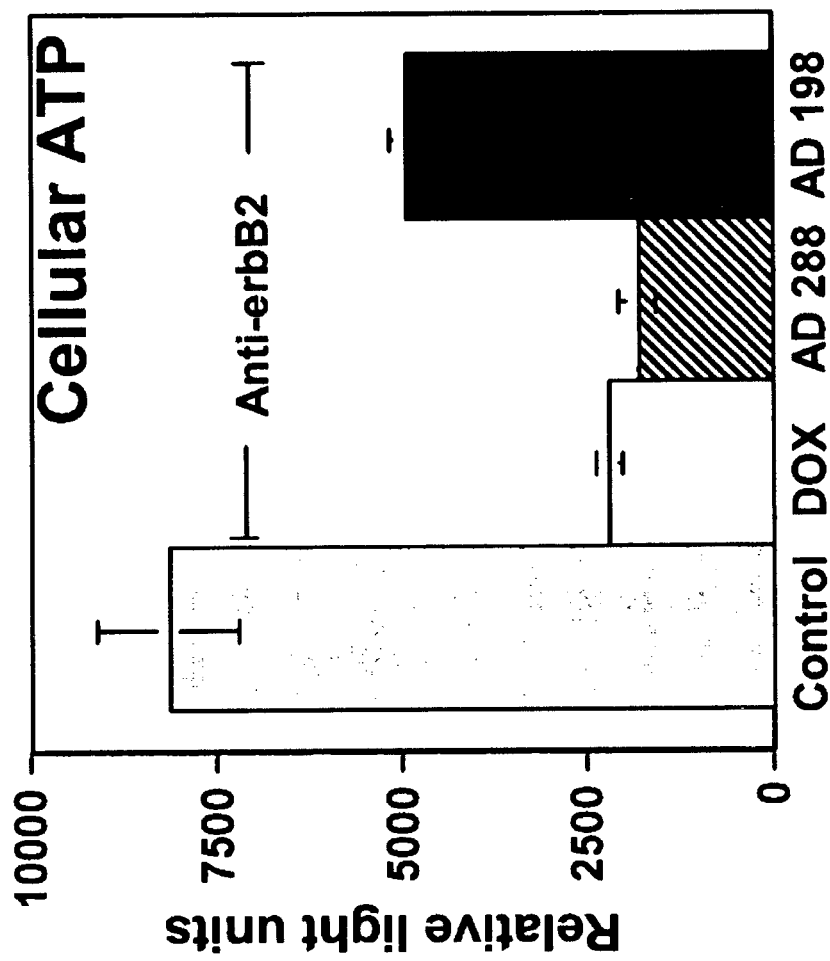
FIG. 24A is a bar graph showing the effect of AD 198 on adenosine triphosphate (ATP) depletion in anti-erbB-2-antibody-treated neonatal rat ventricular myocytes (NRVM). NRVM were pretreated with 200 nM of either DOX (open bar), AD 288 (striped bar), or AD 198 (solid bar) prior to treatment with anti-erbB-2 antibody. ATP content was measured by luciferin/luciferase assay as described in Grazette, L. P., et al., *J. Am. Coll. Cardiol.*, 44, 2231-2238 (2004). The value from control myocytes is shown by the shaded bar. Mean and standard error are derived from at least 3 independent determinations.
Figure 24B:
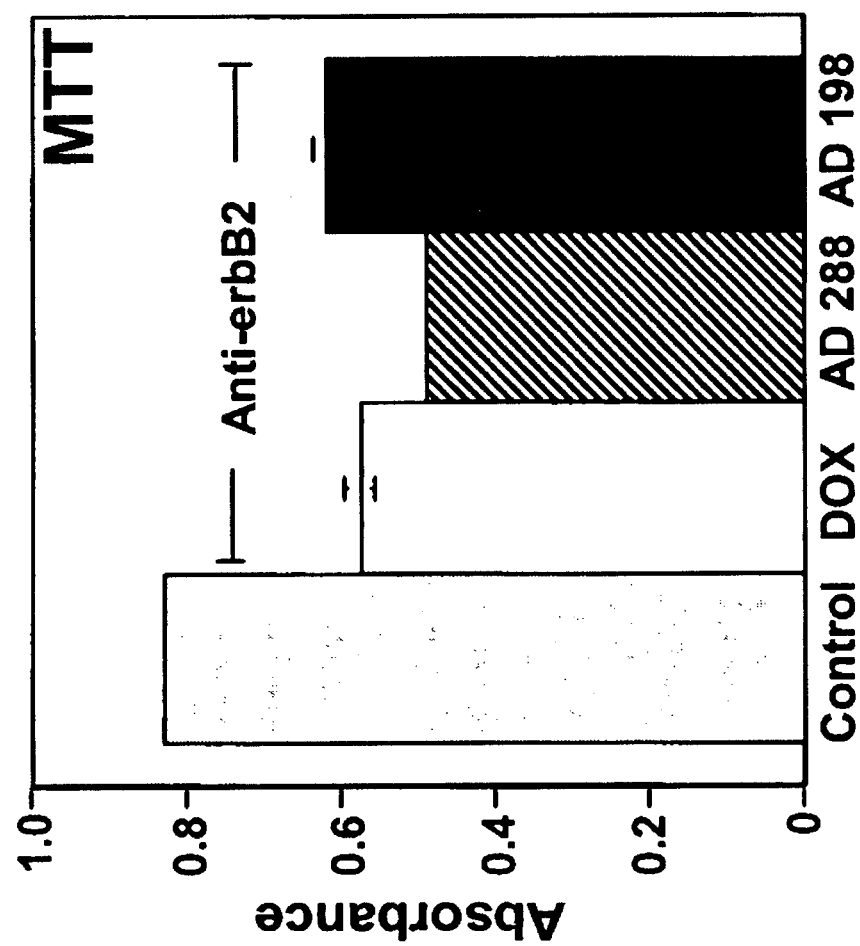
FIG. 24B is a graph showing the effect of AD 198 on mitochondrial redox function in anti-erbB-2 treated NRVM. NRVM were treated as described for FIG. 24A. Redox activity is measured by the absorbance of dye in the MTT assay as described in Grazette. L. P., et al., *J. Am. Coll. Cardiol.*, 44, 2231-2238 (2004). Values for control NRVM, DOX treated NRVM, AD 288 treated NRVM and AD 198 treated NRVM are indicated by the shaded, open, striped and solid bars, respectively. Mean and standard error are derived from at least 3 independent determinations.

One of several potential therapeutic applications of the cardioprotective effects of AD 198 is in combination with the cardiotoxic anti-erbB-2 antibody, trastuzumab, in the treatment of HER2/neu+ breast cancer. The anti-erbB-2 antibody has previously been shown to deplete ATP levels in NRVM by 50%. See Grazette, L. P., et al., *J. Am. Coll. Cardiol.*, 44, 2231-2238 (2004). Using identical conditions, NRVM (prepared from the hearts of Sprague-Dawley pups as described in Matsui, T., et al., *Circulation*, 100, 2373-2379 (1999)) were pretreated with 200 nM of either DOX, AD 288, or AD 198 1 hr prior to treatment with anti-erbB-2 antibody (clone 9G6 from Oncogene, Cambridge, Mass., United States of America). DOX and AD 288 pretreatment increased ATP depletion. See FIG. 24A. AD198 pretreatment decreased inhibition of ATP depletion by anti-erbB-2 antibody from 50% down to 39%. Further, as shown in FIG. 24B, AD 198 also protected NRVM from anti-erbB-2-mediated depletion of redox activity as measured using the MTT assay as described previously in this context. See Grazette, L. P., et al., *J. Am. Coll. Cardiol.*, 44, 2231-2238 (2004). This observation suggests that AD 198 induces cardioprotection in perfused rat hearts ex vivo at drug concentrations comparable to those achieving a cancer chemotherapeutic response in vivo. Further, the results suggest that AD 198 protects cardiomyocytes from cardiotoxic actions of erbB-2 receptor interference.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for providing cardioprotection in a subject in need thereof, the method comprising administering to the subject an effective amount of a compound of Formula (I):

(I)

wherein:
A comprises a $C_4$-$C_8$ alkanoate moiety;
$R_1$ is H;
$R_2$ is benzyl; and
$R_3$ is H or methoxy;
or a pharmaceutically acceptable salt thereof.

2. The method of claim 1, wherein A is selected from the group consisting of:

3. The method of claim 2, wherein the compound of Formula I is selected from the group consisting of:

and

4. The method of claim 1, wherein the administering to the subject an effective amount of a compound of Formula (I) induces the activation of protein kinase C-epsilon (PKC-ε) in a cardiomyocyte, thereby inducing a cardioprotective effect.

5. A method of treating a cancer, the method comprising administering to a subject in need of treatment thereof an effective amount of a compound of Formula (I):

(I)

47 wherein:
A comprises a C4-C8 alkanoate moiety;
R1 is H;
R2 is benzyl; and
R3 is H or methoxy;
or a pharmaceutically acceptable salt thereof; and
administering to the subject in need of treatment thereof an additional therapeutic agent comprising one or more anti-cancer agents; wherein the administering of the compound of Formula (I) and the additional therapeutic agent provides a synergistic effect.

6. The method of claim 5, wherein the additional therapeutic agent comprises imatinib mesylate.

7. The method of claim 5, wherein the cancer is chronic myeloid leukemia (CML).

8. The method of claim 1, wherein the subject is undergoing treatment for a cancer.

9. The method of claim 1, wherein the compound of Formula (I) is administered in a dose that would be cardiotoxic for an anthracycline compound having a structure other than that of Formula (I).

10. The method of claim 1, further comprising administering the compound of Formula (I) in combination with at least one or more additional therapeutic agents.

11. The method of claim 10, wherein the one or more additional therapeutic agents comprise at least one or more anti-cancer agents.

12. The method of claim 11, wherein the at least one or more anti-cancer agents is selected from the group consisting of antimetabolites, antimicrotubules, alkylating agents, and antibodies.

13. The method of claim 12, wherein the at least one or more additional therapeutic agents comprises a monoclonal antibody.

14. The method of claim 13, wherein the monoclonal antibody comprises trastuzumab.

15. The method of claim 8, wherein the cancer comprises a human epidermal growth factor receptor 2 (HER2) positive breast cancer.

16. A method for treating a drug resistant cancer, wherein the drug resistant cancer is adult chronic myeloid leukemia (CML), the method comprising administering to a subject in need of treatment thereof an effective amount of a compound of Formula (I):

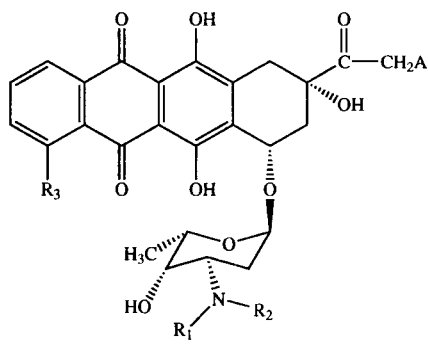

(I)

wherein:
A comprises a C$_4$-C$_8$ alkanoate moiety;
R$_1$ is H;

48

R$_2$ is benzyl; and
R$_3$ is H or methoxy;
or a pharmaceutically acceptable salt thereof.

17. The method of claim 16, wherein A is selected from the group consisting of:

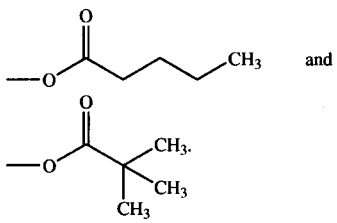

18. The method of claim 17, wherein the compound of Formula (I) is selected from the group consisting of:

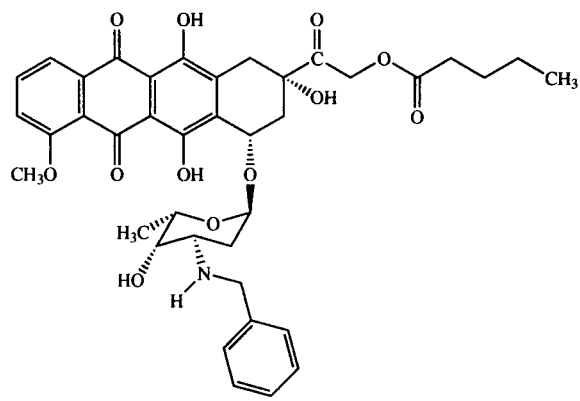

and

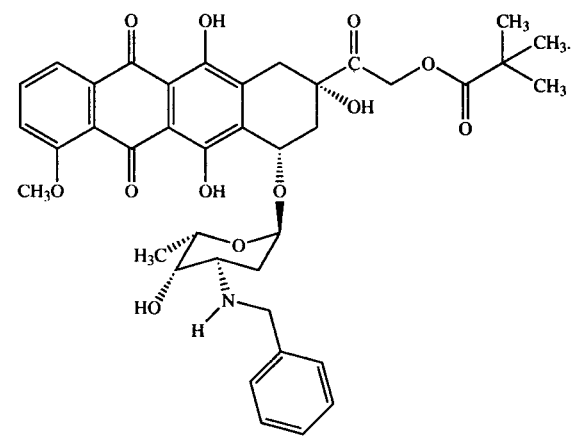

19. The method of claim 16, wherein the administering an effective amount of a compound of Formula (I) provides cardioprotection to the subject in need of treatment thereof.

20. The method of claim 16, wherein the drug-resistant cancer is resistant to imatinib mesylate.

* * * * *